United States Patent [19]

Trova et al.

[11] Patent Number: 5,208,247
[45] Date of Patent: May 4, 1993

[54] PYRIDINIUM COMPOUNDS WHICH ARE USEFUL AS ANTAGONISTS OF PLATELET ACTIVATING FACTOR

[75] Inventors: Michael P. Trova, Salisbury Mills; Allan Wissner, Ardsley, both of N.Y.

[73] Assignee: American Cyanamid Company, Stamford, Conn.

[21] Appl. No.: 738,961

[22] Filed: Aug. 1, 1991

[51] Int. Cl.$^5$ ............................................ C07D 213/02
[52] U.S. Cl. ..................................... 514/358; 546/347
[58] Field of Search ......................... 546/347; 514/358

[56] References Cited

U.S. PATENT DOCUMENTS 4,916,145 4/1990 Tilley et al. .......................... 514/357

OTHER PUBLICATIONS

Baker, *Journal of Medicinal Chemistry*, vol. 12, pp. 677–680, Jul. 1969.
Hansch, *Journal of Medicinal Chemistry*, vol. 19(9) pp. 1089–1093, 1976.
Doll, *Journal of Medicinal Chemistry*, vol. 19(9) pp. 1079–1088, 1976.

*Primary Examiner*—C. Warren Ivy
*Assistant Examiner*—Zinna N. Davis
*Attorney, Agent, or Firm*—H. G. Jackson

[57] ABSTRACT

The invention is aryl, amide, imide and carbamate pyridine antagonists of platelet activating factor.

25 Claims, No Drawings

PYRIDINIUM COMPOUNDS WHICH ARE USEFUL AS ANTAGONISTS OF PLATELET ACTIVATING FACTOR

BACKGROUND OF THE INVENTION

Platelet Activating Factor (PAF), 1-O-hexadecyl-/octadecyl-2-acetyl-sn-glyceryl-3-phosphorylcholine, is an ether lipid produced by a variety of different cell types. Recent studies [Snyder, F., Ann. Rep. Med. Chem., 17, 243 (1982); Pinckard, R. N., et. al., J. Adv. Inflammation Res., 4, 147 (1982); O'Flaherty, J. T., et. al., Clin. Rev. Allergy, 1, 353 (1983); Vargaftig, B. B., et. al., J. Trends. Pharmacol. Sci., 4, 341 (1983)] have shown PAF to be an important mediator of allergic disease. When injected into mammals, PAF induces hemodynamic and hematological changes including hypotension, platelet aggregation, neutropenia, disseminated intravascular coagulation, increases in vascular permeability, bronchoconstriction, tissue injury (hypoxia and necrosis) and eventually death (reviewed by Cammussi, G. Kidney Int. 29, 469, (1986). In recent years, it has been postulated that PAF is the mediator of tissue injury in mammals undergoing endotoxic shock due to bacterial sepsis (Terashita, Z., Y. Imura, K. Nishikawa and S. Sumida 1985, Eur. J. Pharmacol. 109:257-261; Doebber, T. W., M. S. Wu, J. C. Robbins, B. M. Choy, M. N. Chang and T. Y. Shen 1985, Biochem. Biophys. Res. Comm. 127:799-808; Inarrea, P., Gomez-Cambronero, J. Pascual, M. del Carmen Ponte, L. Hernando and M. Sanchez-Crespo. 1985, Immunopharmacology, 9:45-52). These studies, in mammals, have shown that PAF is produced in large amounts when the said mammal has been treated with endotoxin. In addition, mammals undergoing endotoxic shock exhibit all of the clinical symptoms associated with the administration of PAF. In addition, PAF is implicated in asthma, respiratory distress syndrome, lung edema and other inflammatory and cardiovascular diseases.

The compounds of the present invention have proven to be specific inhibitors of the biological effects of PAF and are consequently useful for the treatment of asthma, anaphylactic and septic (endotoxic) shock, psoriasis, bowel necrosis, adult respiratory distress syndrome, transplant rejection, thrombosis, stroke, cardiac anaphylaxis and cancer.

Concurrently, with the realization that PAF is an important mediator of inflammatory diseases in mammals, a number of structurally different antagonists of PAF have been developed. References to some of these antagonists are listed hereinbelow.

Terashita, Z.; Imura, Y.; Takatani, M.; Tsushima, S.; Nishikawa, K., J. Pharmacol. Exp. Ther., 1987, 242, 263-268.

Takatani, M.; Yoshioka, Y.; Tasaka, A.; Terashita, Z.-I.; J. Med. Chem., 1989, 32, 56–64.

Tsushima, S.; Takatani, M.; Kohei, N. Eur. Patent Appln. EP 301751 (Feb. 1, 1989).

Tomesch, J. C. U.S. Pat. No. 4,820,718 (Apr. 11, 1989).

Gustafson, A.; Handley, D. A.; Tomesch, J. C.; Prashad, M. FASEB J, 1989, 3, A1224.

Page, C.; Abbott, A. TIPS, Jul. 10, 1989, 1.

U.S. Pat. No. 4,916,145 (Oct. 4, 1990).

European Patent Appln. EP 327,962 (Aug. 16, 1989).

European Patent Appln. EP 301,751 (Feb. 1, 1989).

European Patent Appln. EP 353,474 (Feb. 7, 1990).

Spanish Patent Appln. ES 2,010,937 (Dec. 1, 1989).

Spanish Patent Appln. ES 2,010,932 (Dec. 1, 1989).

European Patent Appln. EP 353,777 (Feb. 7, 1990).

U.S. Pat. No. 4,820,718 (Nov. 4, 1989).

BRIEF SUMMARY OF THE INVENTION

The compounds of the present invention are represented by the formula:

Formula 1

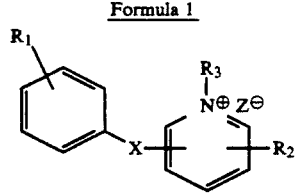

wherein:

(A) X is a divalent radical selected from the group consisting of:

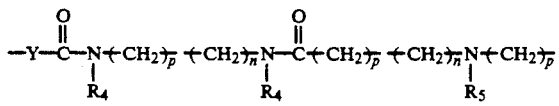

wherein Y is a divalent radical selected from the group represented by $OCH_2$, $(CH_2)_n$, $(CH_2)_{n+1}O$; p is the integer 0, 1, 2, or 3; n is the integer 0, 1, or 2; $R_4$ is selected from the group consisting of hydrogen, phenyl, $-COR_6$ or $-SO_2R_7$; wherein $R_6$ is selected from $C_1$-$C_6$ alkyl, $C_1$-$C_6$ alkenyl, $C_1$-$C_6$ alkylamino, $C_1$-$C_6$ alkoxy, phenyl, aminophenyl, substituted phenyl and substituted aminophenyl and the substituents are selected from the group consisting of one or more of the following $C_1$-$C_4$ alkyl, $C_1$-$C_4$ alkoxy, halogen and trifluoromethyl; $R_7$ is selected from the group of $C_1$-$C_{25}$ alkyl, $C_1$-$C_{25}$ alkenyl, phenyl and substituted phenyl and the substituents are selected from the group consisting of $C_1$-$C_{20}$ alkyl, $C_1$-$C_{20}$ alkoxy, halogen and trifluoromethyl; $R_5$ is selected from the group consisting of $-COR_6$ and $-SO_2R_7$ wherein $R_6$ and $R_7$ are as previously described above with the proviso that when

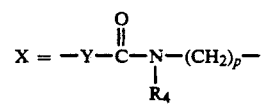

and Y is $(CH_2)_n$ with $n=0$, $R_4$ cannot be hydrogen or phenyl;

(B) $R_1$ represents one or more substituents of the aromatic ring which may be the same or different and is selected from the group consisting of:
(i) $C_1$-$C_{25}$ alkyl, $C_1$-$C_{25}$ alkenyl, $C_1$-$C_{25}$ alkoxy, $C_1$-$C_{25}$ alkenyloxy, $C_1$-$C_{25}$ thioalkyl, phenyl, phenoxy, substituted phenyl, and substituted phenoxy wherein the substituents are selected from the group consisting of $C_1$-$C_{20}$ alkyl, $C_1$-$C_{20}$ alkoxy, halogen, and trifluoromethyl;
(ii) halogen, trifluoromethyl, cyano, and nitro;
(iii) $-CO_2R_7$, $-CONHR_7$, $-OCONHR_7$, and $-NHCOR_7$ wherein $R_7$ is as previously described above;

(C) the moiety $R_2$ represents one or more substituents of the pyridine ring which may be in any position and are selected from the group consisting of hydrogen, $C_1$-$C_5$ alkyl, $C_1$-$C_5$ alkoxy, and halogen;

(D) the heterocycle is bonded to the X-group at optionally the 2, 3, or 4 position;

(E) the group $R_3$ is selected from the group consisting of $C_1$-$C_8$ alkyl, $C_1$-$C_8$ halogen (bromine, chlorine or fluorine) substituted alkyl, benzyl, hydrogen or N-oxide; $Z^{\ominus}$ represents a pharmacologically acceptable anion.

DETAILED DESCRIPTION OF THE INVENTION

The preparation of compound invention encompassed by formulae 4 and 5 is described hereinbelow in Flowsheet A wherein $R_1$, $R_2$, $R_3$, $Z^{\ominus}$, and p are described hereinabove. The substituted acid chlorides 2 needed to prepare the compounds can be prepared as described in the following U.S. Pat. Nos. 4,697,031; 4,699,990; and 4,640,913 and in our copending applications Ser. No. 286,193, filed in December 1988 and Ser. No. 519,525, filed on May 4, 1990. The acid chloride 2 is condensed with substituted alkylamino pyridines 3 in the presence of an excess of base such as pyridine in an inert solvent such as methylene chloride to give amide 4. Amide 4 can be heated with an alkylating agent such as an alkyl halide to give compounds of this invention represented by Formula 5.

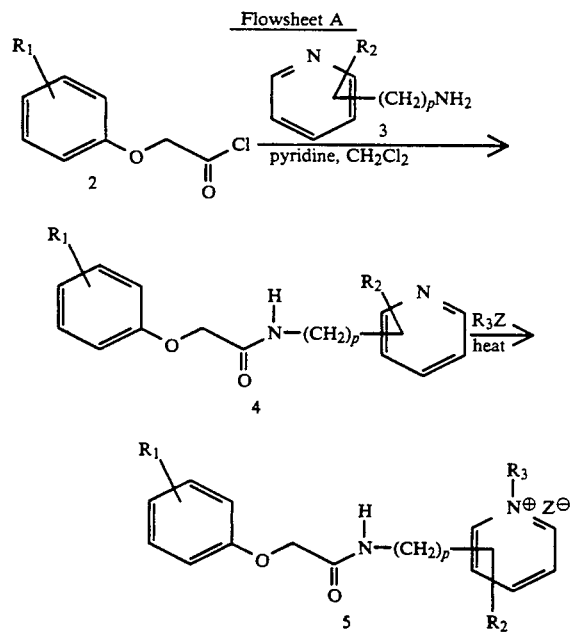

The preparation of compound invention encompassed by Formulae 6 and 7 is described hereinbelow in Flowsheet B wherein $R_1$, $R_2$, $R_3$, $R_6$, $Z^{\ominus}$, and p are described hereinabove. Previously described amide 4 (Flowsheet A) can be converted to imide 6 by heating 4 with an anhydride

a catalytic amount of 4-dimethylaminopyridine (DMAP), and pyridine as a solvent. Imide 6 can be heated with an alkylating agent such as an alkyl halide to give compounds of this invention represented by Formula 7.

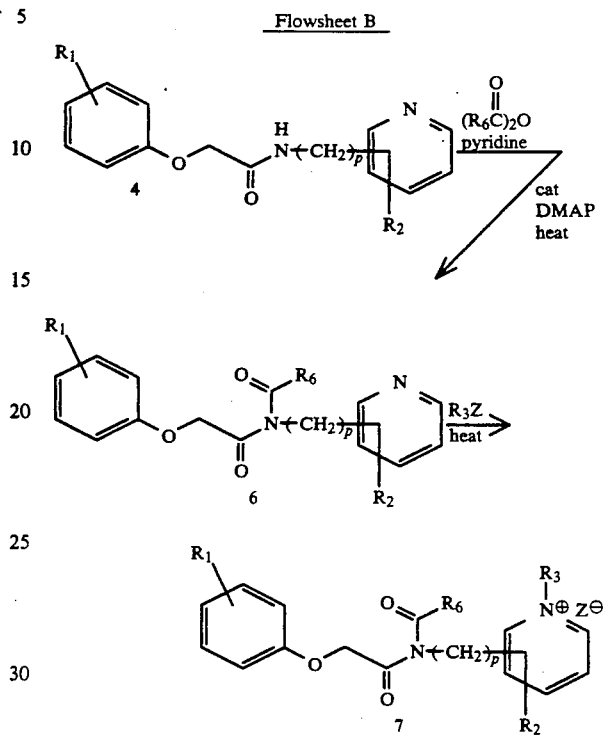

The preparation of compound invention encompassed by Formulae 9 and 10 is described hereinbelow in Flowsheet C wherein $R_1$, $R_2$, $R_3$, $Z^{\ominus}$, n, and p are described hereinabove. The substituted acid chlorides 8 needed to prepare the compounds can be prepared as described in our copending patent application Ser. No. 519,525, filed on May 4, 1990. The acid chloride 8 is condensed with substituted alkylamino pyridines 3 in the presence of an excess of pyridine in an inert solvent such as methylene chloride to give amide 9. Amide 9 can be heated with an alkylating agent such as an alkyl halide to give compounds of this invention represented by Formula 10.

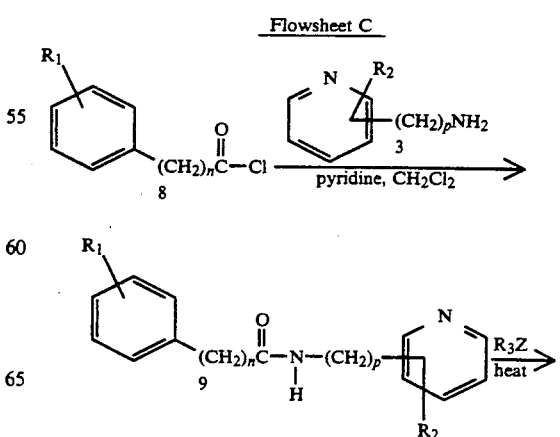

-continued
Flowsheet C

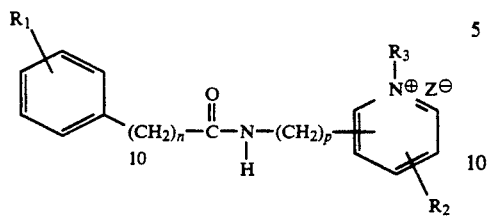
10

The preparation of compound invention encompassed by Formulae 12 and 13 is described hereinbelow in Flowsheet D wherein $R_1$, $R_2$, $R_3$, $Z^\ominus$, n, and p are described hereinabove. The group represented by $R_8$ is one or more substituents which may be the same or different; located at any position on the aromatic ring and is selected from the group consisting of $C_1$-$C_6$ alkyl, $C_1$-$C_6$ alkoxy, halogen or trifluoromethyl. Amide 9, described hereinabove (Flowsheet C), can be reacted first with sodium hydride (NaH) in an inert solvent such as tetrahydrofuran (THF), and then reacted with acid chloride 11 to give imide 12. Imide 12 can be heated with an alkylating agent such as an alkyl halide to give compounds of this invention represented by Formula 13.

-continued
Flowsheet D

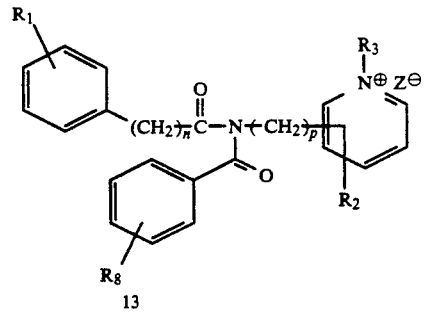
13

The preparation of compound invention encompassed by Formulae 14 and 15 is described hereinbelow in Flowsheet E wherein $R_1$, $R_2$, $R_3$, $R_6$, $Z^\ominus$, n, and p are described hereinabove. Amide 9, described hereinabove (Flowsheet C), can be converted to imide 14 by heating 9 with an anhydride $(R_6CO)_2O$, a catalytic amount of 4-dimethylaminopyridine (DMAP), and pyridine as a solvent. Imide 14 can be heated with an alkylating agent such as an alkyl halide to give compounds of this invention represented by Formula 15.

Alternatively, substituted alkylaminopyridine 3 can be acylated with an anhydride $((R_6CO)_2O)$, a catalytic amount of 4-dimethylaminopyridine (DMAP), and pyridine as a solvent to give amide 16. Amide 16 can be converted to imide 14 by first reaction with 1 equivalent of sodium hydride (NaH) in an inert solvent such as tetrahydrofuran (THF), then sequentially by reaction with acid chlorides 8, described previously in Flowsheet C.

Flowsheet D

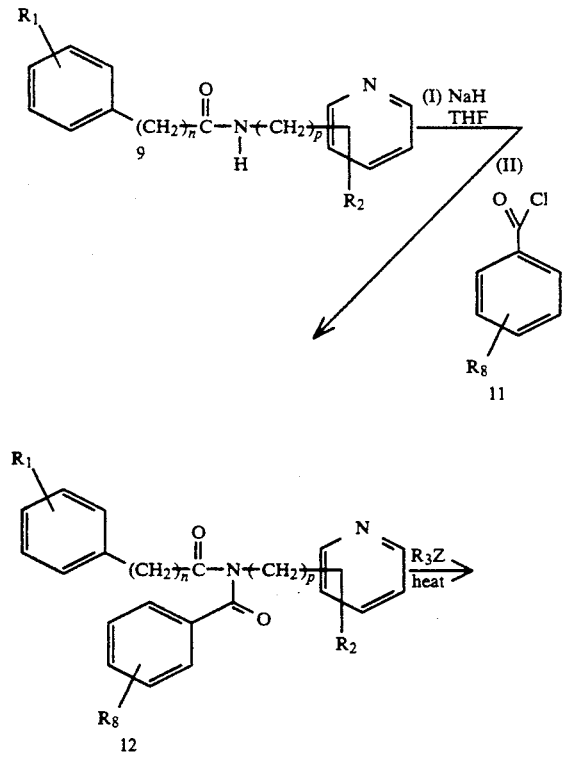

Flowsheet E

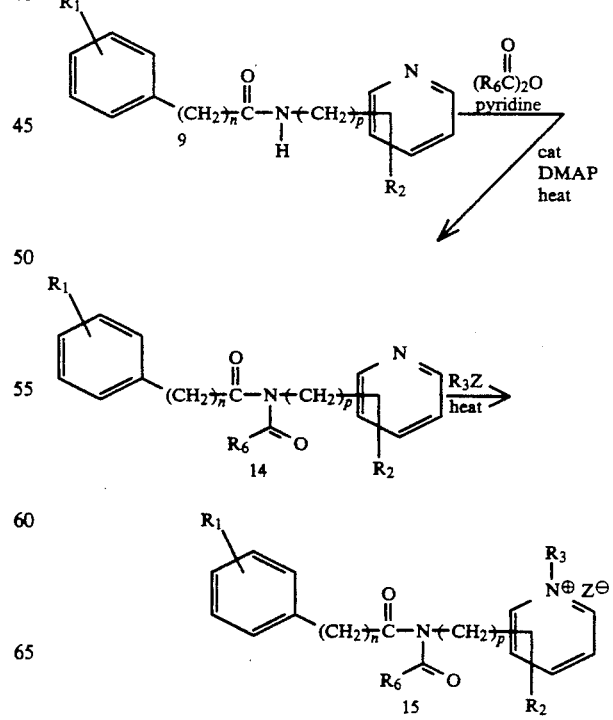

Flowsheet E -continued

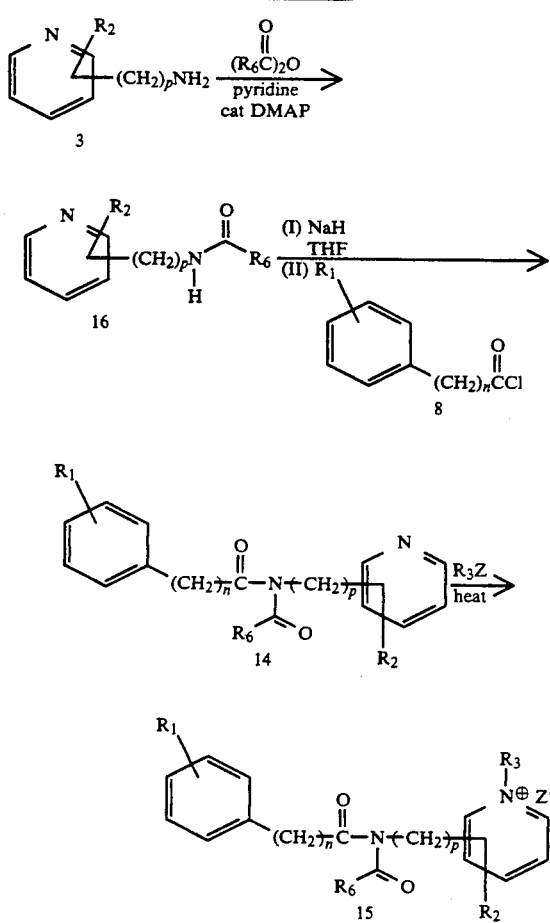

The preparation of compound invention encompassed by Formulae 20 and 21 is described hereinbelow in Flowsheet F wherein $R_1$, $R_2$, $R_3$, $Z^\ominus$, n, and p are described hereinabove. The group $R_9$ is a $C_1$–$C_6$ alkyl group or hydrogen. The substituted esters 17 (or acids when $R_9$ is hydrogen) needed to prepare the compounds can be prepared as described in our copending patent application Ser. No. 519,525, filed on May 4, 1990. Ester 17 (or acid when $R_9$ is hydrogen) can be reduced to alcohol 18 with lithium aluminum hydride (LiAlH$_4$) or similar reducing agent in an inert solvent such as tetrahydrofuran (THF). Alcohol 18 can be converted to carbonate 19 by reaction with phenyl chloroformate, 2 equivalents of pyridine and an inert solvent such as methylene chloride (CH$_2$Cl$_2$). Carbamate 20 can be formed by reaction of carbonate 19 with substituted alkylaminopyridines 3 and heat. Carbamate 20 can be heated with an alkylating agent such as an alkyl halide to give compounds of this invention represented by Formula 21.

Flowsheet F

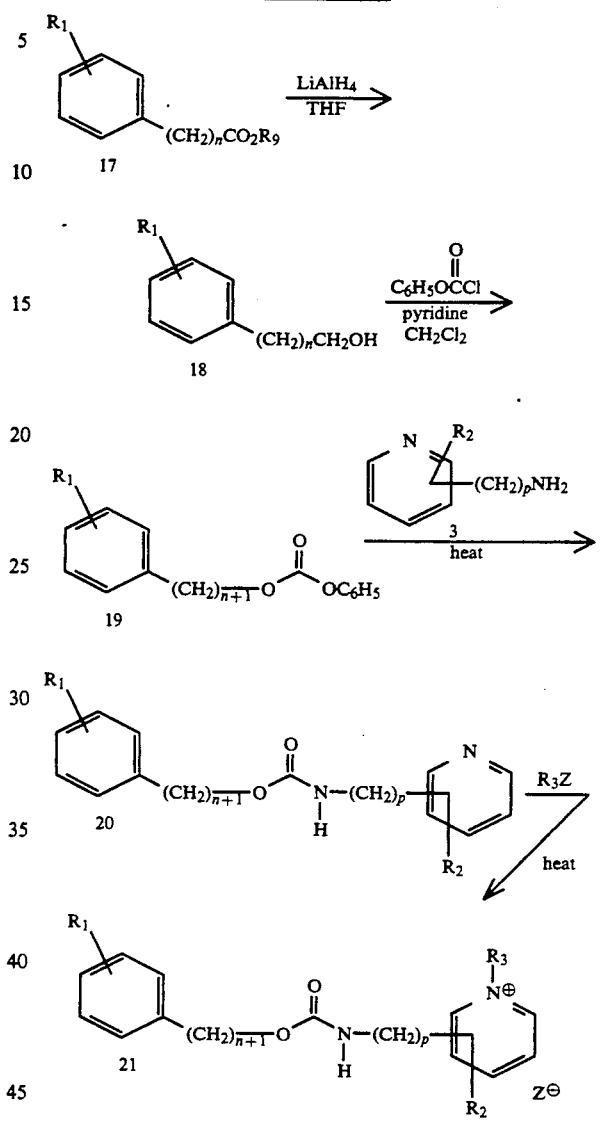

The preparation of compound invention encompassed by Formulae 22 and 23 is described hereinbelow in Flowsheet G wherein $R_1$, $R_2$, $R_3$, $R_6$, $Z^\ominus$, n, and p are described hereinabove. According to Flowsheet G, carbamate 20, described hereinabove (Flowsheet F), can be converted to N-acylcarbamate 22 by reaction with (i) acid chlorides ($R_6$COCl) in the presence of sodium hydride (NaH) or amine bases such as triethylamine (Et$_3$N) or pyridine or (ii) anhydrides (($R_6$C═O)$_2$O) in the presence of a catalytic amount of 4-dimethylaminopyridine (DMAP) in an inert solvent such as pyridine. N-Acylcarbamates 22, so prepared, can be heated with an alkylating agent such as an alkyl halide to give compounds of this invention represented by Formula 23.

Flowsheet G

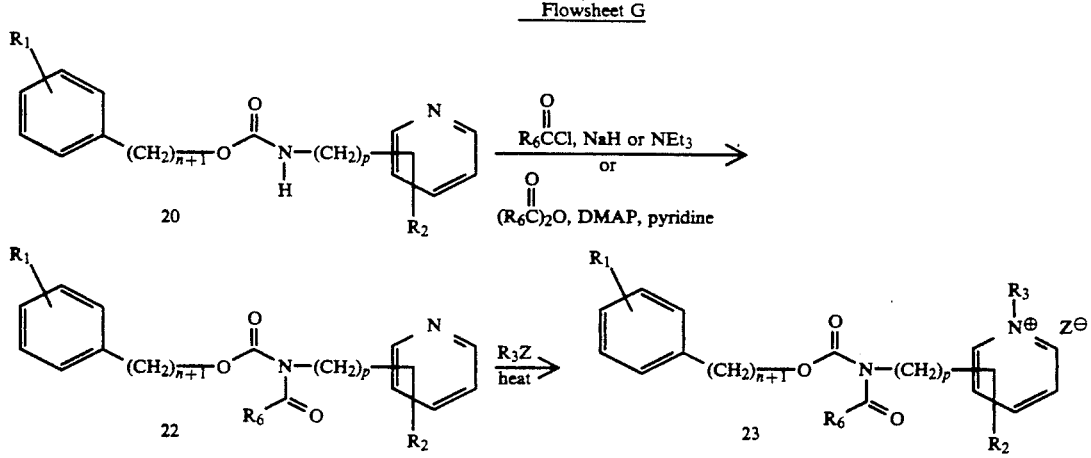

The preparation of compound invention encompassed by Formulae 27 and 28 is described hereinbelow in Flowsheet H wherein $R_1$, $R_2$, $R_3$, $R_6$, $R_9$, $Z^\ominus$, and p are described hereinabove. The substituted esters 24 (or acids when $R_9$ is hydrogen) needed to prepare the compounds of this invention can be prepared as described in our copending patent application Ser. No. 519,525, filed on May 4, 1990. Ester or acid 24 can be reduced to alcohol 25 with lithium aluminum hydride (LiAlH$_4$) or similar reducing agent in an inert solvent such as tetrahydrofuran (THF). Alcohol 25 can be converted to bromide 26 by reaction with phosphorous tribromide (PBr$_3$), pyridine and an inert solvent such as acetonitrile (CH$_3$CN). Transformation of the bromide 26 to amide 27 can be effected by reaction of 26 with the amide-anion of 16, prepared by reaction of 16 with sodium hydride (NaH) in an inert solvent such as tetrahydrofuran (THF). Amide 27 can be heated with an alkylating agent such as an alkyl halide to give compounds of this invention represented by Formula 28.

Flowsheet H

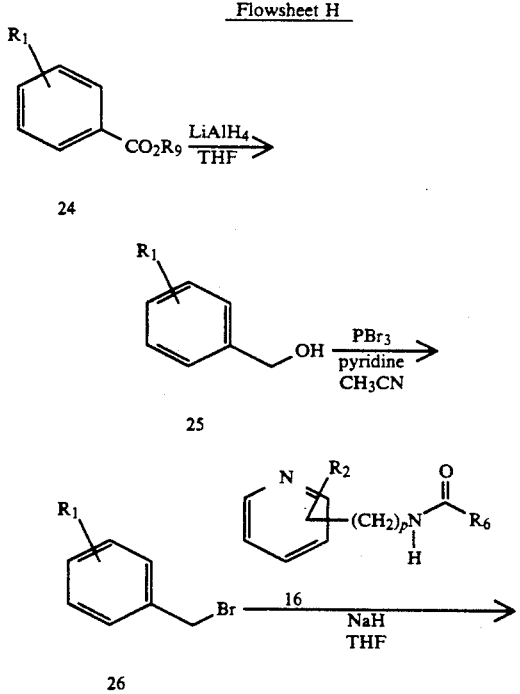

-continued
Flowsheet H

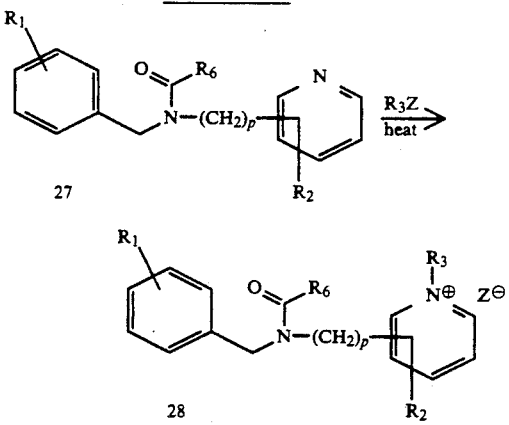

The preparation of compound invention encompassed by Formulae 32 and 33 is described hereinbelow in Flowsheet I wherein $R_1$, $R_2$, $R_3$, $Z^\ominus$, and p are described hereinabove. The integer n is equal to 1, or 2. The substituted amides 29 needed to prepare the compounds of this invention can be prepared by the procedures described for esters 24 as described in our copending patent application Ser. No. 519,525, filed on May 4, 1990. Amide 29 can be reduced to amine 30 with lithium aluminum hydride (LiAlH$_4$) or similar reducing agent in an inert solvent such as tetrahydrofuran (THF). Amine 30 can be converted to amide 32 by reaction with acid chloride 31 (prepared by reaction of the appropriate carboxylic acid with oxalyl chloride in an inert solvent such as methylene chloride in the prsence of a catalytic amount of dimethylformamide) in the presence of a base such as pyridine in an inert solvent such as methylene chloride (CH$_2$Cl$_2$). Amide 32 can be heated with an alkylating agent such as an alkyl halide to give compounds of this invention represented by Formula 33.

Flowsheet I

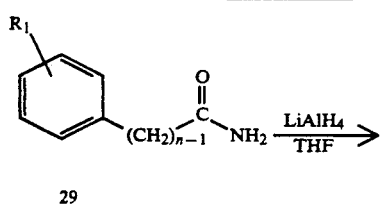
29

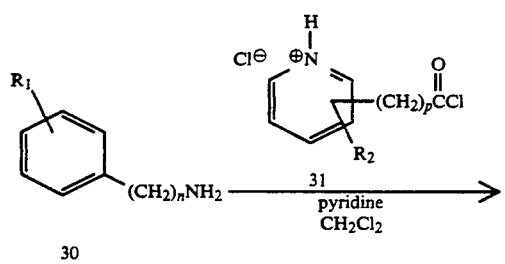
30 → 31

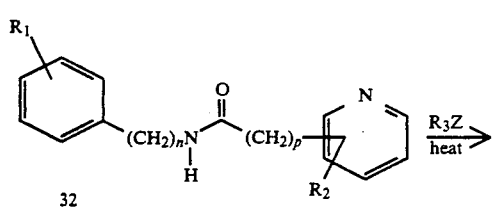
32

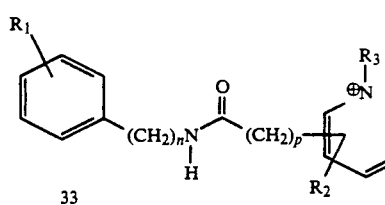
33

Flowsheet J

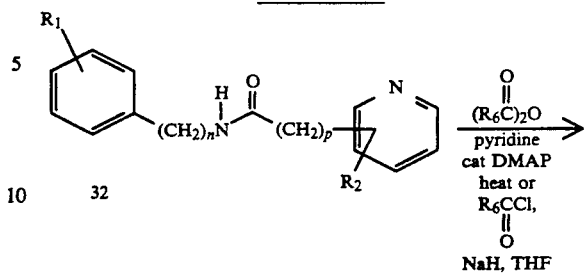
32

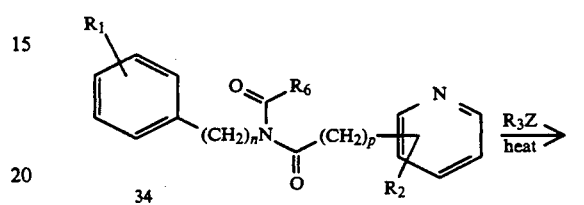
34

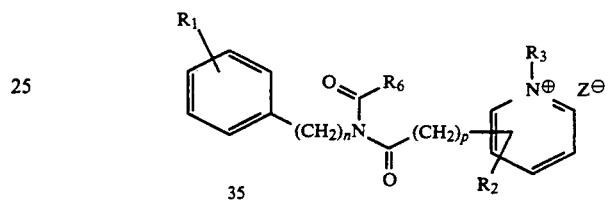
35

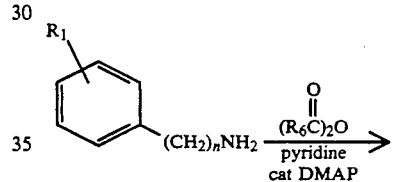
30

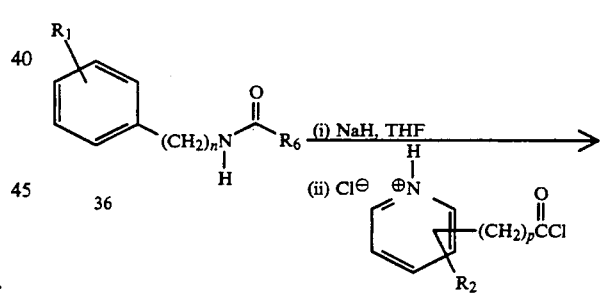
36

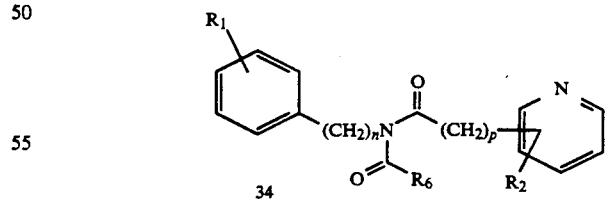
34

The preparation of compound invention encompassed by Formulae 34 and 35 is described hereinbelow in Flowsheet J wherein $R_1$, $R_2$, $R_3$, $R_6$, $Z^\ominus$, n, and p are described hereinabove. Amide 32, described hereinabove (Flowsheet I), can be converted into imide 34 by reaction with anhydrides ($(R_6CO)_2O$) in the presence of a catalytic amount of 4-dimethylaminopyridine (DMAP) in an inert solvent such as pyridine, or by reaction with an acid chloride ($R_6COCl$) in the presence of sodium hydride (NaH) in an inert solvent such as tetrahydrofuran (THF). Alternatively, imide 34 can be prepared by reaction of amide 36 (prepared by reaction of amine 30 with anhydrides ($(R_6C=O)_2O$) in the presence of a catalytic amount of 4-dimethylaminopyridine (DMAP) in an inert solvent such as pyridine) with sodium hydride (NaH) in an inert solvent such as tetrahydrofuran (THF) followed by acid chloride 31. Imide 34 can be heated with an alkylating agent such as an alkyl halide to give compounds of this invention represented by Formula 35.

The preparation of compound invention encompassed by Formula 38 is described hereinbelow in Flowsheet K wherein $R_1$, $R_2$, n, and p are described hereinabove. Amine 30, described hereinabove (Flowsheet I) can be converted into carbamate 37 by reaction with phenyl chloroformate ($C_6H_5OCOCl$) in the presence of a base such as pyridine in an inert solvent such as methylene chloride ($CH_2Cl_2$). Carbamate 37 upon heating in the presence of substituted alkylaminopyridines 3 provides ureas 38.

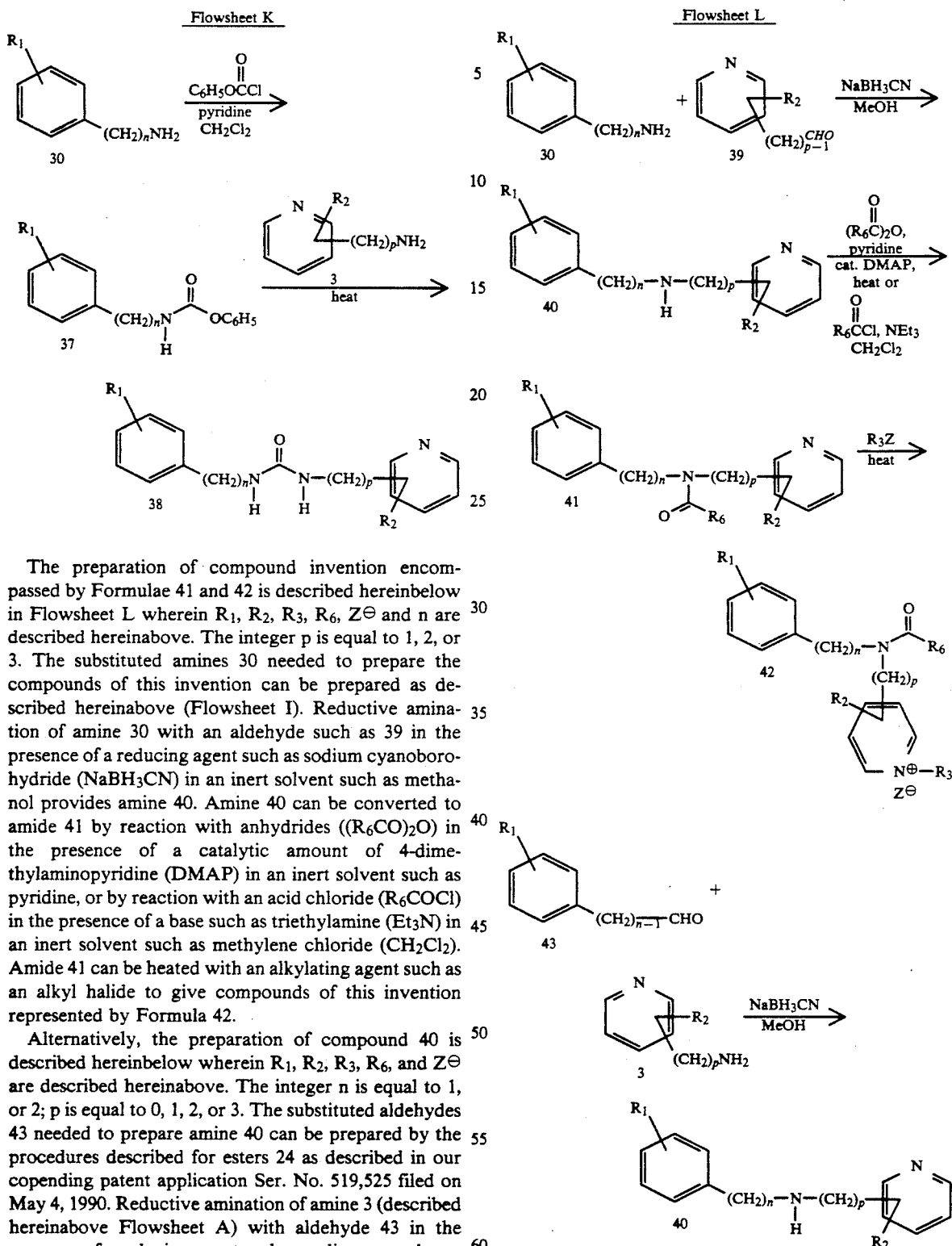

The preparation of compound invention encompassed by Formulae 41 and 42 is described hereinbelow in Flowsheet L wherein $R_1$, $R_2$, $R_3$, $R_6$, $Z^\ominus$ and n are described hereinabove. The integer p is equal to 1, 2, or 3. The substituted amines 30 needed to prepare the compounds of this invention can be prepared as described hereinabove (Flowsheet I). Reductive amination of amine 30 with an aldehyde such as 39 in the presence of a reducing agent such as sodium cyanoborohydride (NaBH$_3$CN) in an inert solvent such as methanol provides amine 40. Amine 40 can be converted to amide 41 by reaction with anhydrides (($R_6$CO)$_2$O) in the presence of a catalytic amount of 4-dimethylaminopyridine (DMAP) in an inert solvent such as pyridine, or by reaction with an acid chloride ($R_6$COCl) in the presence of a base such as triethylamine (Et$_3$N) in an inert solvent such as methylene chloride (CH$_2$Cl$_2$). Amide 41 can be heated with an alkylating agent such as an alkyl halide to give compounds of this invention represented by Formula 42.

Alternatively, the preparation of compound 40 is described hereinbelow wherein $R_1$, $R_2$, $R_3$, $R_6$, and $Z^\ominus$ are described hereinabove. The integer n is equal to 1, or 2; p is equal to 0, 1, 2, or 3. The substituted aldehydes 43 needed to prepare amine 40 can be prepared by the procedures described for esters 24 as described in our copending patent application Ser. No. 519,525 filed on May 4, 1990. Reductive amination of amine 3 (described hereinabove Flowsheet A) with aldehyde 43 in the presence of a reducing agent such as sodium cyanoborohydride (NaBH$_3$CN) in an inert solvent such as methanol provides amine 40.

A lead reference to the reductive amination of aldehydes and amines are Lane, C. F., *Synthesis*, 1975, 135; Borch, R. F.; Bernstein, M.D.; and Durst, H. D. *J. Am. Chem. Soc.*, 1971, 93, 2897; Borch, R.F.; and Hassid, A. I. *J. Org. Chem.*, 1972, 37, 1673.

The preparation of compound invention encompassed by Formulae 46 and 47 is described hereinbelow in Flowsheet M wherein $R_1$, $R_2$, $R_3$, $Z^\ominus$, n, and p are described hereinabove. The substituted acid chlorides 8 needed to prepare the compounds of this invention can be prepared as described hereinabove (Flowsheet C). Reaction of acid chloride 8 with aniline in the presence of a base, such as pyridine in an inert solvent such as methylene chloride (CH2Cl2) provides amide 44. Amide 44 can be converted to amine 45 by reduction with a reducing agent, such as lithium aluminum hydride (LiAlH4) in the presence of an inert solvent such as tetrahydrofuran. Amine 45 can be reacted with acid chloride 31 (described hereinabove in Flowsheet I) in the presence of a base such as triethylamine (NEt3) in an inert solvent such as methylene chloride (CH2Cl2) to provide amide 46. Amide 46 can be heated with an alkylating agent such as an alkyl halide to give compounds of this invention represented by Formula 47.

10–15 minutes at room temperature to recover the platelet rich plasma (PRP). Platelet poor plasma (PPP) is prepared by centrifuging PRP at 2800 rpm for 10 minutes at room temperature.

Dilutions (1:3000) of PRP in Isoton, diluent are made and platelet counts are determined on a Coulter Thrombocounter which is standardized with platelet reference standards (Interscience Platelet Control, Portland, OR). PRP platelet counts are adjusted to approximately 400,000–500,000 platelets/11 by the addition of PPP.

L-PAF (Platelet Activating Factor) is obtained from Calbiochem. A stock solution of 1-2 E-3M is prepared

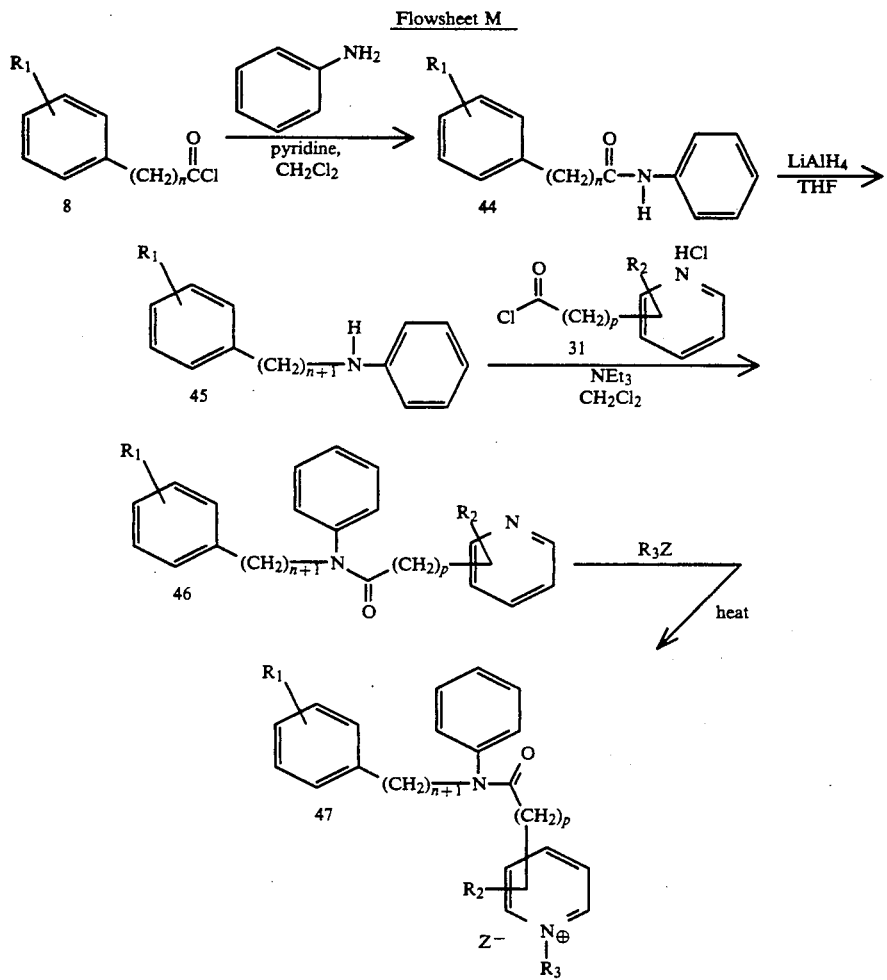

The compounds of this invention are tested for pharmacological activity as described in the following tests.

Platelet Activating Factor Antagonism In Vitro

Test compounds are evaluated as PAF receptor antagonists in vitro by measuring inhibition of PAF (platelet activating factor) induced platelet aggregation. Platelet aggregation is measured by a modification of the method described in A. Wissner, et. al., J. Med. Chem., 27 1174, 1984.

Approximately 120–240 ml of blood is collected by cardiac puncture from unanesthetized male New Zealand White rabbits (Whaley's Summit View Farms, Belvedere, NJ) with the use of 3.2% sodium citrate anticoagulant (1 part of citrate/10 parts of blood). All syringes and pipets are plastic. The blood is gently mixed and immediately centrifuged at 800 rpm for in 10% ethanol in water or 100% methanol and serial working dilutions are made using saline. 1-2 E-3M stock solutions of test compounds are prepared in 100% methanol and serially diluted in PBS. Sonication of samples before testing in biological screens assists in the solubility of compounds in the liquid medium. All solutions are made up in plastic tubes, stored on ice and protected from heat and light. Solutions are prepared fresh or frozen at −20° C. and used within 48 hours.

Incubation mixtures consisted of 400 ll PRP, 50 ll of saline diluent or test compound and 50 ll of PAF agonist. More specifically, 400 ll of PRP is stabilized in a cuvette for 1-2 minutes at 37° C. in the aggregometer to achieve a stable baseline, then 50 ll of saline or test compound is added and incubated for 5 minutes before addition of the challenge concentration of PAF. A submaximal concentration is determined from the dose response curve for PAF for that experiment. In general, the challenge concentration is 5E-8 or 1E-7M. Aggregation is monitored for 5 minutes. Samples containing test compound or diluent are run simultaneously for comparison. Test compounds are initially evaluated at a screening concentration of 1E-5M. Those producing ≧50% inhibition of the magnitude of aggregation at 1E-5M are then reevaluated at several final concentrations ranging from 1E-8M to 5E-5M and IC50 values are determined from the dose response curve.

The recording equipment consists of a dual channel Chronolog aggregometer connected to a dual channel 10 MV full scale deflection Omniscribe chart recorder (Houston Instruments). The chart recorder is calibrated daily with the use of a suspension of Bio-Rad latex beads (S-X 12 400 mesh) which has a density slightly greater than rabbit PRP. The bead suspension is used to set the 0% light transmission mark and clear water is used to set the 100% light transmission mark. These limits defined a full scale deflection. The aggregation traces are analyzed by a digitizing method (C. Kohler and B. Zoltan, J. Pharm. Methods, 12, 113, 1984) with x, y coordinate data stored in a computer file. A suitable program computes parameters of interest such as the magnitude of aggregation.

The results of tests on representative compounds of this invention appear in Table I.

TABLE I

In Vitro PAF Antagonism:
Inhibition of PAF Induced Platelet Aggregation
In Rabbit Platelet Rich Plasma

| Compound | Dose(M)$^a$ | % INH$^b$ | IC$_{50}$(M)$^c$ | PAF Chall Conc(M) |
|---|---|---|---|---|
| 1-Ethyl-2-[[[4-(tetradecyloxy)- | 1.00E − 05 | 0 | | 5.00E − 08 |
| benzoyl]amino]methyl]pyridinium iodide | 1.00E − 05 | 6 | | 5.00E − 08 |
| 1-Methyl-2-[[[4-(tetradecyloxy)- | 1.00E − 05 | 21 | | 5.00E − 08 |
| benzoyl]amino]methyl]pyridinium iodide | 1.00E − 05 | 5 | | 5.00E − 08 |
| 2-[[Acetyl[4-(tetradecyloxy)- | 1.00E − 05 | 0 | | 5.00E − 08 |
| benzoyl]amino]methyl]-1-methyl- | 1.00E − 05 | 97 | 7.00E − 07 | 5.00E − 08 |
| pyridinium iodide | 1.00E − 05 | 90 | 9.60E − 07 | 5.00E − 08 |
| | 1.00E − 05 | 0 | | 5.00E − 08 |
| | 1.00E − 05 | 36 | | 1.00E − 07 |
| | 1.00E − 05 | 96 | 1.30E − 06 | 5.00E − 08 |
| | 1.00E − 05 | 0 | | 1.00E − 07 |
| | 1.00E − 05 | 93 | 8.60E − 07 | 5.00E − 08 |
| 1-Ethyl-2-[[[[4-(hexadecyloxy)- | 1.00E − 05 | 52 | | 5.00E − 08 |
| phenoxy]acetyl]amino]methyl]- | 1.00E − 05 | 58 | 7.20E − 06 | 5.00E − 08 |
| pyridinium iodide | 1.00E − 05 | 74 | 5.60E − 06 | 5.00E − 08 |
| 1-Ethyl-2-[2-[[[4-(hexadecyloxy)- | 1.00E − 05 | 0 | | 5.00E − 08 |
| phenoxy]acetyl]amino]ethyl]- | 1.00E − 05 | 75 | 2.70E − 06 | 5.00E − 08 |
| pyridinium iodide | 1.00E − 05 | 90 | 3.20E − 06 | 5.00E − 08 |
| | 1.00E − 05 | 63 | 4.64E − 06 | 1.00E − 07 |
| 2-[[Acetyl[[4-(tetradecyloxy)- | 1.00E − 05 | 95 | 7.10E − 07 | 5.00E − 08 |
| phenyl]methyl]amino]methyl]-1- | 1.00E − 05 | 5 | | 1.00E − 07 |
| ethylpyridinium iodide | 1.00E − 05 | 47 | 1.30E − 05 | 1.00E − 07 |
| | 1.00E − 05 | 43 | 1.60E − 05 | 5.00E − 08 |
| | 1.00E − 05 | 28 | | 5.00E − 08 |
| | 1.00E − 05 | 5 | | 5.00E − 08 |
| 2-[[Acetyl[[4-(hexadecyloxy)- | 1.00E − 05 | 0 | | 5.00E − 08 |
| phenoxy]acetyl]amino]methyl]-1- | 5.00E − 04 | 70 | 2.80E − 04 | 5.00E − 08 |
| methylpyridinium iodide | | | | |
| 1-Methyl-2-[2-[[4-(tetradecyl- | 1.00E − 05 | 0 | | 5.00E − 08 |
| oxy)benzoyl]amino]ethyl]- | 1.00E − 04 | 97 | 1.40E − 05 | 1.00E − 08 |
| pyridinium iodide | | | | |
| 1-Methyl-2-[2-[[[4-(tetradecyl- | 1.00E − 05 | 0 | | 5.00E − 08 |
| oxy)phenyl]acetyl]amino]ethyl]- | 1.00E − 04 | 97 | 1.50E − 05 | 5.00E − 08 |
| pyridinium iodide | | | | |
| 2-[[(2-Methoxybenzoyl)[4-(tetra- | 1.00E − 05 | 0 | | 5.00E − 08 |
| decyloxy)benzoyl]amino]methyl]- | 1.00E − 05 | 0 | | 5.00E − 08 |
| 1-methylpyridinium iodide | 1.00E − 05 | 96 | 1.50E − 06 | 5.00E − 08 |
| | 5.00E − 05 | 0 | | 5.00E − 08 |
| 3-[[Acetyl[[4-(tetradecyloxy)- | 1.00E − 05 | 0 | | 5.00E − 08 |
| phenyl]methyl]amino]methyl]-1- | 1.00E − 04 | 89 | 1.40E − 05 | 1.00E − 08 |
| methylpyridinium iodide | 5.00E − 04 | 88 | 5.60E − 03 | 5.00E − 08 |
| 2-[[Acetyl[[3-(tetradecyloxy)- | 1.00E − 05 | 49 | 1.70E − 05 | 5.00E − 08 |
| phenyl]methyl]amino]methyl-1- | | | | |
| methylpyridinium iodide | | | | |
| 2-[[Acetyl[[2-(tetradecyloxy)- | 1.00E − 05 | 0 | | 5.00E − 08 |
| phenyl]methyl]amino]methyl]-1- | 1.00E − 04 | 92 | 4.30E − 05 | 5.00E − 08 |
| methylpyridinium iodide | | | | |
| 3-[[Acetyl[4-(tetradecyloxy)- | 1.00E − 05 | 62 | 6.80E − 06 | 5.00E − 08 |
| benzoyl]amino]methyl-1- | | | | |
| methylpyridinium iodide | | | | |
| 4-[[Acetyl[[4-(tetradecyloxy)- | 1.00E − 05 | 65 | 1.00E − 06 | 5.00E − 08 |
| phenyl]methyl]amino]methyl]-1- | | | | |
| methylpyridinium iodide | | | | |
| 2-[[Acetyl[3-(1,1-dimethylethyl)- | 1.00E − 05 | 87 | 2.15E − 08 | 5.00E − 08 |
| 4-(tetradecyloxy)benzoyl]amino]- | 1.00E − 05 | 95 | 1.41E − 08 | 1.00E − 07 |
| methyl]-1-methylpyridinium iodide | 1.00E − 05 | 93 | 3.60E − 08 | 1.00E − 07 |

TABLE I-continued

In Vitro PAF Antagonism:
Inhibition of PAF Induced Platelet Aggregation
In Rabbit Platelet Rich Plasma

| Compound | Dose(M)[a] | % INH[b] | IC$_{50}$(M)[c] | PAF Chall Conc(M) |
|---|---|---|---|---|
| 2-[[Acetyl[3-methoxy-4-(tetra-decyloxy)benzoyl]amino]methyl]-1-methylpyridinium iodide | 1.00E − 05 | 88 | 6.36E − 08 | 5.00E − 08 |
| | 1.00E − 05 | 92 | 4.43E − 06 | 1.00E − 07 |
| | 1.00E − 05 | 96 | 3.40E − 07 | 1.00E − 07 |
| | 1.00E − 05 | 82 | 2.30E − 06 | 1.00E − 07 |
| 2-[[Acetyl[4-methoxy-3-(tetra-decyloxy)benzoyl]amino]methyl]-1-methylpyridinium iodide | 1.00E − 05 | 34 | 1.60E − 04 | 5.00E − 08 |
| 1-Methyl-2-[[[(4-methylphenyl)-sulfonyl][[3-(tetradecyloxy)-phenyl]methyl]amino]methyl]-pyridinium iodide | 1.00E − 05 | 10 | | 5.00E − 08 |
| 2-[[Acetyl[[[4-(tetradecyloxy)-phenyl]methoxy]carbonyl]amino]-methyl]-1-methylpyridinium iodide | 1.00E − 05 | 0 | | 5.00E − 08 |
| | 1.00E − 05 | 6 | | 5.00E − 08 |
| 3-[[Acetyl[4-(tetradecyloxy)-phenyl]amino]methyl]-1-methylpyridinium iodide | 1.00E − 05 | 0 | | 1.00E − 07 |
| | 1.00E − 04 | 0 | | 5.00E − 08 |
| | 1.00E − 04 | 49 | 1.00E − 02 | 5.00E − 08 |
| N-Acetyl-3-(1,1-dimethylethyl)-N-(2-pyridinylmethyl)-4-(tetradecyloxy)benzamide N'-oxide | 1.00E − 05 | 20 | | 5.00E − 08 |
| 1-[[Acetyl[4-(tetradecyloxy)-benzoyl]amino]methyl]-1-(phenylmethyl)pyridinium bromide | 1.00E − 05 | 0 | | 5.00E − 08 |
| | 1.00E − 04 | 33 | 3.00E − 04 | 5.00E − 08 |
| 1-Methyl-3-[[[[4-(tetradecyl-oxy)phenyl]methyl]amino]carbonyl]pyridinium iodide | 1.00E − 05 | 0 | | 5.00E − 08 |
| | 1.00E − 04 | 38 | 1.20E − 04 | 5.00E − 08 |
| 1-Methyl-4-[[[[4-(tetradecyl-oxy)phenyl]methyl]amino]carbonyl]pyridinium iodide | 1.00E − 05 | 0 | | 5.00E − 08 |
| | 1.00E − 04 | 76 | 6.00E − 05 | 5.00E − 08 |
| 1-Methyl-2-[[(methylsulfonyl)-[[4-(tetradecyloxy)phenyl]-methyl]amino]methyl]pyridinium iodide | 1.00E − 05 | 15 | | 5.00E − 08 |
| | 1.00E − 05 | 0 | | 5.00E − 08 |
| 1-Methyl-2-[[(methylsulfonyl)-[4-(tetradecyloxy)benzoyl]amino]-methyl]pyridinium salt with tri-fluoromethanesulfonic acid (1:1) | 1.00E − 05 | 23 | | 5.00E − 08 |
| 1-Methyl-2-[[[3,4-bis(tetra-decyloxy)benzoyl]amino]methyl]-pyridinium iodide | 1.00E − 05 | 0 | | 5.00E − 08 |
| | 1.00E − 04 | 0 | | 5.00E − 08 |
| | 1.00E − 04 | 16 | 1.30 + 00 | 5.00E − 08 |
| 2-[[Acetyl[3,4-bis(tetradecyl-oxy)benzoyl]amino]methyl]-1-methylpyridinium iodide | 1.00E − 05 | 11 | | 5.00E − 08 |
| 2-[[Acetyl[3,4-bis(heptyloxy)-benzoyl]amino]methyl]-1-methyl-pyridinium iodide | 1.00E − 05 | 87 | 3.68E − 06 | 5.00E − 08 |
| 1-Methyl-3-[[phenyl[[4-(tetra-decyloxy)phenyl]methyl]amino]-carbonyl]pyridinium iodide | 1.00E − 05 | 15 | | 5.00E − 08 |
| 3-[[Phenyl[[4-(tetradecyloxy)-phenyl]methyl]amino]carbonyl]-1-propylpyridinium iodide | 1.00E − 05 | 12 | | 5.00E − 08 |
| 2-[[Acetyl[3-methoxy-4-(tetra-decyloxy)benzoyl]amino]methyl]-1-ethylpyridinium iodide | 1.00E − 05 | 95 | 7.03E − 08 | 5.00E − 08 |
| | 1.00E − 05 | 95 | 2.40E − 07 | 5.00E − 08 |
| 2-[[Acetyl[4-(decyloxy)-3-(1,1-dimethylethyl)benzoyl]amino]-methyl]-1-methylpyridinium iodide | 1.00E − 05 | 16 | | 5.00E − 08 |
| 3-[[Acetyl[3-(1,1-dimethyl-ethyl)-4-(tetradecyloxy)-benzoyl]amino]methyl]-1-methylpyridinium iodide | 1.00E − 05 | 46 | 2.00E − 05 | 5.00E − 08 |
| 4-[[Acetyl[3-(1,1-dimethyl-ethyl)-4-(tetradecyloxy)-benzoyl]amino]methyl]-1-ethylpyridinium iodide | 1.00E − 05 | 93 | 1.05E − 06 | 5.00E − 08 |

[a] dose of compound that gives in indicated % inhibition.
[b] the % inhibition of PAF induced platelet aggregation.
[c] the molar concentration of compound that will inhibit 50% of the platelet aggregation induced by PAF given at the indicated PAF challenge concentration.

PAF Induced Lethality in Mice

PAF given I.V. to mice causes an immediate hypotensive shock leading to death in 1 hour or less. Compounds are given intraperitoneally at ½ hour prior to the PAF challenge. Animals alive after 2 hours are counted and the activity of test compounds expressed as % survival corrected for any control (saline treated) animals which survived the PAF challenge. Results of this assay appear in Table II.

TABLE II
Effect of Compound Given IP in Protecting Mice from a Lethal Challenge of PAF$^a$

| Compound | Dose (IP) mg/kg | % Survival |
|---|---|---|
| 2-[[Acetyl[4-(tetradecyloxy)-benzoyl]amino]methyl]-1-methylpyridinium iodide | 0.5 | 27 |
| 2-[[Acetyl[[4-(tetradecyloxy)phenyl]methyl]amino]methyl]-1-ethylpyridinium iodide | | 40 |
| 3-[[Acetyl[[4-(tetradecyloxy)phenyl]methyl]amino]methyl]-1-methylpyridinium iodide | | 38 |
| 2-[[Acetyl[[2-(tetradecyloxy)phenyl]methyl]amino]methyl]-1-methylpyridinium iodide | | 23 |
| 2-[[Acetyl[3-(1,1-dimethylethyl)-4-(tetradecyloxy)benzoyl]amino]methyl]-1-methylpyridinium iodide | | 60 |
| 2-[[Acetyl[3-methoxy-4-(tetradecyloxy)benzoyl]amino]methyl]-1-methylpyridinium iodide | | 43 |
| 2-[[Acetyl[4-methoxy-3-(tetradecyloxy)benzoyl]amino]methyl]-1-methylpyridinium iodide | | 21 |
| 2-[[Acetyl[[[4-(tetradecyloxy)phenyl]methoxy]carbonyl]amino]methyl]-1-methylpyridinium iodide | | 40 |
| 3-[[Acetyl[4-(tetradecyloxy)phenyl]amino]methyl]-1-methylpyridinium iodide | | 7 |
| 2-[[Acetyl[4-(tetradecyloxy)benzoyl]amino]methyl]-1-(phenylmethyl)pyridinium bromide | | 0 |
| 1-Methyl-2-[[(methylsulfonyl)[[4-(tetradecyloxy)phenyl]methyl]amino]methyl]]pyridinium iodide | | 55 |
| 1-Methyl-2-[[(methylsulfonyl)[4-(tetradecyloxy)benzoyl]amino]methyl]pyridinium salt with trifluoromethanesulfonic acid (1:1) | | 88 |
| 1-Methyl-2-[[[3,4-bis(tetradecyloxy)benzoyl]amino]methyl]-pyridinium iodide | | 0 |
| 2-[[Acetyl[3,4-bis(tetradecyloxy)benzoyl]amino]methyl]-1-methyl-pyridinium iodide | | 36 |
| 2-[[Acetyl[3,4-bis(heptyloxy)benzoyl]amino]methyl]-1-methylpyridinium iodide | | 45 |
| 1-Methyl-3-[[phenyl[[4-(tetradecyloxy)phenyl]methyl]amino]carbonyl]pyridinium iodide | | 69 |
| 3-[[Phenyl[[4-(tetradecyloxy)phenyl]methyl]amino]carbonyl]-1-propylpyridinium iodide | | 64 |
| 2-[[Acetyl[3-methoxy-4-(tetradecyloxy)benzoyl]amino]methyl]-1-ethylpyridinium iodide | | 29 |
| Control (saline) | | 10 |

$^a$lethal challenge of PAF is 100–150 lg/kg

Endotoxin Induced Shock and Mortality in Mice

Endotoxin administration produces a shocklike state characterized by vascular permeability changes, hypotension, neutropenia, multiple organ damage and death. The major mediators released after endotoxin injection are TNF (tumor necrosis factor), PAF (platelet activating factor) and IL-1 (interleukin I). PAF administration mimics the signs and symptoms of endotoxin induced shock and death and endotoxin also induces the release of PAF. Therefore, the effects of endotoxin should be blocked with a PAF antagonist.

Male Balb/c mice (approximately 20 g) are obtained from Charles River Laboratories and used after a three-week acclimation period. Animals are given (ip) test compound dissolved in saline or water (sonicated and heated) at different time intervals prior to and after the ip injection of endotoxin (usually 2 hours before LPS endotoxin, and 3–4 hours after). Sigma E. Coli endotoxin, 0111:B4, phenol extraction, catalog #L2630 is used for these studies.

For the acute lethality test, the endotoxin dose is determined from dose-response titrations and adjusted to a dose that is lethal for 80–90% ($LD_{80}$–$LD_{90}$) of the mice within a 24 hour period. This LD value is approximately 50 mg/kg i.p. The number of survivors in each group (control or treated with test compound) is recorded after 24 hours and the treated groups (receiving test compound and endotoxin) are compared with the untreated, control group (receiving endotoxin only) or saline control (receiving saline and endotoxin). (Table III)

TABLE III
Effects of Compounds Given IP in High Dose Acute Mouse Endotoxemia

| Compounds | Dose mg/kg | # of Survivors out of 15 Drug Treated | Control |
|---|---|---|---|
| 2-[[Acetyl[4-(tetradecyloxy)benzoyl]amino]methyl]-1-methylpyridinium iodide | 20 | 14 | 8 |
| | 10 | 8 | 5 |
| | 10 | 8 | 3 |
| | 40 | 11 | 3 |
| | 40 | 11 | 6 |
| | 20 | 14 | 2 |
| 2-[[Acetyl[3-(1,1-dimethylethyl)-4-(tetradecyloxy)benzoyl]amino]methyl]-1-methylpyridinium iodide | 40 | 3 | 4 |
| | 40 | 1 | 1 |
| | 20 | 5 | 2 |
| | 40 | 0 | 6 |
| | 20 | 11 | 4 |
| | 20 | 9 | 1 |
| | 20 | 3 | 5 |
| 2-[[Acetyl[3-methoxy-4-(tetradecyloxy)benzoyl]amino]methyl]-1-methylpyridinium iodide | 20 | 3 | 5 |
| | 40 | 7 | 1 |
| | 20 | 9 | 2 |
| | 20 | 4 | 1 |
| | 40 | 8 | 4 |
| | 40 | 10 | 6 |
| | 20 | 9 | 4 |
| 2-[[Acetyl[[[4-(tetradecyloxy)phenyl]methoxy]carbonyl]amino]methyl]-1-methylpyridinium iodide | 20 | 2 | 2 |
| | 20 | 7 | 4 |
| | 40 | 5 | 3 |
| | 20 | 5 | 1 |
| | 40 | 11 | 6 |
| | 40 | 14 | 4 |
| | 20 | 1 | 5 |
| | 40 | 8 | 0 |
| 1-Methyl-2-[[(methylsulfonyl)[4-(tetradecyloxy)benzoyl]amino]methyl]pyridinium salt with trifluoromethanesulfonic acid (1:1) | 20 | 2 | 1 |
| | 40 | 9 | 3 |
| | 40 | 3 | 0 |
| | 20 | 4 | 3 |
| 1-Methyl-3-[[phenyl[[4-(tetradecyloxy)phenyl]methyl]amino]carbonyl]pyridinium iodide | 20 | 5 | 1 |
| | 20 | 6 | 0 |
| | 40 | 7 | 4 |
| | 40 | 11 | 1 |
| | 40 | 10 | 2 |
| | 40 | 10 | 4 |
| 3-[[Phenyl[[4-(tetradecyloxy)phenyl]methyl]- | 20 | 7 | 1 |
| | 20 | 9 | 0 |

TABLE III-continued

Effects of Compounds Given IP in High Dose Acute Mouse Endotoxemia

| Compounds | Dose mg/kg | # of Survivors out of 15 | |
|---|---|---|---|
| | | Drug Treated | Control |
| amino]carbonyl]-1-pro- | 40 | 9 | 2 |
| pylpyridinium iodide | 40 | 11 | 1 |
| | 40 | 9 | 4 |
| 2-[[Acetyl[4-(decyloxy)- | 40 | 0 | 3 |
| 3-(1,1-dimethylethyl)- | 20 | 0 | 2 |
| benzoyl]amino]methyl]- | 20 | 0 | 2 |
| 1-methylpyridinium iodide | 40 | 0 | 3 |

LPS Endotoxin Challenge = 50 mg/kg IP

In addition to the utilities described hereinabove, many of the compounds of this invention are useful in the preparation of other compounds of this invention.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to this invention are prepared so that an oral dosage unit contains between about 1 and 250 mg of active compound.

The tablets, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to active ingredient, sucrose as a sweetening agent, methyl and propylparabens as preservatives, a dye and flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersions medium containing, for example, water, ethanol, polyol (e.g., glycerol, propylene glycol and liquid polyethylene glycol), suitable mixtures thereof, and vegetable oils.

The compounds of this invention may also be administered directly to the airways in the form of an aerosol.

The invention will be further described by the following examples.

EXAMPLE 1

4-(Tetradecyloxy)benzoic acid methyl ester

A mixture of 150 g methyl-4-hydroxybenzoate, 1.5 L 2-butanone, 272.5 g potassium carbonate and 293 ml 1-bromotetradecane is heated at reflux for 66 hours. The reaction is cooled to room temperature, filtered, the filtrate concentrated in vacuo and the residue recrystallized from methylene chloride/hexane to give 258.8 g of the desired product. MP 56°-58° C.

EXAMPLE 2

4-(Tetradecyloxy)benzoic acid

To 20 g of product from Example 1 is added 9.66 g potassium hydroxide, 160 ml methyl alcohol, 10 ml water and 70 ml ethyl alcohol. The reaction mixture is refluxed for 6.5 hours, during which time an additional 100 ml methyl alcohol and 100 ml water is added. To the cooled reaction mixture is added 1 L of methylene chloride and sufficient concentrated hydrochloric acid to make the reaction pH acidic. The white crystals are collected and dried in vacuo over phosphorus pentoxide to give 19.0 g of the desired product. MP 94°-96° C.

EXAMPLE 3

4-(Tetradecyloxy)benzoyl chloride

To a room temperature suspension of 15 g of product from Example 2, 160 ml methylene chloride and 5 drops dimethylformamide is added 5.87 ml oxalyl chloride. The reaction mixture is stirred at room temperature for 18 hours, concentrated in vacuo, dissolved in 300 ml of diethyl ether, filtered through diatomaceous earth and the filtrate concentrated in vacuo to give 15.5 g of the desired product.

Analysis Calc'd C: 71.46; H:9.42; Cl:10.04; Found C: 71.53; H:9.55; Cl:10.10.

EXAMPLE 4

N-(2-Pyridinylmethyl)-4-(tetradecyloxy)benzamide

To a 0° C. solution of 0.674 g 2-(aminomethyl)pyridine, 20 ml methylene chloride and 1.83 ml pyridine is added, dropwise over 20 minutes, 2.0 g of product from Example 3 dissolved in 25 ml of methylene chloride. The reaction is stirred at 0° C. for 2 hours followed by stirring at room temperature for 17 hours. The reaction mixture is partitioned between chloroform and saturated sodium bicarbonate, washed with water and saturated sodium chloride, dried and concentrated in vacuo. The residue is purified by column chromatography (silica gel:75% ethyl acetate/hexane) to give 1.51 g of the desired product.

MP 91°-93° C.

An alternative method of preparing the title compound is described below (Journal of Organic Chemistry, 1963, 28, 2915).

A mixture of 5.0 g of product from Example 1, 1.63 ml of 2-(aminomethyl)pyridine, 0.853 g of sodium methoxide and 35 ml of benzene is heated at reflux temperature for 24 hours. A Dean-Stark trap is used to remove the resulting methyl alcohol and water. The cooled solution is diluted with chloroform, washed with water and saturated sodium chloride, dried and concentrated in vacuo. The residue is purified by column chromatography (silica gel:60% ethyl acetate/hexane) to give 1.60 g of the desired product.

EXAMPLE 5

N-Acetyl-N-(2-pyridinylmethyl)-4-(tetradecyloxy)benzamide

A mixture of 2.0 g of product from Example 4, 8.9 ml acetic anhydride, 0.0863 g 4-dimethylaminopyridine and 30 ml pyridine is heated at reflux temperature for 23 hours, cooled, poured into 150 ml of water and extracted with methylene chloride. The organic layer is washed with saturated sodium chloride, dried and concentrated in vacuo. The residue is purified by column chromatogaphy (silica gel: 15-20% ethyl acetate/hexane) to give 1.4 g of the desired product as light yellow crystals.

MP 68°-70° C.

EI-MS: m/z 466(M+).

An alternative method of preparing the title compound is described below.

To a room temperature mixture of 2.17 g of washed 50% sodium hydride in 40 ml of dry tetrahydrofuran is added, via cannula, 6.79 g of product from Example 12 in 60 ml of dry tetrahydrofuran. The mixture is stirred at room temperature for 30 minutes followed by heating at 45° C. for 30 minutes. The reaction is cooled to room temperature and 15.2 g of product from Example 3 in 60 ml dry tetrahydrofuran is added, via cannula. The reaction is stirred at room temperature for 30 minutes, heated at 45° C. for 2 hours and stirred at room temperature for 16 hours. The reaction is poured into a 50% solution of sodium chloride and extracted with methylene chloride. The methylene chloride extract is washed with saturated sodium chloride, dried and concentrated in vacuo. The residue is purified by column chromatography (silica gel: 25% ethyl acetate/hexane) to give 10.30 g of the desired product.

EXAMPLE 6

2-Methoxy-N-(2-pyridinylmethyl)-N-[4-(tetradecyloxy)benzoyl]benzamide

To a solution of 1 g of product from Example 4 in 15 ml of dry tetrahydrofuran is added in one portion 0.0622 g of sodium hydride. The mixture is heated at reflux temperature for 2 hours, cooled to room temperature and 0.442 g o-anisoyl chloride is added. The reaction is then heated at reflux for 1.5 hours, cooled to room temperature, poured into water and extracted with ethyl acetate. The organic layer is washed with saturated sodium chloride, dried and concentrated in vacuo. The residue is purified by column chromatography (silica gel: 35% ethyl acetate/hexane) to give 1.27 g of the desired product.

EI-MS: m/z 558 (M+).

EXAMPLE 7

2-[[(2-Methoxybenzoyl)[4-(tetradecyloxy)benzoyl]amino]methyl]-1-methylpyridinium iodide A mixture of 0.770 g of product from Example 6 and 4.29 ml methyl iodide is heated in a sealed tube at 105° C. for 15 hours. The cooled reaction is concentrated in vacuo to give 0.960 g of the desired product as a thick yellow oil which solidified on standing.

MP 82°-83° C.

MS(FAB): 573 (M+-I).

EXAMPLE 8

2-[[Acetyl[4-(tetradecyloxy)benzoyl]amino]methyl]-1-methylpyridinium iodide

A mixture of 0.808 g of product from Example 5 and 5.39 ml of methyl iodide is heated, in a sealed dark tube, at 115° C. for 23 hours. The cooled reaction mixture is concentrated in vacuo and the residue purified by column chromatography (silica gel: 20% methyl alcohol/chloroform) to give 0.63 g of the desired product as cream crystals.

MP 84°-88° C.

MS(FAB): 481 (M+-I).

EXAMPLE 9

2-[[Acetyl[4-(tetradecyloxy)benzoyl]amino]methyl]-1-(phenylmethyl)pyridinium bromide A mixture of 0.75 g of product from Example 5, 0.412 g of benzyl bromide and 3 ml of acetonitrile is stirred at room temperature for 17.5 hours then heated, in a sealed tube, at 100° C. for 21.25 hours. The cooled reaction mixture is concentrated in vacuo and the residue purified by column chromatography (silica gel: 10% methyl alcohol/chloroform) to give 0.515 g of the desired product.

MB(FAB): 557 (M+-Br)

EXAMPLE 10

1-Ethyl-2-[[[4-(tetradecyloxy)benzoyl]amino]methyl]pyridinium iodide

A mixture of 1.0 g of product from Example 4 and 9.42 ml of ethyl iodide is heated, in a sealed dark tube, at 140° C. for 20 hours. The cooled reaction mixture is concentrated in vacuo, the residue purified by column chromatography (silica gel:10% methyl alcohol/chloroform) and recrystallized from 5% chloroform/methyl alcohol to give 0.96 g of the desired product.

MP 129°-130° C.

MS(FAB):453 (M+-I).

EXAMPLE 11

1-Methyl-2-[[[4-(tetradecyloxy)benzoyl]amino]methyl]pyridinium iodide

A mixture of 1.0 g of product from Example 4 and 7.33 ml of methyl iodide is heated, in a dark sealed tube, at 100°-120° C. for 22 hours. The cooled reaction mixture is concentrated in vacuo and recrystallized 2 times from methyl alcohol to give 1.15 g of the desired product as light yellow microneedles.

MP 108°-110° C.

MS(FAB): 439 (M+-I).

EXAMPLE 12

N-2-Pyridylmethylacetamide

A mixture of 5.0 g 2-(aminomethyl)pyridine, 5.02 ml acetic anhydride, 0.847 g 4-dimethylaminopyridine and 35 ml of pyridine is heated at reflux temperature for 23.5 hours. The cooled solution is poured into water and extracted with methylene chloride. The organic layer is washed with saturated sodium chloride, dried and concentrated in vacuo. The residue is purified by column chromatography (silica gel:5% methyl alcohol/ethyl acetate) to give 3.3 g of desired product as a light yellow oil.

EI-MS:m/z 150 (M+).

EXAMPLE 13

N-[2-(2-Pyridinyl)ethyl]acetamide

The title compound is prepared by the procedure of Example 12 using 25 g of 2-(2-aminoethyl)pyridine, 22.2 ml of acetic anhydride, 2.57 g of 4-dimethylaminopyridine and 100 ml of pyridine. The residue is purified by column chromatography (silica gel:20% methyl alcohol/ethyl acetate) to give 7.5 g of desired product as a yellow oil.

MS:m/z 164 (M+).

EXAMPLE 14

N-(3-Pyridinylmethyl)acetamide

The title compound is prepared by the procedure of Example 12 using 50 g of 3-(aminomethyl)pyridine, 50.2 ml of acetic anhydride, 2.26 g of 4-dimethylaminopyridine and 150 ml of pyridine without heating at reflux. The residue is purified by column chromatography (silica gel:20% methyl alcohol/ethyl acetate) to give 31.8 g of the desired product as a yellow oil.

EI-MS:m/z 150 (M+).

EXAMPLE 15

N-(4-Pyridinylmethyl)acetamide

The title compound is prepared by the procedure of Example 12 using 25 g of 4-(aminomethyl)pyridine, 25.1 ml of acetic anhydride, 2.26 g of 4-dimethylaminopyridine, 80 ml of pyridine and stirring at room temperature for 68 hours. The residue is purified by column chromatography (silica gel:20% methyl alcohol/ethyl acetate) to give 3.82 g of desired product as orange crystals.

MP 76°-78° C.
EI-MS:m/z 150 (M+).

EXAMPLE 16

4-(Tetradecyloxy)phenol

To a room temperature mixture of 40 g of hydroquinone, 62.76 g potassium carbonate, 3.02 g potassium iodide and 700 ml acetone is added, dropwise, 113.5 ml of 1-bromotetradecane. The reaction is heated at reflux temperature for 20 hours, cooled, filtered and concentrated in vacuo. The residue is purified by column chromatography (silica gel:0–10% ethyl acetate/hexane) to give 36.5 g of the desired product as colorless crystals.

MP 81°-82° C.

EXAMPLE 17

2-(Tetradecyloxy)benzoic acid methyl ester

A mixture of 40 g of methyl 2-hydroxybenzoate, 45.4 g of powdered potassium carbonate, 700 ml acetone and 78.2 g of 1-bromotetradecane is heated at reflux temperature for 5 days. The reaction is cooled, filtered and concentrated in vacuo. The residue is dissolved in ethyl acetate; washed with water, saturated sodium bicarbonate, 10% sodium hydroxide, water and saturated sodium chloride; dried and concentrated in vacuo. The residue is purified by column chromatography (silica gel:0–10% ethyl acetate/hexane) to give 46.0 g of the desired product.

MP 39°-40° C.
EI-MS:m/z 348 (M+).

EXAMPLE 18

N,N-Diethyl-2-(tetradecyloxy)benzamide

A mixture of 25 g of N,N-diethylsalicylamide, 38.5 ml of 1-bromotetradecane, 22.35 g of potassium carbonate and 400 ml of 2-butanone is heated at reflux temperature for 16 hours. The reaction is cooled, filtered and concentrated in vacuo. The concentrate is dissolved in chloroform, dried and concentrated in vacuo. The residue is purified by column chromatography (silica gel:- 0–30% ethyl acetate/hexane) to give 42.5 g of the desired product as colorless crystals.

MP 31°-32° C.
EI-MS:m/z 390 (M+).

EXAMPLE 19

4-(Tetradecyloxy)benzyl alcohol

To a room temperature solution of 3.27 g lithium aluminum hydride in 80 ml of dry tetrahydrofuran is added, dropwise, 10 g of product from Example 1 in 70 ml of dry tetrahydrofuran. The reaction is stirred at room temperature for 5½ hours, quenched with a saturated sodium sulfate solution, filtered and the filtrate concentrated in vacuo. The residue is purified by column chromatography (silica gel:20% ethyl acetate/hexane) to give 9.0 g of desired product as colorless needles.

MP 72°-74° C.
EI-MS:m/z 320 (M+).

EXAMPLE 20

1-(Bromomethyl)-4-(tetradecyloxy)benzene

To a room temperature slurry of 2.5 g of product from Example 19, 10 ml of acetonitrile and 0.339 g of pyridine is added dropwise, over 3 minutes, 2.11 g of phosphorus tribromide. The reaction is stirred at room temperature for 1 hour, diluted with methylene chloride and concentrated in vacuo. The residue is dissolved in methylene chloride, filtered through a silica gel pad and concentrated in vacuo to give 2.65 g of the desired product as pale yellow crystals.

MP 40°-41° C.

EXAMPLE 21

2-(Tetradecyloxy)benzenemethanol

The title compound is prepared by the procedure of Example 19 using 20.0 g of product from Example 17, 200 ml of dry tetrahydrofuran and 6.53 g of lithium aluminum hydride. The reaction is stirred at room temperature for 60 hours. The product, 18.4 g, is obtained as colorless crystals.

MP 33°-34° C.
EI-MS:m/z 320 (M+).

EXAMPLE 22

1-(Bromomethyl)-2-(tetradecyloxy)benzene

The title compound is prepared by the procedure of Example 20 using 2.5 g of product from Example 21, 10 ml acetonitrile, 2.11 g of phosphorus tribromide and 0.339 g of pyridine. The reaction is cooled for 10 minutes at 0° C., followed by stirring at room temperature for 1 hour. The product, 2.58 g, is obtained as cream crystals.
MP 35°-36° C.
EI-MS:m/z 382/384 (M+).

EXAMPLE 23

3-(Tetradecyloxy)benzoic acid

The title compound is prepared by the procedure of Example 2 using 234 g of 3-(tetradecyloxy)benzoic acid methyl ester, 113.0 g of potassium hydroxide, 1 L of methyl alcohol and 120 ml of water. The solid residue is recrystallized from methyl alcohol/ethyl alcohol to give 209 g of the desired product.
MP 90°-91° C.
EI-MS: m/z 334 (M+).

EXAMPLE 24

3-(Tetradecyloxy)benzenemethanol

The title compound is prepared by the procedure of Example 21 using 20.0 g of product from Example 23, 200 ml of dry tetrahydrofuran and 7.94 g of lithium aluminum hydride. The product, 18.82 g, is obtained as colorless crystals.
MP 49°-50° C.
EI-MS:m/z 320 (M+).

EXAMPLE 25

1-(Bromomethyl)-3-(tetradecyloxy)benzene

The title compound is prepared by the procedure of Example 20 using 2.5 g of product from Example 24, 10 ml acetonitrile, 0.339 g of pyridine and 2.11 g of phosphorus tribromide. The product, 2.27 g, is obtained as colorless needles.
MP 34°-35° C.
EI-MS:m/z 382/384 (M+).

EXAMPLE 26

3-(Tetradecyloxy)benzoyl chloride

To a suspension of 5.0 g of product from Example 23, 0.055 g of dimethylformamide and 70 ml of methylene chloride is added 1.96 ml of oxalyl chloride. The reaction is stirred at room temperature for 22 hours and concentrated. The residue is dissolved in diethyl ether, filtered and concentrated to give 5.28 g of the desired product as cream crystals.
MP 26°-27° C.

EXAMPLE 27

N-Acetyl-N-(3-pyridinylmethyl)-4-(tetradecyloxy)benzamide

To a room temperature suspension of 0.148 g of 50% washed sodium hydride in 4 ml of dry tetrahydrofuran is added 0.462 g of product from Example 14. The mixture is stirred at room temperature for 2.5 hours and 1.04 g of product from Example 3 in 4 ml of dry tetrahydrofuran is added. The reaction is stirred at room temperature for 2 hours followed by gentle refluxing for 18.5 hours. The cooled reaction is poured into water and extracted with methylene chloride. The organic layer is washed with saturated sodium chloride, filtered and concentrated in vacuo. The residue is purified by column chromatography (silica gel: 50% ethyl acetate/hexane) to give 0.384 g of the desired product as cream crystals.
MP 46°-48° C.
EI-MS:m/z 466 (M+).

EXAMPLE 28

3-[[Acetyl[4-(tetradecyloxy)benzoyl]amino]methyl]-1-methylpyridinium iodide

A mixture of 0.281 g of product from Example 27 and 1.88 ml of methyl iodide is heated in a sealed tube at 110° C. for 20 hours. The cooled solution is concentrated in vacuo and the residue recrystallized from methyl alcohol to give 0.367 g of the desired product as cream crystals.
MP 65°-66° C.
MS (FAB): 439.

EXAMPLE 29

N-Acetyl-N-(2-pyridinylmethyl)-3-(tetradecyloxy)benzamide

The title compound prepared by the procedure of Example 27 using 0.462 g of product from Example 12 in 4 ml of dry tetrahydrofuran, 0.147 g of washed 50% sodium hydride and 1.03 g of product from Example 26 in 4 ml of dry tetrahydrofuran. The residue is purified by column chromatography (silica gel: 35% ethyl acetate/hexane) to give 0.178 g of the desired product as a yellow oil which crystallized on standing.
MP 66°-67° C.
EI-MS: m/z 466 (M+).

EXAMPLE 30

2-[[Acetyl[3-(tetradecyloxy)benzoyl]amino]methyl]-1-methylpyridinium iodide

The title compound is prepared by the procedure of Example 28, using 1.08 g of product from Example 29 and 16.36 g of methyl iodide. The residue is recrystallized from methyl alcohol to give 1.38 g of the desired product as yellow crystals with hygroscopic properties.
MS (FAB): 481 (M+-I-).

EXAMPLE 31

3-(1,1-Dimethylethyl)-4-(tetradecyloxy)benzoic acid methyl ester

A mixture of 30.0 g 3-(1,1-dimethylethyl)-4-hydroxybenzoic acid methyl ester, 42.9 ml of 1-bromotetradecane, 47.8 g of potassium carbonate and 700 ml of acetone is refluxed for 48 hours. The cooled reaction is filtered, concentrated in vacuo and purified by column chromatography (silica gel:0-3% ethyl acetate/hexane) to give 38.8 g of the desired product as colorless prisms.
MP 44°-45° C.
EI-MS:m/z 404 (M+).

EXAMPLE 32

3-(1,1-Dimethylethyl)-4-(tetradecyloxy)benzoic acid

A solution of 36.2 g of product from Example 31 in 320 ml of methyl alcohol, 125 ml ethyl alcohol, 20 ml of water and 15 g of potassium hydroxide is mechanically stirred at reflux temperature for 4 ½ hours. The reaction is cooled and 325 ml of 1N hydrochloric acid and 200 ml of chloroform is added. The mixture is heated until homogeneous, the layers are separated and extracted with chloroform. The combined organic layers are washed with 1N hydrochloric acid, dried and concentrated in vacuo. The residue is recrystallized from chloroform/hexane to give 31 g of the product as white crystals.

MP 121°–123° C.
EI-MS:m/z 375 (M+-CH$_3$).

EXAMPLE 33

3-(1,1-Dimethylethyl)-4-(tetradecyloxy)benzoyl chloride

To a solution of 30.0 g of product from Example 32 in 300 ml of methylene chloride and 10 drops of dimethylformamide is added, dropwise, 14.62 g of oxalyl chloride. The reaction is stirred at room temperature for 18 hours and concentrated in vacuo. The residue is dissolved in diethyl ether, filtered through diatomaceous earth and concentrated to give 3.12 g of the desired product as yellow crystals.

| Analysis | Calc'd | $C_{25}H_{41}ClO_2$: | Found: |
|---|---|---|---|
| | C,73.40;H,10.10;Cl,8.66; | | C,72.91;H,10.15;Cl,8.51. |

EXAMPLE 34

N-Acetyl-3-(1,1-Dimethylethyl)-4-(tetradecyloxy)-N-(2-pyridinylmethyl)benzamide

The title compound is prepared by the procedure of Example 27 using 9.7 g of product from Example 33, 3.74 g of product from Example 12, 1.2 g of washed 50% sodium hydride and 100 ml of tetrahydrofuran. The residue is purified by column chromatography (silica gel:30% ethyl acetate/hexane) to give 6.43 g of the desired product as colorless crystals.

MP 51°–52° C.
EI-MS:m/z 522 (M+).

EXAMPLE 35

2-[[Acetyl[3-(1,1-dimethylethyl)-4-(tetradecyloxy)benzoyl]amino]methyl]-1-methylpyridinium iodide The title compound is prepared by the procedure of Example 28 using 0.256 g of product from Example 34 and 1.52 ml of methyl iodide. The residue is recrystallized from methyl alcohol to give 0.315 g of the desired product as yellow crystals.

MP 44°–52° C.
MS(FAB): 537 (M+-I).

EXAMPLE 36

3-Chloro-4-(tetradecyloxy)benzoic acid methyl ester

A mixture of 100.0 g of 3-chloro-4-(hydroxy)benzoic acid methyl ester, 148.6 g of 1-bromotetradecane, 170.4 g of potassium carbonate and 1 L of acetone is heated at reflux temperature for 40.5 hours. The cooled reaction is filtered, concentrated in vacuo and purified by column chromatography (silica gel:0–2% ethyl acetate/hexane) to give 197.1 g of the desired product as colorless crystals.

MP 42°–43° C.
EI-MS:m/z 384, 382 (M+).

EXAMPLE 37

3-Chloro-4-(tetradecyloxy)benzoic acid

The title compound is prepared by the procedure of Example 32 using 125.0 g of product from Example 36 in 1 L of methyl alcohol, 60 ml of water, 400 ml of ethyl alcohol and 54.94 g of potassium hydroxide. The residue is recrystallized from chloroform/hexane to give 109 g of the desired product as white crystals.

MP 105°–106° C.
EI-MS:m/z 368 (M+).

EXAMPLE 38

3-Chloro-4-(tetradecyloxy)benzoyl chloride

To a mixture of 50.0 g of product from Example 37 in 700 ml of chloroform and 10 drops of dimethylformamide is added, dropwise, 25.8 g of oxalyl chloride. The reaction is stirred at room temperature for 18 hours and concentrated in vacuo. The residue is dissolved in diethyl ether, filtered and concentrated in vacuo to give 51.1 g of the desired product as white crystals.

MP 90° C.
EI-MS:m/z 387 (M+).

EXAMPLE 39

N-Acetyl-3-chloro-4-(tetradecyloxy)-N-(2-pyridinylmethyl)benzamide

The title compound is prepared by the procedure of Example 27 using 1.31 g of product from Example 38, 0.535 g of product from Example 12, 0.171 g of washed 50% sodium hydride and 12 ml of tetrahydrofuran. The residue is purified by column chromatography (silica gel:35% ethyl acetate/hexane) to give 0.067 g of product as a yellow oil.

EI-MS:m/z 501 (M+).

EXAMPLE 40

3-Hydroxy-4-methoxybenzoic acid methyl ester

A mixture of 50.0 g of 3-hydroxy-4-methoxybenzoic acid in 500 ml of absolute methyl alcohol containing 2.5 ml of concentrated sulfuric acid, is heated at reflux temperature for 6 hours. The reaction is concentrated in vacuo, 250 ml of ice water is added and the residue is extracted with diethyl ether. The organic layers are washed with saturated sodium bicarbonate and saturated sodium chloride, dried and concentrated in vacuo. The residue is dissolved in diethyl ether, passed through a pad of silica gel and concentrated in vacuo. The solid is recrystallized from diethyl ether/hexane to give 33 g of the desired product as white crystals.

MP 62°–63° C.
EI-MS:m/z 182 (M+)

EXAMPLE 41

4-Methoxy-3-(tetradecyloxy)benzoic acid methyl ester

A mixture of 45 g of product from Example 40, 51.2 g of finely powdered potassium carbonate, 72 g of 1-bromotetradecane, 1.9 g of sodium iodide and 500 ml of 2-butanone is heated at reflux temperature for 18 hours under an atmosphere of argon. The reaction is cooled and filtered. The filtrate is concentrated in vacuo and the residue is dissolved in chloroform. The organic layer is washed with 1N sodium hydroxide and saturated sodium chloride, dried and concentrated in vacuo. The residue is recrystallized from hexane to give 66.4 g of the desired product as white crystals.

MP 77°–79° C.
EI-MS:m/z 378 (M+).

EXAMPLE 42

4-Methoxy-3-(tetradecyloxy)benzoic acid

The title compound is prepared by the procedure of Example 32 using 60 g of product from Example 41, 480 ml methyl alcohol, 190 ml of ethyl alcohol, 28.5 ml of water and 26.7 g of potassium hydroxide. The residue is recrystallized from chloroform/hexane to give 47 g of the desired product as white crystals.
MP 110°–111° C.
EI-MS:m/z 364 (M+).

EXAMPLE 43

4-Methoxy-3-(tetradecyloxy)benzoyl chloride

To a mixture of 50 g of product from Example 42 in 500 ml of methylene chloride and 15 drops of dimethylformamide is added, dropwise, 26.12 g of oxalyl chloride. The reaction is stirred at room temperature for 18 hours and concentrated in vacuo. The residue is recrystallized from diethyl ether to give 52.3 g of the desired product as white crystals.
MP 60°–61° C.
Analysis Calc'd for $C_{22}H_{35}Cl$ $O_3$:C,68.99;H,9.21;Cl,9.25 ; Found: C,68.87;H,9.31;Cl,9.22.

EXAMPLE 44

N-Acetyl-4-methoxy-3-(tetradecyloxy)-N-(2-pyridinylmethyl)benzamide

The title compound is prepared by the procedure of Example 27 using 1.19 g of product from Example 43, 0.490 g of product from Example 12, 0.157 g of washed 50% sodium hydride and 12 ml of tetrahydrofuran. The residue is purified by column chromatography (silica gel:35% ethyl acetate/hexane) to give 0.472 g of the desired product as yellow crystals.
MP 77°–78° C.
EI-MS:m/z 496 (M+).

EXAMPLE 45

2-[[Acetyl[4-methoxy-3-(tetradecyloxy)benzoyl]amino]methyl]-1-methylpyridinium iodide The title compound is prepared by the procedure of Example 28 using 0.421 g of product from Example 44 and 2.64 ml of methyl iodide. The residue is recrystallized from methyl alcohol to give 0.541 g of the desired product as yellow crystals.
MP 128°–132° C. with decomposition
MS (FAB): 511 (M+-I).

EXAMPLE 46

3-Methoxy-4-(tetradecyloxy)benzoic acid methyl ester

A mixture of 28.5 g 3-methoxy-4-(hydroxy)benzoic acid methyl ester, 25.94 g of finely powdered potassium carbonate, 0.070 g potassium iodide and 285 ml of 2-butanone is heated at reflux temperature for 41 hours. The reaction is cooled and filtered. The filtrate is concentrated in vacuo and recrystallized from hexane to give 40.8 g of the desired product as white crystals.
MP 50°–51° C.
MS(FAB): 379 (M++H)

EXAMPLE 47

3-Methoxy-4-(tetradecyloxy)benzoic acid

The title compound is prepared by the procedure of Example 32 using 40 g of the product from Example 46, 320 ml of methyl alcohol, 125 ml ethyl alcohol, 20 ml of water and 17.8 g of potassium hydroxide. The residue is recrystallized from chloroform/hexane to give 32 g of the desired product as white crystals.
MP 107°–108° C.

EXAMPLE 48

3-Methoxy-4-(tetradecyloxy)benzoyl chloride

To a mixture of 30.0 g of product from Example 47 in 300 ml of methylene chloride and 10 drops of dimethylformamide is added dropwise 15.67 g of oxalyl chloride. The reaction is stirred at room temperature for 18 hours and concentrated in vacuo. The residue is crystallized from diethyl ether to give 31.3 g of the desired product as a white solid.
Anal. Calc'd for $C_{22}H_{35}Cl$ $O_3$:C:68.99; H:9.21; Cl:9.25: Found: C:69.04; H:9.28; Cl:9.40.

EXAMPLE 49

N-Acetyl-3-methoxy-4-(tetradecyloxy)-N-(2-pyridinylmethyl)benzamide

The title compound is prepared by the procedure of Example 27 using 1.09 g product from Example 48, 0.450 g of product from Example 12, 0.144 g of 50% washed sodium hydride and 12 ml of dry tetrahydrofuran. The residue is purified by column chromatography (silica gel:35% ethyl acetate/hexane) to give 0.391 g of the desired product as yellow crystals.
MP 69°–70° C.
EI-MS:m/z 496 (M+).

EXAMPLE 50

2-[[Acetyl[3-methoxy-4-(tetradecyloxy)benzoyl]amino]methyl]-1-methylpyridinium iodide The title compound is prepared by the procedure of Example 28 using 0.322 g of product from Example 49 and 4.6 g of methyl iodide. The residue is recrystallized from methyl alcohol to give 0.411 g of the desired product as yellow crystals.
MP 66°–68° C.
MS(FAB): 511 (M+-I).

EXAMPLE 51

[4-(Tetradecyloxy)phenyl]acetic acid methyl ester

A mixture of 200 g of methyl 4-hydroxyphenylacetate, 350.4 g of 1-bromotetradecane, 207.9 g of potassium carbonate, 10 g of potassium iodide and 1.5 L of acetone is heated at reflux temperature for 24 hours. The reaction is cooled to room temperature, concentrated in vacuo and the residue is recrystallized from cold hexane to give 276.0 g of the desired product.
MP 36°–38° C.
EI-MS: m/z 362 (M+).

EXAMPLE 52

(4-Tetradecyloxyphenyl)acetic acid

The title compound is prepared by the procedure of Example 32 using 75 g of product from Example 51, 34.8 g of potassium hydroxide, 45 ml of water and 800 ml of ethyl alcohol. The residue is recrystallized from carbon tetrachloride/hexane to give 60.6 g of the desired product as white crystals.
MP 84°–86° C.
EI-MS: m/z 348 (M+).

EXAMPLE 53

4-(Tetradecyloxy)benzeneacetyl chloride

To a mixture of 60.6 g of product from Example 52 in 750 ml of methylene chloride and 0.636 g of dimethylformamide is added, dropwise, 33.1 g of oxalyl chloride. The reaction is stirred at room temperature for 18 hours. The mixture is concentrated in vacuo, redissolved in diethyl ether, passed through a pad of diatomaceous earth and concentrated in vacuo to give 63.81 g of the desired product.

MP 78°–80° C.

EXAMPLE 54

N-(2-Pyridinylmethyl)-4-(tetradecyloxy)benzeneacetamide

To a 0° C. solution of 4.64 g of 2-(aminomethyl)pyridine, 13.2 ml of pyridine and 50 ml of methylene chloride is added, dropwise, 15 g of product from Example 53 in 150 ml of methylene chloride. The reaction is stirred at 0° C. for 1 hour followed by 18 hours at room temperature. The reaction is diluted with chloroform, washed with sodium bicarbonate, water and saturated sodium chloride, dried and concentrated in vacuo. The residue is purified by column chromatography (silica gel:75–100% ethyl acetate/hexane) to give 11.0 g of the desired product as colorless prisms.

MP 86°–87° C.
EI-MS:438 (M+).

EXAMPLE 55

1-Methyl-2-[[[[4-(tetradecyloxy)phenyl]acetyl]amino]methyl]pyridinium iodide

The title compound is prepared by the procedure of Example 28 using 1.0 g of product from Example 54 and 16.18 g of methyl iodide. The residue is recrystallized from methyl alcohol to give 1.16 g of the desired product as cream prisms.

MP 150°–160° C. with decomposition.
MS(FAB): 453 (M+-I).

EXAMPLE 56

N-[2-(2-Pyridinyl)ethyl]-4-(tetradecyloxy)benzeneacetamide

To a 0° C. solution of 5.24 g of 2-(2-aminoethyl)pyridine, 13.22 ml of pyridine and 50 ml of methylene chloride is added, dropwise, 15 g of product from Example 53 in 150 ml of methylene chloride. The reaction is stirred at 0° C. for 4 hours followed by 68 hours at room temperature. The reaction is diluted with chloroform, washed with saturated sodium bicarbonate, water and saturated sodium chloride, dried and concentrated in vacuo. The residue is purified by column chromatography (silica gel:75–100% ethyl acetate/hexane) to give 8.3 g of the desired product as colorless prisms.

MP 90°–91° C.
EI-MS:m/z 452 (M+).

EXAMPLE 57

1-Methyl-2-[2-[[[4-(tetradecyloxy)phenyl]acetyl]amino]ethyl]pyridinium iodide

The title compound is prepared by the procedure of Example 28 using 1.0 g of product from Example 56 and 15.68 g of methyl iodide. The residue is recrystallized from methyl alcohol to give 1.09 g of the desired product as yellow crystals.

MP 140°–150° C. with decomposition.
MS(FAB): 467 (M+-I).

EXAMPLE 58

N-[2-(2-Pyridinyl)ethyl]-4-(tetradecyloxy)benzamide

To a 0° solution of 2.54 g of 2-(aminoethyl)pyridine, 50 ml of methylene chloride and 6.42 ml of pyridine is added, dropwise, 7.0 g of product from Example 3 in 250 ml of methylene chloride. The reaction is stirred at 0° C. for 2 hours followed by 14 hours at room temperature. The reaction is diluted with chloroform, washed with saturated sodium bicarbonate, water and saturated sodium chloride, dried and concentrated in vacuo. The residue is purified by column chromatography (silica gel:75–100% ethyl acetate/hexane) to give 3.58 g of the desired product.

MP 80°–82° C.
EI-MS:m/z 438 (M+).

EXAMPLE 59

1-Methyl-2-[2-[[4-(tetradecyloxy)benzoyl]amino]ethyl]pyridinium iodide

The title compound is prepared by the procedure of Example 28 using 0.750 g of product from Example 58 and 12.13 g of methyl iodide. The residue is recrystallized from methyl alcohol to give 0.90 g of the desired product as colorless needles.

MP 117°–118° C.
MS(FAB): 453 (M+-I).

EXAMPLE 60

3-Fluoro-4-hydroxybenzeneacetic acid methyl ester

A mixture of 2.0 g of 3-fluoro-4-hydroxybenzeneacetic acid, 10 ml of methyl alcohol and 1 ml of concentrated sulfuric acid is heated at reflux temperature for 23.5 hours. The cooled solution is diluted with water and extracted with methylene chloride. The organic layer is washed with water, saturated sodium bicarbonate, water and saturated sodium chloride; dried and concentrated in vacuo. The residue is purified by column chromatography (silica gel:25% ethyl acetate/hexane) to give 1.9 g of the desired product.

MP 32°–34° C.
EI-MS:m/z 184 (M+).

EXAMPLE 61

3-Fluoro-4-(tetradecyloxy)benzeneacetic acid methyl ester

A mixture of 23.0 g of product from Example 60, 34.6 g of 1-bromotetradecane, 54.6 g of potassium carbonate and 250 ml of acetone is heated at reflux temperature for 48 hours. The cooled reaction is filtered and concentrated in vacuo. The residue is purified by column chromatography (silica gel:0–4.5% ethyl acetate/hexane) to give 46.3 g of the desired product as colorless prisms.

MP 38°–40° C.
EI-MS:m/z 380 (M+).

EXAMPLE 62

3-Chloro-4-hydroxybenzeneacetic acid methyl ester

A mixture of 50 g of 3-chloro-4-hydroxybenzeneacetic acid, 250 ml of methyl alcohol and 10 ml of concentrated sulfuric acid is heated at reflux temperature for 23.5 hours. The cooled solution is diluted with water and extracted with methylene chloride. The organic layer is washed with saturated sodium bicarbonate and saturated sodium chloride, dried and concentrated in vacuo. The residue is purified by column chromatography (silica gel:30% ethyl acetate/hexane) to give 49.9 g of the desired product.

MP 35°–36° C.
EI-MS:m/z 200 (M+).

EXAMPLE 63

3-Chloro-4-(tetradecyloxy)benzeneacetic acid methyl ester

A mixture of 45 g of product from Example 62, 62.2 g of 1-bromotetradecane, 58.9 g of powdered potassium carbonate and 500 ml of acetone is heated at reflux temperature for 51 hours. The cooled solution is filtered and concentrated in vacuo. The residue is dissolved in methylene chloride, washed with 2% sodium bicarbonate and saturated sodium chloride, dried and concentrated in vacuo. The residue is purified by column chromatography (silica gel:5% ethyl acetate) and recrystallized from hexane to give 76.8 g of the desired product.

MP 24°–25° C.
EI-MS:396, 398 (M+).

EXAMPLE 64

3-Chloro-4-(tetradecyloxy)benzeneacetic acid

A mixture of 69.7 g of product from Example 63, 29.55 g of potassium hydroxide, 45 of water and 800 ml ethyl alcohol is heated at reflux temperature for 89 hours. The cooled solution was made acidic (pH 2) with concentrated hydrogen chloride; followed by heating to distill off the ethyl alcohol. The solution is diluted with diethyl ether and water. The organic layer is dried and concentrated in vacuo. The residue is recrystallized from methylene chloride/hexane to give 40.0 g of the desired product as colorless needles.

MP 68°–69° C.
EI-MS:m/z 382 (M+).

EXAMPLE 65

3-Chloro-4-(tetradecyloxy)benzeneacetyl chloride

To a mixture of 10 g of product from Example 64, 0.095 g of dimethylformamide and 150 ml of methylene chloride is added, dropwise, 3.42 ml of oxalyl chloride. The reaction is stirred at room temperature for 69 hours and then concentrated in vacuo. The residue is dissolved in diethyl ether, filtered and concentrated in vacuo to give 10.5 g of the desired product as a yellow oil.

Anal. $C_{22}H_{34}O_2Cl_2$ Calc'd: C:65.83; H:8.54; Cl:17.66; Found: C:65.92; H:8.20; Cl:17.11.
EI-MS:m/z 396

EXAMPLE 66

3-Methoxy-4-(tetradecyloxy)benzeneacetic acid ethyl ester

A mixture of 50 g of 3-methoxy-4-hydroxybenzeneacetic acid ethyl ester, 66.1 g of powdered potassium carbonate, 70.57 g of 1-bromotetradecane and 500 ml of acetone is heated at reflux temperature for 76 hours. The reaction is cooled, filtered and the filtrate concentrated in vacuo. The residue is dissolved in methylene chloride, washed with 2% sodium bicarbonate and saturated sodium chloride, dried and concentrated in vacuo. The residue is purified by column chromatography (silica gel:0–10% ethyl acetate/hexane) to give 66.6 g of the desired product as colorless crystals.

MP 40°–41° C.
EI-MS:m/z 406 (M+).

EXAMPLE 67

3-Methoxy-4-(tetradecyloxy)benzeneacetic acid

The title compound is prepared by the procedure of Example 64 using 60 g of product from Example 66, 24.84 g of potassium hydroxide, 45 ml of water and 650 ml of ethyl alcohol. The reaction is heated at reflux temperature for 41 hours. The residue is recrystallized from methylene chloride/hexane to give 38 g of the desired product as cream needles.

MP 68.5°–70° C.
EI-MS:m/z 378 (M+).

EXAMPLE 68

3-Methoxy-4-(tetradecyloxy)benzeneacetyl chloride

To a mixture of 10 g of product from Example 67, 0.0965 g of dimethylformamide and 150 ml of methylene chloride is added dropwise 3.46 ml of oxalyl chloride. The reaction is stirred at room temperature for 20 hours and the solvent concentrated in vacuo. The residue is dissolved in diethyl ether, filtered and concentrated in vacuo to give 10.5 g of the desired product as colorless needles.

MP 56°–57° C.

EXAMPLE 69

N-(2-Pyridinylmethyl)-N-[[4-(tetradecyloxy)phenyl]methyl]acetamide

The title compound is prepared by the procedure of Example 27 using 9.4 g of product from Example 20, 3.87 g of product from Example 12, 1.24 g of 50% sodium hydride and 130 ml of dry tetrahydrofuran. The reaction is stirred at room temperature for 3½ hours. The residue is purified by column chromatography (silica gel:60–100% ethyl acetate/hexane) to give 9.42 g of the desired product as colorless crystals.

MP 66°–67° C.

EXAMPLE 70

2-[[Acetyl[[4-(tetradecyloxy)phenyl]methyl]amino]methyl]-1-ethylpyridinium iodide The title compound is prepared by the procedure of Example 28 using 0.500 g of product from Example 69 and 4.42 ml of ethyl iodide. The residue is recrystallized from methanol to give 0.554 g of the desired product as yellow crystals.

MP 108°–110° C.
MS(FAB): 481(M+-I).

EXAMPLE 71

N-(2-Pyridinylmethyl)-N-[[3-(tetradecyloxy)phenyl]methyl]acetamide

The title compound is prepared by the procedure of Example 27 using 2.25 g of product from Example 25, 0.881 g of product from Example 12, 0.282 g of 50% sodium hydride and 30 ml of tetrahydrofuran. The reaction is stirred at 0° C. for 1 hour, room temperature for 18 hours and at reflux temperature for 6 hours. The residue is purified by column chromatography (silica gel: 90% ethyl acetate/hexane) to give 1.57 g of product as pale yellow crystals. Spectral data shows the product as 2 rotomers.

MP 45°–46° C.
EI-MS: 452 (M+).

EXAMPLE 72

2-[[Acetyl[[3-(tetradecyloxy)phenyl]methyl]amino]methyl]-1-methylpyridinium iodide The title compound is prepared by the procedure of Example 28 using 1.1 g of product from Example 71 and 7.56 ml of methyl iodide. The residue is recrystallized from methyl alcohol to give 1.42 g of the desired product as yellow/orange crystals. The spectral data indicates the presence of 2 rotomers.

MP 128°-130° C. with decomposition.
MS(FAB): 467 (M+-I).

EXAMPLE 73

N-(3-Pyridinylmethyl)-N-[[4-(tetradecyloxy)phenyl]methyl]acetamide

The title compound is prepared by the procedure of Example 27 using 1.1 g of product from Example 20, 0.431 g of product from Example 14, 0.145 g of washed 50% sodium hydride and 12 ml of tetrahydrofuran. The reaction is stirred at room temperature for 21 hours followed by heating at reflux temperature for 5½ hours. The residue is purified by column chromatography (silica gel: 5% methyl alcohol/ethyl acetate) to give 0.535 g of the desired product. The spectral data indicates the presence of 2 rotomers.

$^1$H NMR (CDCl$_3$): d 8.7–8.4(2H); 7.7–6.8(6H); 4.55–4.45 (4H); 4.0–3.9(2H); 2.25–2.2(3H); 1.8–1.65(2H); 1.5–1.25(20H); 0.9–0.8(3H).

EXAMPLE 74

3-[[Acetyl[[4-(tetradecyloxy)phenyl]methyl]amino]methyl]-1-methylpyridinium iodide The title compound is prepared by the procedure of Example 28 using 0.492 g of product from Example 73 and 3.38 ml of methyl iodide. The residue is purified by crystallization to give 0.64 g of the desired product as orange crystals.

MP softens 95° C. with decomposition.
MS(FAB): 467 (M+-I).

EXAMPLE 75

N-(2-Pyridinylmethyl)-N-[[2-(tetradecyloxy)phenyl]methyl]acetamide

The title compound is prepared by the procedure of Example 27 using 2.45 g of product from Example 22, 0.960 g of product from Example 12, 0.322 g of washed 50% sodium hydride and 30 ml of tetrahydrofuran. The reaction is stirred at 0° C. for 1 hour, room temperature for 18 hours; followed by heating at reflux temperature for 6 hours. The residue is purified by column chromatography (silica gel: 80% ethyl acetate/hexane) to give 0.976 g of the desired product as a yellow oil. The spectral data shows the presence of 2 rotomers.

EI-MS: m/z 452 (M+).

EXAMPLE 76

2-[[Acetyl[[2-(tetradecyloxy)phenyl]methyl]amino]methyl]-1-methylpyridinium iodide The title compound is prepared by the procedure of Example 28 using 0.90 g of product from Example 75 and 6.19 ml of methyl iodide. The residue is purified by crystallization from methyl alcohol to give 1.135 g of the desired product as yellow crystals. The spectral data indicates the presence of 2 rotomers.

MP 112°-114° C. with decomposition.
MS(FAB): 467 (M+-I).

EXAMPLE 77

N-(4-Pyridinylmethyl)-N-[[4-(tetradecyloxy)phenyl]methyl]acetamide

The title compound is prepared by the procedure of Example 27 using 2.55 g of product from Example 20, 0.999 g of product from Example 15, 0.319 g of washed 50% sodium hydride and 30 ml of tetrahydrofuran. The reaction is stirred at room temperature for 18 hours, heated at reflux temperature for 24 hours; followed by stirring at room temperature for an additional 48 hours. The residue is purified by column chromatography (silica gel: 5% methyl alcohol/ethyl acetate) to give 0.862 g of the desired product. The spectral data indicates the presence of 2 rotomers.

MP 52°-54° C.
EI-MS: m/z 452 (M+).

EXAMPLE 78

4-[[Acetyl[[4-(tetradecyloxy)phenyl]methyl]amino]methyl]-1-methylpyridinium iodide The title compound is prepared by the procedure of Example 28 using 0.741 g of product from Example 77 and 5.1 ml of methyl iodide. The residue is recrystallized from methyl alcohol to give 0.933 g of the desired product as orange crystals. The spectral data indicates 2 rotomers.

MP softens 100°-120° C. with decomposition.
MS(FAB): 467 (M+-I).

EXAMPLE 79

4-Methyl-N-(2-pyridinylmethyl)benzenesulfonamide

To a 0° C. solution of 15.0 g of 2-(aminomethyl)pyridine, 15.44 g of triethylamine and 150 ml of methylene chloride is added 29.1 g of p-toluenesulfonyl chloride in 100 ml of methylene chloride. The reaction mixture is allowed to warm to room temperature and is stirred for 4.5 hours. The solution is poured into saturated sodium bicarbonate and extracted with methylene chloride. The combined organic layers are washed with saturated sodium chloride, dried and concentrated in vacuo. The residue is purified by column chromatography (silica gel: 50% ethyl acetate/hexane 20% methyl alcohol/ethyl acetate); then recrystallized from ethyl acetate/hexane to give 25.9 g of the desired product as colorless crystals.

MP 84°-86° C.

EXAMPLE 80

4-Methyl-N-(2-pyridinylmethyl)-N-[[3-(tetradecyloxy)phenyl]methyl]benzenesulfonamide The title compound is prepared by the procedure of Example 27, using 1.23 g of product from Example 79, 1.71 g of product from Example 25, 0.321 g of washed 50% sodium hydride and 70 ml of tetrahydrofuran. The reaction is stirred at room temperature for 68 hours. The residue is purified by column chromatography (silica gel: 25% ethyl acetate/hexane) to give 1.15 g of the desired product as a colorless oil, which crystallized on standing.

MP 49°-50° C.
EI-MS:m/z 409 (M+-SO$_2$Ts).

EXAMPLE 81

4-Nitrophenyl tetradecyl ether

A mixture of 75 g of 4-nitrophenol, 149.5 g of 1-bromotetradecane, 26.96 g of sodium hydroxide, 2.18 g of trioctyl methylammonium chloride, 400 ml of toluene and 400 of water is heated at reflux for 65 hours. The organic layer is separated, washed with 1N sodium hydroxide and dilute hydrochloric acid, dried and concentrated in vacuo. The residue is recrystallized from petroleum ether to give the desired product.
MP 57°–60° C.
EI-MS:m/z 335 (M+).

EXAMPLE 82

4-(Tetradecyloxy)aniline

A solution of 30 g of product from Example 81 in 150 ml of ethyl alcohol and 20 ml of ethyl acetate is treated with 2 g of 10% palladium/carbon in a Parr Hydrogenator for 18 hours. The reaction solution is filtered and concentrated in vacuo. The residue is recrystallized from hexane to give 25.7 g of the desired product as a white solid.
MP 65°–68° C.
EI-MS:m/z 305 (M+).

EXAMPLE 83

N-[4-(Tetradecyloxy)phenyl]-3-pyridinemethanamine

To a room temperature slurry of 7.26 g of product from Example 82, 60 ml of methyl alcohol and 9.5 ml of 5N hydrochloric acid/methanol is added, dropwise, 2.55 g of 3-pyridinecarboxaldehyde. After 10 minutes, a total of 1.64 g of sodium cyanoborohydride is very carefully added in 3 separate portions over 1.5 hours. The initial reaction is vigorous. The reaction mixture is stirred at room temperature for 68 hours, diluted with water, made basic with potassium hydroxide and extracted with methylene chloride. The methylene chloride extract is washed with saturated sodium chloride, dried and concentrated in vacuo. The residue is purified by column chromatography (silica gel: 90% ethyl acetate/hexane) to give 7.2 g of the desired product as colorless crystals.
MP 75°–76° C.
EI-MS:m/z 369 (M+).

EXAMPLE 84

4-(Hexadecyloxy)phenol

To a 0° C. suspension, under argon, of 29 g of 60% sodium hydride in 350 ml of dimethylformamide is added dropwise over 40 minutes, 60.0 g of hydroquinone in 450 ml of dimethylformamide. The suspension is stirred at 0° C. for ½ hour; followed by the dropwise addition of 192 g of 1-iodohexadecane in 450 ml tetrahydrofuran. The reaction temperature is maintained at 0° C. during the addition of the alkyl halide; followed by stirring at room temperature for 3 hours. The mixture is poured carefully into dilute hydrochloric acid and extracted with chloroform. The organic layer is washed with water, dried and concentrated in vacuo.

EXAMPLE 85

[4-(Hexadecyloxy)phenoxy]acetic acid methyl ester

A mixture of 23 g of product from Example 84, 13.15 g of methyl bromoacetate, 10.45 g of potassium carbonate and 200 ml of acetone is heated at reflux for 24 hours. The reaction is cooled, chloroform added, filtered and concentrated. The residue is recrystallized from hexane to give 25 g of the desired product as a white solid.

EXAMPLE 86

[4-(Hexadecyloxy)phenoxy]acetic acid

A solution of 24.5 g of product from Example 85, 10.14 g of potassium hydroxide, 10 ml of water and 250 ml of ethyl alcohol is heated at reflux for 3 hours; followed by standing at 50° C. for 18 hours. The reaction is poured into dilute hydrochloric acid, extracted with chloroform, dried and concentrated. The residue is recrystallized from hexane/carbon tetrachloride to give 13.7 g of the desired product as a white solid.
MP 125°–127° C.
EI-MS:m/z 392 (M+).

EXAMPLE 87

[4-(Hexadecyloxy)phenoxy]acetyl chloride

A mixture of 13.2 g of product from Example 86, 6.4 g of oxalyl chloride, 225 ml of methylene chloride and 5 drops of dimethylformamide is stirred at room temperature for 17 hours. The solvent is concentrated in vacuo, the residue is dissolved in ether, filtered through diatomaceous earth and concentrated in vacuo to give 13.5 g of the desired product.

EXAMPLE 88

2-[4-(Hexadecyloxy)phenoxy]-N-(2-pyridinylmethyl)acetamide

To a 0° C. solution of 3.0 g of product from Example 87 is added 50 ml of methylene chloride, 0.829 g of 2-(aminomethyl)pyridine and 2.31 g of pyridine. The reaction is stirred at 0° C. for 3 hours; followed by 20 hours at room temperature. The mixture is poured into chloroform and saturated sodium bicarbonate. The aqueous layer is extracted with chloroform and the combined chloroform layers are washed with saturated sodium chloride, dried and concentrated in vacuo. The residue is purified by column chromatography (silica gel: 75% ethyl acetate/hexane) to give 2.90 g of the desired product as a colorless solid.
MP 68°–69° C.
EI-MS:m/z 482 (M+).

EXAMPLE 89

1-Ethyl-2-[[[[4-(hexadecyloxy)phenoxy]acetyl]amino]methyl]pyridinium iodide

The title compound is prepared by the procedure of Example 8, using 0.50 g of product from Example 88, 8.1 g of ethyl iodide and heating the mixture at 115° C. for 22 hours. The residue is recrystallized from methyl alcohol to give 0.53 g of the desired product as light yellow prisms.
MP 137°–138° C.
MS(FAB): m/z 511 (M+-I).

EXAMPLE 90

N-Acetyl-2-[4-(hexadecyloxy)phenoxy]-N-(2-pyridinylmethyl)acetamide

A mixture of 0.70 g of product from Example 88, 2.96 g of acetic anhydride, 0.027 g of 4-N,N-dimethylaminopyridine and 15 ml of pyridine is heated at 110° C. for 35 hours and at reflux temperature for 57 hours. The reaction is poured into water and extracted with methylene chloride. The organic layer is washed with saturated sodium chloride, dried and concentrated in vacuo. The residue is purified by column chromatography (silica gel: 35% ethyl acetate/hexane) to give 0.366 g of product as light yellow crystals.
MP 58°–59° C.
EI-MS:m/z 524 (M+).

EXAMPLE 91

2-[[Acetyl[[4-(hexadecyloxy)phenoxy]acetyl]amino]-methyl]-1-methylpyridinium iodide The title compound is prepared by the procedure of Example 28, using 0.268 g of product from Example 90 and 3.63 g of methyl iodide. The residue is crystallized from hot methyl alcohol/chloroform to give 0.30 g of the desired product as colorless needles.
MP 182°–183° C.
MS(FAB): m/z 539 (M+-I).

EXAMPLE 92

2-[4-(Hexadecyloxy)phenoxy]-N-[2-(2-pyridinyl)ethyl]acetamide

To a 0° C. solution of 2.3 g of product from Example 87 in 50 ml of methylene chloride is added, dropwise, 0.72 g of 2-(2-aminoethyl)pyridine followed by 1.77 g of pyridine. The reaction is stirred at room temperature for 16 hours, poured into chloroform and saturated sodium bicarbonate and extracted with chloroform. The combined chloroform layers are washed with saturated sodium chloride, dried and concentrated in vacuo. The residue is purified by column chromatography (silica gel: 75% ethyl acetate/hexane) to give 2.2 g of the desired product as a colorless solid.
MP 74°–75° C.
EI-MS:m/z 496 (M+).

EXAMPLE 93

1-Ethyl-2-[2-[[[4-(hexadecyloxy)phenoxy]acetyl]amino]ethyl]pyridinium iodide

The title compound is prepared by the procedure of Example 8, using 0.50 g of product from Example 92, 7.85 g of ethyl iodide and heating the mixture at 110°–120° C. for 26 hours. The residue is recrystallized from methyl alcohol to give 0.535 g of the desired product.
MP 65°–67° C.
MS(FAB): 525 (M+-I).

EXAMPLE 94

Phenyl [4-(tetradecyloxy)phenyl]methyl carbonate

To a 0° C. mixture of 9.0 g of product from Example 19, 4.44 g of pyridine and 70 ml of methylene chloride is added, dropwise, 5.28 of phenyl chloroformate. The reaction is stirred at 0° C. for 15 minutes; followed by room temperature for 30 minutes. The mixture is poured into saturated sodium bicarbonate and the aqueous layer is extracted with methylene chloride. The combined organic layers are washed with saturated sodium chloride, dried and concentrated in vacuo. The residue is purified by column chromatography (silica gel: 0–5% ethyl acetate/hexane) to give 12.6 g of colorless prisms.
MP 34°–35° C.
EI-MS:m/z 440 (M+).

EXAMPLE 95

[4-(Tetradecyloxy)phenyl]methyl (2-pyridinylmethyl)carbamate

A mixture of 0.50 g of product from Example 94 and 0.184 g of 2-(aminomethyl)pyridine is heated in a sealed tube at 100° C. for 80 minutes. The crystalline reaction product is dissolved in methylene chloride, washed with 5% potassium hydroxide and saturated sodium chloride, dried and concentrated in vacuo. The residue is purified by column chromatography (silica gel: 50% ethyl acetate/hexane) to give 0.481 g of the desired product as colorless plates.
MP 67°–68° C.
EI-MS:m/z 454 (M+).

EXAMPLE 96

[4-(Tetradecyloxy)phenyl]methyl acetyl(2-pyridinylmethyl)carbamate

A mixture of 3.0 g of product from Example 95, 13.5 g of acetic anhydride, 0.081 g of 4-N,N-dimethylaminopyridine, 3.34 g of triethylamine and 25 ml of methylene chloride is heated, in a sealed tube, at 100° C. for 54 hours. The reaction is concentrated in vacuo, dissolved in methylene chloride, washed with saturated sodium bicarbonate, dried and concentrated in vacuo. The residue is purified by column chromatography (silica gel: 20% ethyl acetate/hexane) to give 1.42 g of the desired product as colorless crystals.
MP 52°–53° C.
Analysis Calc'd $C_{30}H_{44}N_2O_4$: C,72.55;H,8.93;N,5.64. Found: C, 72.33;H, 8.93;N,5.59.

EXAMPLE 97

2-[[Acetyl[[[4-(tetradecyloxy)phenyl]methoxy]carbonyl]amino]methyl]-1-methylpyridinium iodide A mixture of 1.37 g of product from Example 96 and 19.55 g of methyl iodide is heated in a sealed tube at 100° C. for 5 hours. The reaction is concentrated in vacuo and the residue recrystallized from methyl alcohol to give 1.65 g of the desired product.
MP 56°–66° C. with decomposition
MS(FAB): 467 (M+-I-acetyl).

EXAMPLE 98

4-(Tetradecyloxy)benzamide

A mixture of 50 g of 4-hydroxybenzamide, 106.1 g of 1-bromotetradecane, 75.59 g of potassium hydroxide, 5.46 g of sodium iodide and 600 ml of dimethylformamide is heated at 110° C. for 24 hours; followed by stirring at room temperature for 72 hours. The reaction is poured into water, the resulting solid collected and washed with water. The solid is recrystallized first from chloroform then ethyl acetate to give 58 g of the desired product.
MP 128°–130° C.
EI-MS:m/z 333 (M+).

EXAMPLE 99

4-(Tetradecyloxy)benzenemethanamine

To a room temperature mixture of 3.64 g of lithium aluminum hydride in 300 ml of dry tetrahydrofuran is added a hot solution of 15.98 g of product from Example 98 in 150 ml of tetrahydrofuran. The reaction is stirred at room temperature for 20 hours, refluxed for 8 hours and stirred at room temperature for 50 hours. The reaction is treated with saturated sodium sulfate, filtered and concentrated to give 14.77 g of the desired product as colorless crystals.

MP 62°–64° C.
EI-MS:m/z 319 (M+).

EXAMPLE 100

[[4-(Tetradecyloxy)phenyl]methyl phenyl carbamate

To a 0° C. solution of 3.0 g of product from Example 99, 1.49 g of pyridine and 25 ml of methylene chloride is added, over 5 minutes, 1.76 g of phenyl chloroformate. The reaction is stirred at 0° C. for 10 minutes; followed by 30 minutes at room temperature. The mixture is poured into saturated sodium bicarbonate extracted with methylene chloride. The organic layer is washed with saturated sodium chloride, dried and concentrated in vacuo. The residue is purified by column chromatography (silica gel: 15% ethyl acetate/hexane) to give 3.77 g of the desired product as colorless crystals.

MP 69°–71° C.
EI-MS:m/z 345 (M+-$C_6H_6O$).

EXAMPLE 101

N-(2-Pyridinylmethyl)-N'-[[4-(tetradecyloxy)phenyl]methyl]urea

A mixture of 1.5 g of product from Example 100 and 0.55 g of 2-(aminomethyl)pyridine is heated, in the dark, at 100° C. for 17 hours. The residue was recrystallized from methyl alcohol to give 1.3 g of the desired product as colorless crystals.

MP 108°–109° C.
EI-MS:m/z 453 (M+).

EXAMPLE 102

3,4-Dihydroxy benzoic acid methyl ester

A mixture of 100 g of 3,4-dihydroxy benzoic acid, 600 ml methyl alcohol and 10 ml of concentrated sulfuric acid is heated at reflux for 18 hours. The reaction mixture is cooled to room temperature, poured into water and extracted with methylene chloride. The organic layer is washed with saturated sodium bicarbonate and sodium chloride, dried and concentrated in vacuo to give 50.6 g of the desired product.

MP 130°–131° C.
EI-MS:m/z 168 (M+).

EXAMPLE 103

3,4-Bis(tetradecyloxy)benzoic acid methyl ester

A mixture of 15.0 g of product from Example 102, 53.2 g of 1-bromotetradecane, 37 g of potassium carbonate, 1.04 g of potassium iodide and 350 ml of 2-butanone is heated at reflux for 28.5 hours. The reaction is cooled to room temperature, filtered and the filtrate concentrated in vacuo. The residue is recrystallized from methylene chloride/hexane to give 49.33 g of the desired product.

MP 50°–51° C.
EI-MS:m/z 560 (M+).

EXAMPLE 104

3,4-Bis(tetradecyloxy)benzoic acid

A mixture of 35 g of product from Example 103, 7.5 g of potassium hydroxide, 30 ml of water and 500 ml of ethyl alcohol is heated at reflux for 24 hours. The reaction is then stirred at room temperature for 48 hours and acidified to pH 2 with concentrated hydrochloric acid. The mixture is concentrated in vacuo, diluted with water and extracted with chloroform. The combined organic layers are washed with saturated sodium chloride, dried and concentrated in vacuo to give 34.2 g of the desired product.

MP 116°–117° C.
EI-MS:m/z 546.

EXAMPLE 105

3,4-Bis(tetradecyloxy)benzoyl chloride

To a room temperature solution of 5.0 g of product from Example 104 in 80 ml of methylene chloride and 5 drops of dimethylformamide is added 1.74 g of oxalyl chloride. The reaction is stirred at room temperature for 2.5 days and concentrated in vacuo. The residue is dissolved in diethyl ether, passed through a pad of diatomaceous earth and concentrated in vacuo to give 5.1 g of the desired product as colorless crystals.

MP 68°–70° C.
EI-MS:m/z 560.

EXAMPLE 106

N-Acetyl-N-(2-pyridinylmethyl)-3,4-bis(tetradecyloxy)benzamide(A) and
N-(2-Pyridinylmethyl)-3,4-bis(tetradecyloxy)benzamide(B)

The title compounds are prepared by the procedure of Example 27 using 4.8 g of product from Example 105, 0.530 g of washed 50% sodium hydride, 1.34 g of product from Example 12 and 100 ml of dry tetrahydrofuran. The reaction is stirred at room temperature for 20 minutes, heated at reflux temperature for 20 hours and cooled to room temperature. The mixture is poured into water and extracted with chloroform. The chloroform extracts are washed with saturated sodium chloride, dried and concentrated in vacuo. The residue is purified by column chromatography (silica gel:50% ethyl acetate/hexane) to give 0.44 g of the desired product (A) as pale yellow crystals and 2.37 g of deacylated amide (B) as colorless crystals.

(A) MP 85°–87° C. (B) MP 90°–91° C.
EI-MS: m/z 679 (M+). EI-MS: m/z 637 (M+).

EXAMPLE 107

2-[[Acetyl[3,4-bis(tetradecyloxy)benzoyl]amino]methyl]-1-methylpyridinium iodide A mixture of 0.227 g of product (A) from Example 106 and 2.37 g of methyl iodide is heated in a sealed tube at 105° C. for 17 ¼ hours. The reaction is concentrated in vacuo to give 0.27 g of the desired product as pale yellow crystals.

MP softens 74°–84° C.
MS(FAB): m/z 693 (M+-I).

EXAMPLE 108

1-Methyl-2-[[[3,4-bis(tetradecyloxy)benzoyl]amino]methyl]pyridinium iodide

A mixture of 1.0 g of product (B) from Example 106 and 11.14 g of methyl iodide is heated in a sealed tube at 105° C. for 17¼ hours. The reaction is concentrated in vacuo to give 1.2 g of product as pale yellow crystals.

MP softens 160°–170° C.
MS(FAB): m/z 651 (M+-I).

EXAMPLE 109

3,4-Bis(heptyloxy)benzoic acid methyl ester

A mixture of 25 g of product from Example 102, 72.3 g of 1-iodoheptane, 61.65 g of potassium carbonate and 500 ml of 2-butanone is heated at reflux temperature for 44 hours. The cooled reaction mixture is filtered and concentrated in vacuo. The oily residue is purified by chromatography (silica gel: 10% ethyl acetate/hexane) to give 53.7 g of the desired product.

EI-MS: m/z 364 (M+).

EXAMPLE 110

3,4-Bis(heptyloxy)benzoic acid

A mixture of 25 g of product from Example 109, 11.54 g of potassium hydroxide, 30 ml of water and 500 ml ethyl alcohol is heated at reflux temperature for 24 hours. The reaction mixture is cooled and maintained at room temperature for 48 hours. The mixture is acidified to pH 2 with concentrated hydrochloric acid, concentrated in vacuo, diluted with water and extracted with chloroform. The combined chloroform extracts are washed with saturated sodium chloride, dried and concentrated in vacuo to give 22.58 g of the desired product as colorless crystals.

MP 122°-123° C.

EXAMPLE 111

3,4-Bis(heptyloxy)benzoyl chloride

To a room temperature mixture of 5 g of product from Example 110 in 80 ml of methylene chloride and 5 drops of dimethylformamide is added 2.72 g of oxalyl chloride. The reaction is stirred at room temperature for 2.5 days and concentrated in vacuo. The residue is dissolved in diethyl ether, passed through a pad of diatomaceous earth and concentrated in vacuo to give 5.27 g of the desired product as colorless crystals.

MP 57°-58° C.

EXAMPLE 112

N-Acetyl-3,4-bis(heptyloxy)-N-(2-pyridinylmethyl)-benzamide

The title compound is prepared by the procedure of Example 27 using 5.0 g of product from Example 111, 0.683 g of washed 50% sodium hydride, 2.14 g of product from Example 12 and 100 ml of dry tetrahydrofuran. The reaction is stirred at room temperature for 1 hour, heated at reflux temperature for 18 hours and cooled to room temperature. The mixture is poured into water, extracted with chloroform and concentrated in vacuo. The residue is purified by column chromatography (silica gel: 15-30% ethyl acetate/hexane) to give 2.93 g of the desired product.

MP 75°-77° C.

EI-MS: m/z 482 (M+).

EXAMPLE 113

2-[[Acetyl[3,4-bis(heptyloxy)benzoyl]amino]methyl]-1-methylpyridinium iodide A mixture of 1.0 g of product from Example 112 and 14.7 g of methyl iodide is heated in a sealed tube at 105° C. from 17¼ hours. The reaction is concentrated in vacuo to give 1.24 g of the desired product as yellow crystals.

MP soften 60°-70° C.

MS(FAB): m/z 497 (M+-I).

EXAMPLE 114

2-Pyridinecarbonyl chloride, hydrochloride

To a mixture of 20 g of picolinic acid, 200 ml of methylene chloride and 5 drops of dimethylformamide is added, dropwise, 30.93 g of oxalyl chloride. The reaction is stirred at room temperature for 18 hours and concentrated in vacuo to give the desired product as a black crystalline material.

MP 116°-130° C. with decomposition.

EXAMPLE 115

N-[[4-(Tetradecyloxy)phenyl]methyl-2-pyridinecarboxamide

To a room temperature suspension of 6.72 g of product from Example 114 in 200 ml methylene chloride is added, dropwise over 15 minutes, 10.05 g of product from Example 99 dissolved in 160 ml of methylene chloride. The reaction is stirred at room temperature for 10 minutes, followed by the dropwise addition of 12.73 g of triethylamine. The solution is stirred at room temperature for 19 hours, poured into a solution consisting of equal volumes saturated sodium bicarbonate, saturated sodium chloride and water, and extracted with 50/50 chloroform/methylene chloride. The organic layers are washed with saturated sodium chloride, dried and concentrated in vacuo. The residue is purified by column chromatography (silica gel: 25% ethyl acetate/hexane) to give 10.75 g of the desired product as pale yellow crystals.

MP 51°-52° C.

EI-MS: m/z 424 (M+).

EXAMPLE 116

N-[[4-(Tetradecyloxy)phenyl]methyl]benzamide

To a room temperature slurry of 2.01 g of nicotinoyl chloride hydrochloride in 25 ml of methylene chloride is added, via cannula, 3.0 g of product from Example 99 in 75 ml of methylene chloride. After 10 minutes, 3.8 g of triethylamine is added, dropwise, and the solution is stirred at room temperature for 20 hours. The reaction is poured into half saturated sodium bicarbonate and extracted with chloroform. The combined organic layers are washed with saturated sodium chloride and concentrated in vacuo. The residue is purified by chromatography (silica gel: 7.5% methyl alcohol/chloroform) and recrystallized from heptane/methyl alcohol to give 3.57 g of the desired product as pale yellow needles.

MP 102°-103° C.

EI-MS: m/z 424 (M+).

EXAMPLE 117

1-Methyl-3-[[[[4-(tetradecyloxy)phenyl]methyl]amino]-carbonyl]pyridinium iodide A mixture of 0.250 g of product from Example 116 and 4.18 g of methyl iodide is heated in a sealed tube at 100° C. for 18 hours, then maintained at room temperature for 48 hours. The reaction is concentrated in vacuo to give 0.33 g of the desired product as yellow crystals.

MP 90°-91° C.

MS(FAB): m/z 439 (M+-I).

EXAMPLE 118

N-[[4-(Tetradecyloxy)phenyl]methyl]benzamide

The title compound is prepared by the procedure of Example 116 using 3.0 g of product from Example 99, 2.01 g of isonicotinoyl chloride hydrochloride, 3.8 of triethylamine and 100 ml of methylene chloride. The product is purified by chromatography (silica gel: 3.5% methyl alcohol/chloroform) followed by recrystallization from heptane/methanol to give 3.06 g of the desired product as colorless crystals.
MP 87°-88° C.
EI-MS: m/z 424 (M+).

EXAMPLE 119

1-Methyl-4-[[[[4-(tetradecyloxy)phenyl]methyl]amino]-carbonyl]pyridinium iodide

A mixture of 0.250 g of product from Example 118 and 4.18 g of methyl iodide is heated in a sealed tube at 100° C. for 18 hours, then maintained at room temperature for 48 hours. The reaction is concentrated in vacuo to give 0.34 g of the desired product as yellow crystals.
MP 106°-108° C.
MS(FAB): m/z 439 (M+-I).

EXAMPLE 120

N-[[4-(Tetradecyloxy)phenyl]methyl]acetamide

To a room temperature mixture of 15 g of product from Example 99, 0.229 g of 4-N,N-dimethylaminopyridine and 50 ml of methylene chloride is added 5 ml of acetic anhydride. An additional 50 ml of methylene chloride is added and the solution is stirred at room temperature for 69 hours. The reaction is poured into half saturated sodium bicarbonate and extracted with methylene chloride. The combined organic layers are washed with half saturated sodium bicarbonate, water and saturated sodium chloride. The dried methylene chloride layer is concentrated in vacuo and purified by chromatography (silica gel: 5% methyl alcohol/chloroform) to give 16.29 g of the desired product as colorless prisms.
MP 100°-101° C.
EI-MS: m/z 361 (M+).

EXAMPLE 121

N-(2-Pyridinylmethyl)methanesulfonamide

To a 0° solution of 15 g of 2-(aminomethyl)pyridine, 15.44 g of triethylamine and 150 ml of methylene chloride is added 17.48 g of methanesulfonyl chloride in 100 ml of methylene chloride. The mixture is stirred at 0° C. for 1 hour followed by stirring at room temperature for 3 hours. The reaction is poured into saturated sodium bicarbonate and extracted with methylene chloride. The combined extracts are washed with saturated sodium chloride and concentrated in vacuo. The residue is purified by chromatography (silica gel: 10% methyl alcohol/ethyl acetate) to give 19.84 g of the desired product.
MP 42°-43° C.
EI-MS: m/z 171 (M+—CH₃).

EXAMPLE 122

N-(2-Pyridinylmethyl)-N-[[4-(tetradecyloxy)phenyl]-methyl]methanesulfonamide

To a room temperature slurry of 0.391 g of 50% sodium hydride in 20 ml of dry tetrahydrofuran is added, via cannula, 1.27 g of product from Example 121 in 30 ml of dry tetrahydrofuran. The reaction is stirred at room temperature for 1.5 hours. Two and one half grams of product from Example 20 in 30 ml of dry tetrahydrofuran is added via cannula. The reaction is stirred at room temperature for 20 hours followed by heating at reflux temperature for 2 hours. The cooled reaction is poured into half saturated sodium chloride and extracted with methylene chloride. The combined organic layers are washed with saturated sodium chloride, dried and concentrated in vacuo. The residue is purified by chromatography (silica gel: 40% ethyl acetate/hexane) to give 1.22 g of the desired product as colorless crystals.
MP 62°-63° C.
EI-MS: m/z 409 (M+—SO₂CH₃—H).

EXAMPLE 123

1-Methyl-2-[[(methylsulfonyl)[[4-(tetradecyloxy)-phenyl]methyl]amino]methyl]pyridinium iodide A mixture of 0.350 g of product from Example 122 and 5.08 g of methyl iodide is heated at 90° C. for 17 hours. Thin layer chromatography shows the presence of starting material. The mixture is reheated at 125° C. for 23 hours. The reaction is concentrated in vacuo to give 0.45 g of the desired product as pale yellow crystals.
MP 122°-123° C. with decomposition
MS(FAB): 503 (M+-I).

EXAMPLE 124

N-(2-Pyridinylmethyl)-N-(methylsulfonyl)-4-(tetradecyloxy)benzamide

To a room temperature solution of 0.428 g of washed 50% sodium hydride in 15 ml of dry tetrahydrofuran is added, via cannula, 1.58 g of product from Example 121 dissolved in 20 ml of dry tetrahydrofuran. The mixture is stirred for 2 hours and 3.0 g of product from Example 3 dissolved in 20 ml of dry tetrahydrofuran is added, via cannula. After stirring at room temperature for 30 minutes, the reaction is heated at reflux temperature for 2 hours. The cooled mixture is poured into half saturated sodium chloride and extracted with chloroform. The organic layer is dried and concentrated in vacuo. The residue is purified by chromatography (silica gel: 15-40% ethyl acetate/hexane) to give 3.85 g of the desired product.
MP 94°-95° C.
EI-MS: m/z 502 (M+).

EXAMPLE 125

1-Methyl-2-[[(methylsulfonyl)[4-(tetradecyloxy)benzoyl]amino]methyl]pyridinium salt with trifluoromethanesulfonic acid (1:1)

A mixture of 1.0 g of product from Example 124, 0.359 g of methyl trifluoromethanesulfonate and 3 ml of toluene is heated, under nitrogen, for 18 hours. Thin layer chromatography indicates the presence of starting material. An additional 0.065 g of methyl trifluoromethanesulfonate is added and the reaction is heated for 4 hours. The reaction is concentrated in vacuo to give 1.33 g of the desired product as tan crystals.
MS(FAB): m/z 517 (M+—OSO₂CF₃).

EXAMPLE 126

2-[[4-(Tetradecyloxy)phenyl]methyl]-1H-pyrrolo[3,4-b]pyridine-1,3(2H)-dione

A mixture of 6.0 g of product from Example 99, 2.8 g of 2,3-pyridinecarboxylic anhydride and 40 ml of toluene is heated at reflux temperature for 21 hours in a vessel equipped with a Dean-Stark trap. The reaction is stirred at room temperature for 20 hours and concentrated in vacuo. The residue is purified by chromatography (silica gel: 45% ethyl acetate/hexane) to give 3.39 g of the desired product as colorless crystals.
MP 88°–90° C.
EI-MS: m/z 450 (M+).

EXAMPLE 127

7-Dioxo-6-[[4-(tetradecyloxy)phenyl]methyl]-6,7-dihydro-1-methyl-5,5H-pyrrolo[3,4-b]pyridinium salt with trifluoromethanesulfonic acid (1:1)

A mixture of 1.0 g of product from Example 126, 0.400 g of methyl trifluoromethanesulfonate and 3 ml of toluene is heated at 105° C. for 11 hours. The reaction is concentrated to give 1.35 g of the desired product as cream crystals.
MP softens 70°–85° C.
MS(FAB): m/z 465 (M+—OSO$_2$CF$_3$).

EXAMPLE 128

2-[[4-(Tetradecyloxy)phenyl]methyl]-1H-pyrrolo[3,4-c]pyridine-1,3(2H)-dione

A mixture of 2.5 g of product from Example 99 and 1.17 g of 3,4-pyridinecarboxylic anhydride is heated, in a sealed tube, at 190° C. for 12 minutes. The cooled crystalline product is dissolved in chloroform, dried over anhydrous sodium sulfate, filtered and concentrated in vacuo. The residue is purified by chromatography (silica gel: 30–40% ethyl acetate/hexane) to give 3.12 g of the desired product as colorless crystals.
MP 76°–77° C.
EI-MS: m/z 450 (M+).

EXAMPLE 129

3-Dioxo-2-[[4-(tetradecyloxy)phenyl]methyl]-2,3-dihydro-5-methyl-1,1H-pyrrolo[3,4-c]pyridinium iodide A mixture of 1.0 g of product from Example 128 and 15.75 g of methyl iodide is heated at 105° C. for 10 hours. The reaction is concentrated in vacuo to give 1.25 g of the desired product as orange crystals.
MP 162°–164° C. with decomposition.
MS(FAB): m/z 465 (M+-I).

EXAMPLE 130

4-(Decyloxy)-3-(1,1-dimethylethyl)benzoic acid methyl ester

A mixture of 12.0 g of 3-(1,1-dimethylethyl)-4-hydroxybenzoic acid methyl ester, 11.15 g of 1-bromodecane, 9.95 g of potassium carbonate, 0.797 g of potassium iodide and 100 ml of 2-butanone is heated at reflux temperature for 40 hours. The reaction is cooled, filtered and the filtrate concentrated in vacuo. The residue is purified by chromatography (silica gel: 0–3% ethyl acetate/hexane) to give 18.49 g of the desired product as a light yellow oil.
EI-MS: m/z 348 (M+).

EXAMPLE 131

4-(Decyloxy)-3-(1,1-dimethylethyl)benzoic acid

A mixture of 15.0 g of product from Example 130, 7.24 g of potassium hydroxide, 100 ml methyl alcohol, 40 ml ethyl alcohol and 10 ml of water is heated at reflux temperature for 18 hours. The reaction is cooled to room temperature, made acidic to pH 2, concentrated in vacuo, swirled with water and the solid collected. The solid residue is washed with water and dried in a vacuum oven to give 13 g of the desired product as colorless needles.
MP 130°–132° C.
EI-MS: m/z 334 (M+).

EXAMPLE 132

4-(Decyloxy)-3-(1,1-dimethylethyl)benzoyl chloride

To 3.0 g of product from Example 131 in 30 ml of methylene chloride plus 2 drops of dimethylformamide is added 2.0 ml of oxalyl chloride via syringe. The reaction is stirred at room temperature for 18 hours, concentrated in vacuo, dissolved in diethyl ether and filtered through a pad of diatomaceous earth. The diethyl ether is concentrated in vacuo to give 3.15 g of the desired product as a yellow oil.

EXAMPLE 133

N-Acetyl-4-(decyloxy)-3-(1,1-dimethylethyl)-N-(2-pyridinylmethyl)benzamide

The title compound is prepared by the procedure of Example 27, using 2.9 g of product from Example 132, 1.3 g of product from Example 12, 0.433 g of 50% sodium hydride and 60 ml of dry tetrahydrofuran. The residue is purified by chromatography to give 1.74 g of the desired product as a yellow oil.
EI-MS: m/z 466 (M+).

EXAMPLE 134

2-[[Acetyl[4-(decyloxy)-3-(1,1-dimethylethyl)benzoyl]amino]methyl]-1-methylpyridinium iodide A mixture of 1.56 g of product from Example 133 and 23.68 g of methyl iodide is heated in a sealed tube, in the dark, at 105° C. for 18 hours. The reaction is concentrated in vacuo to give 1.86 g of the desired product as light yellow crystals.
MP softens 70° C., final melt 110° C. with decomposition.
MS(FAB): m/z 481 (M+-I).

EXAMPLE 135

2-[[Acetyl[3-methoxy-4-(tetradecyloxy)benzoyl]amino]methyl]-1-ethylpyridinium iodide A mixture of 1.01 g of product from Example 49 and 15.83 g of ethyl iodide is heated at 105° C. for 23 hours. The reaction is concentrated in vacuo and triturated with diethyl ether to give 1.0 g of the desired product as yellow crystals.
MP softens 70°–90° C.
MS(FAB): m/z 525 (M+-I).

EXAMPLE 136

N-Acetyl-4-(decyloxy)-3-(1,1-dimethylethyl)-N-(3-pyridinylmethyl)benzamide

The title compound is prepared by the procedure of Example 27, using 0.90 g of product from Example 33, 0.316 g of washed 50% sodium hydride, 2.57 g of product from Example 14 and 25 ml of dry tetrahydrofuran. The residue is purified by chromatography (silica gel: 40% ethyl acetate/hexane) to give 1.81 g of the desired product as a yellow oil which crystallizes on standing.
MP 46°–47° C.
EI-MS: m/z 522 (M+).

EXAMPLE 137

3-[[Acetyl[3-(1,1-dimethylethyl)-4-(tetradecyloxy)benzoyl]amino]methyl]-1-methylpyridinium iodide A mixture of 1.58 g of product from Example 136 and 21.44 g of methyl iodide is heated in a sealed tube, in the dark, at 105° C. for 18 hours. The reaction is concentrated in vacuo to give 1.87 g of the desired product as yellow crystals.
MP softens 70° C., final melt at 110° C. with decomposition.
MS(FAB): m/z 537 (M+-I).

EXAMPLE 138

N-Acetyl-3-(1,1-dimethylethyl)-4-(tetradecyloxy)-N-(4-pyridinylmethyl)benzamide

The title compound is prepared by the procedure of Example 27, using 0.90 g of product from Example 15, 0.316 g of washed 50% sodium hydride, 2.57 g of product from Example 33 and 25 ml of dry tetrahydrofuran. The residue is purified by chromatography (silica gel: 40% ethyl acetate/hexane) to give 0.275 g of desired product as a yellow oil which crystallizes on standing.
MP 55°–56° C.
EI-MS: m/z 522 (M+).

EXAMPLE 139

4-[[Acetyl[3-(1,1-dimethylethyl)-4-(tetradecyloxy)benzoyl]amino]methyl]-1-methylpyridinium iodide A mixture of 0.225 g of product from Example 138 and 6.11 g of methyl iodide is heated in a sealed tube, in the dark, at 105° C. for 18 hours. The reaction is concentrated in vacuo to give 0.279 g of the desired product as orange crystals.
MP 60°–75° C. with decomposition.
MS(FAB): m/z 537 (M+-I).

EXAMPLE 140

N-Acetyl-3-(1,1-dimethylethyl)-N-(2-pyridinylmethyl)-4-(tetradecyloxy)benzamide N'-oxide To a solution of product from Example 34 in 15 ml of glacial acetic acid is added, via cannula, 1.52 g of 3-chloroperbenzoic acid in 15 ml of glacial acetic acid. The reaction is heated at 80° C. for 18 hours, cooled, poured into an excess of saturated sodium bicarbonate solution and extracted with chloroform. The organic layers are combined, washed with saturated sodium chloride and concentrated in vacuo. The residue is purified by chromatography (silica gel: 90% ethyl acetate/hexane) to give 0.2185 g of the desired product as a yellow oil.
MS(FAB): m/z 539 (M++I).

EXAMPLE 141

1-Methyl-2-[[[[(4-methylphenyl)sulfonyl]][[3-(tetradecyloxy)phenyl]methyl]amino]methyl]pyridinium iodide A mixture of 1.01 g of product from Example 80 and 12.69 g of methyl iodide is heated, in a sealed tube, at 100° C. for 5 hours. The reaction is concentrated to give 1.17 g of the desired product as a yellow-green foam.
MP soften 48°–60° C. with decomposition.
MS(FAB): m/z 579 (M+-I).

EXAMPLE 142

N-(3-Pyridinylmethyl)-N-[4-(tetradecyloxy)phenyl]acetamide

To a room temperature solution of 2.49 g of product from Example 83, 1.27 ml of pyridine and 30 ml of methylene chloride is added, dropwise, 0.985 g of acetyl chloride. The reaction is stirred at room temperature for 1.5 hours, poured into saturated sodium bicarbonate and extracted with methylene chloride. The organic layer is washed with saturated sodium chloride, dried and concentrated in vacuo. The residue is purified by chromatography (silica gel: 95% ethyl acetate/hexane) to give 2.65 g of the desired product as a yellow oil.
EI-MS: m/z 438 (M+).

EXAMPLE 143

3-[[Acetyl[4-(tetradecyloxy)phenyl]amino]methyl]1-methylpyridinium iodide

A mixture of 2.3 g of product from Example 142 and 37.21 g of methyl iodide is heated, in a sealed tube, at 95° C. for 13 hours. The reaction is concentrated in vacuo to give 3.11 g of the desired product.
MP softens 82°–98° C. with decomposition.
MS(FAB): m/z 453 (M+-I).

EXAMPLE 144

N-Phenyl-4-(tetradecyloxy)benzamide

To a mixture of 7.02 g of aniline and 4.48 g of pyridine in 200 ml of methylene chloride is added 20 g of product from Example 3. The reaction is stirred at room temperature for 2 hours; diluted with chloroform and water and heated to dissolve the solids. The layers are separated and the organic layer is washed with hot dilute hydrochloric acid. The organic layer is dried, concentrated in vacuo and the residue is recrystallized from chloroform/hexane to give 23.1 g of the desired product.
MP 124°–126° C.
MS(FAB): m/z 410 (M++H).

EXAMPLE 145

N-Phenyl-4-(tetradecyloxy)benzenemethanamine

To a 0° C. suspension of 21.0 g of product from Example 144 in 200 ml of dry tetrahydrofuran is added, dropwise over 30 minutes, 51.27 ml of 1M solution of lithium aluminum hydride in tetrahydrofuran. The reaction is stirred at room temperature for 1 hour, heated at reflux temperature for 2 hours and stirred overnight at room temperature. Ethyl acetate is added followed by concentrated sodium hydroxide. The reaction is filtered, concentrated in vacuo and the residue is recrystallized from hexane to give 16.9 g of the desired product.
MP 58°–59° C.
EI-MS: m/z 395 (M+).

EXAMPLE 146

N-Phenyl-N-[[4-(tetradecyloxy)phenyl]methyl]-3-pyridinecarboxamide

To a room temperature slurry of 1.03 g of nicotinoyl chloride hydrochloride in 20 ml of methylene chloride is added, via cannula, 2.0 g of product from Example 145 in 30 ml of methylene chloride. After 5 minutes, 2.05 g of triethylamine is added and the reaction stirred at room temperature for 72 hours. The solution is poured into saturated sodium bicarbonate and extracted with methylene chloride. The organic layer is washed with saturated sodium chloride, dried and concentrated in vacuo. The residue is purified by chromatography (silica gel: 40% ethyl acetate/hexane) to give 2.35 g of the desired product.

MP 65°–67° C.
EI-MS: m/z 500 (M+).

EXAMPLE 147

1-Methyl-3-[[phenyl[[4-(tetradecyloxy)phenyl]methyl]amino]carbonyl]pyridinium iodide A mixture of 0.80 g of product from Example 146 and 11.34 g of methyl iodide is heated, in a sealed tube, at 100° C. for 10 hours. The reaction is concentrated in vacuo to give 1.02 g of the desired product as light yellow crystals.

MP 176°–178° C.
MS(FAB): m/z 515 (M+-I).

EXAMPLE 148

3-[[Phenyl[[4-(tetradecyloxy)phenyl]methyl]amino]carbonyl]-1-propylpyridinium iodide A mixture of 0.80 g of product from Example 146 and 13.58 g of iodopropane is heated, in a sealed tube, at 100° C. for 10 hours. The reaction is concentrated in vacuo to give 1.07 g of the desired product as orange crystals.

MP 78°–80° C.
MS(FAB): m/z 543 (M+-I).

According to the methods outlined hereinabove in Flowsheets A and C, and described in detail in Examples 1–4, 10, 11, 16–19, 21, 23, 24, 26, 31–33, 36–38, 40–43, 46–48, 51–68, 79, 84–89, 92, 93, 98, 102–106, 108–111, 121, 124, 125, and 130–132, the compounds of this invention listed hereinbelow in List 1 can be prepared. These methods are applicable to the preparation of the compounds of this invention by one skilled in the art.

List 1

1-Methyl-2-[[[3-chloro-4-(tetradecyloxy)benzoyl]amino]methyl]pyridinium iodide

1-Methyl-2-[[[3-chloro-4-(dodecyloxy)benzoyl]amino]methyl]pyridinium iodide

1-Methyl-2-[[[3-methoxy-4-(tetradecyloxy)benzoyl]amino]methyl]pyridinium iodide

1-Methyl-2-[[[3-methoxy-4-(dodecyloxy)benzoyl]amino]methyl]pyridinium iodide

1-Methyl-2-[[[3-(1,1-dimethylethyl)-4-(tetradecyloxy)benzoyl]amino]methyl]pyridinium iodide 1-Methyl-2-[[[3-(1,1-dimethylethyl)-4-(dodecyloxy)benzoyl]amino]methyl]pyridinium iodide 1-Methyl-2-[[[2-chloro-4-(tetradecyloxy)benzoyl]amino]methyl]pyridinium iodide 1-Methyl-2-[[[2-chloro-4-(dodecyloxy)benzoyl]amino]methyl]pyridinium iodide 1-Methyl-2-[[[2-chloro-3-(tetradecyloxy)benzoyl]amino]methyl]pyridinium iodide 1-Methyl-2-[[[2-methoxy-4-(hexadecyloxy)benzoyl]amino]methyl]pyridinium iodide 1-Methyl-2-[[[2-methoxy-4-(decyloxy)benzoyl]amino]methyl]pyridinium iodide 1-Methyl-2-[[[[3-chloro-4-(tetradecyloxy)phenyl]acetyl]amino]methyl]pyridinium iodide 1-Methyl-2-[[[[3-chloro-4-(dodecyloxy)phenyl]acetyl]amino]methyl]pyridinium iodide 1-Methyl-2-[[[[3-methoxy-4-(tetradecyloxy)phenyl]acetyl]amino]methyl]pyridinium iodide 1-Methyl-2-[[[[3-methoxy-4-(dodecyloxy)phenyl]acetyl]amino]methyl]pyridinium iodide 1-Methyl-2-[[[[3-(1,1-dimethylethyl)-4-(tetradecyloxy)phenyl]acetyl]amino]methyl]pyridinium iodide 1-Methyl-2-[[[[3-(1,1-dimethylethyl)-4-(dodecyloxy)phenyl]acetyl]amino]methyl]pyridinium iodide 1-Methyl-2-[[[[2-chloro-4-(tetradecyloxy)phenyl]acetyl]amino]methyl]pyridinium iodide 1-Methyl-2-[[[[2-chloro-4-(dodecyloxy)phenyl]acetyl]amino]methyl]pyridinium iodide 1-Methyl-2-[[[[2-chloro-3-(tetradecyloxy)phenyl]acetyl]amino]methyl]pyridinium iodide 1-Methyl-2-[[[[2-methoxy-4-(hexadecyloxy)phenyl]acetyl]amino]methyl]pyridinium iodide 1-Methyl-2-[[[[2-methoxy-4-(decyloxy)phenyl]acetyl]amino]methyl]pyridinium iodide 1-Methyl-2-[2-[[[3-chloro-4-(tetradecyloxy)phenoxy]acetyl]amino]ethyl]pyridinium iodide 1-Methyl-2-[2-[[[3-chloro-4-(dodecyloxy)phenoxy]acetyl]amino]ethyl]pyridinium iodide 1-Methyl-2-[2-[[[3-methoxy-4-(tetradecyloxy)phenoxy]acetyl]amino]ethyl]pyridinium iodide 1-Methyl-2-[2-[[[3-methoxy-4-(dodecyloxy)phenoxy]acetyl]amino]ethyl]pyridinium iodide 1-Methyl-2-[2-[[[3-(1,1-dimethylethyl)-4-(tetradecyloxy)phenoxy]acetyl]amino]ethyl]pyridinium iodide 1-Methyl-2-[2-[[[3-(1,1-dimethylethyl)-4-(dodecyloxy)phenoxy]acetyl]amino]ethyl]pyridinium iodide 1-Methyl-2-[2-[[[2-chloro-4-(tetradecyloxy)phenoxy]acetyl]amino]ethyl]pyridinium iodide 1-Methyl-2-[2-[[[2-chloro-4-(dodecyloxy)phenoxy]acetyl]amino]ethyl]pyridinium iodide 1-Methyl-2-[2-[[[2-chloro-3-(tetradecyloxy)phenoxy]acetyl]amino]ethyl]pyridinium iodide 1-Methyl-2-[2-[[[2-methoxy-4-(hexadecyloxy)phenoxy]acetyl]amino]ethyl]pyridinium iodide 1-Methyl-2-[2-[[[2-methoxy-4-(decyloxy)phenoxy]acetyl]amino]ethyl]pyridinium iodide 1-Methyl-3-[[[3-chloro-4-(tetradecyloxy)benzoyl]amino]methyl]pyridinium iodide 1-Methyl-3-[[[3-chloro-4-(dodecyloxy)benzoyl]amino]methyl]pyridinium iodide 1-Methyl-3-[[[3-methoxy-4-(tetradecyloxy)benzoyl]amino]methyl]pyridinium iodide 1-Methyl-3-[[[3-methoxy-4-(dodecyloxy)benzoyl]amino]methyl]pyridinium iodide 1-Methyl-3-[[[3-(1,1-dimethylethyl)-4-(dodecyloxy)benzoyl]amino]methyl]pyridinium iodide 1-Methyl-3-[[[2-chloro-4-(tetradecyloxy)benzoyl]amino]methyl]pyridinium iodide 1-Methyl-3-[[[2-chloro-4-(dodecyloxy)benzoyl]amino]methyl]pyridinium iodide 1-Methyl-3-[[[2-chloro-3-(tetradecyloxy)benzoyl]amino]methyl]pyridinium iodide 1-Methyl-3-[[[2-methoxy-4-(decyloxy)benzoyl]amino]methyl]pyridinium iodide 1-Methyl-3-[[[[3-chloro-4-(tetradecyloxy)phenyl]acetyl]amino]methyl]pyridinium iodide 1-Methyl-3-[[[[3-methoxy-4-(tetradecyloxy)phenyl]acetyl]amino]methyl]pyridinium iodide 1-Methyl-3-[[[[3-methoxy-4-(hexadecyloxy)phenyl]acetyl]amino]methyl]pyridinium iodide 1-Methyl-3-[[[[3-methoxy-4-(decyloxy)phenyl]acetyl]amino]methyl]pyridinium iodide 1-Methyl-3-[[[[3-(1,1-dimethylethyl)-4-(hexadecyloxy)phenyl]acetyl]amino]methyl]pyridinium iodide 1-Methyl-3-[[[[3-(1,1-dimethylethyl)-4-(decyloxy)phenyl]acetyl]amino]methyl]pyridinium iodide 1-Methyl-3-[[[[2-chloro-4-(hexadecyloxy)phenyl]acetyl]amino]methyl]pyridinium iodide 1-Methyl-3-[[[[2-chloro-4-(decyloxy)phenyl]acetyl]amino]methyl]pyridinium iodide 1-Methyl-3-[[[[2-methoxy-4-(tetradecyloxy)phenyl]acetyl]amino]methyl]pyridinium iodide 1-Methyl-3-[[[[2-methoxy-4-(dodecyloxy)phenyl]acetyl]amino]methyl]pyridinium iodide 1-Methyl-3-[[[[2-methoxy-3-(tetradecyloxy)phenyl]acetyl]amino]methyl]pyridinium iodide 1-Methyl-3-[2-[[[3-chloro-4-(hexadecyloxy)phenoxy]acetyl]amino]ethyl]pyridinium iodide 1-Methyl-3-[2-[[[3-chloro-4-(decyloxy)phenoxy]acetyl]amino]ethyl]pyridinium iodide 1-Methyl-3-[2-[[[3-methoxy-4-(hexadecyloxy)phenoxy]acetyl]amino]ethyl]pyridinium iodide 1-Methyl-3-[2-[[[3-methoxy-4-(decyloxy)phenoxy]acetyl]amino]ethyl]pyridinium iodide 1-Methyl-3-[2-[[[3-(1,1-dimethylethyl)-4-(hexadecyloxy)phenoxy]acetyl]amino]ethyl]pyridinium iodide 1-Methyl-3-[2-[[[3-(1,1-dimethylethyl)-4-(decyloxy)phenoxy]acetyl]amino]ethyl]pyridinium iodide 1-Methyl-3-[2-[[[2-chloro-4-(hexadecyloxy)phenoxy]acetyl]amino]ethyl]pyridinium iodide 1-Methyl-3-[2-[[[2-chloro-4-(decyloxy)phenoxy]acetyl]amino]ethyl]pyridinium iodide 1-Methyl-3-[2-[[[2-methoxy-4-(tetradecyloxy)phenoxy]acetyl]amino]ethyl]pyridinium iodide 1-Methyl-3-[2-[[[2-methoxy-4-(dodecyloxy)phenoxy]acetyl]amino]ethyl]pyridinium iodide 1-Methyl-3-[2-[[[2-methoxy-3-(tetradecyloxy)phenoxy]acetyl]amino]ethyl]pyridinium iodide 1-Methyl-4-[[[3-chloro-4-(hexadecyloxy)benzoyl]amino]methyl]pyridinium iodide 1-Methyl-4-[[[3-chloro-4-(decyloxy)benzoyl]amino]methyl]pyridinium iodide 1-Methyl-4-[[[3-methoxy-4-(hexadecyloxy)benzoyl]amino]methyl]pyridinium iodide 1-Methyl-4-[[[3-methoxy-4-(decyloxy)benzoyl]amino]methyl]pyridinium iodide 1-Methyl-4-[[[3-(1,1-dimethylethyl)-4-(hexadecyloxy)benzoyl]amino]methyl]pyridinium iodide 1-Methyl-4-[[[3-(1,1-dimethylethyl)-4-(decyloxy)benzoyl]amino]methyl]pyridinium iodide 1-Methyl-4-[[[2-chloro-4-(hexadecyloxy)benzoyl]amino]methyl]pyridinium iodide 1-Methyl-4-[[[2-chloro-4-(decyloxy)benzoyl]amino]methyl]pyridinium iodide 1-Methyl-4-[[[2-methoxy-4-(tetradecyloxy)benzoyl]amino]methyl]pyridinium iodide 1-Methyl-4-[[[2-methoxy-4-(dodecyloxy)benzoyl]amino]methyl]pyridinium iodide 1-Methyl-4-[[[2-methoxy-3-(tetradecyloxy)benzoyl]amino]methyl]pyridinium iodide 1-Methyl-4-[[[[3-chloro-4-(hexadecyloxy)phenyl]acetyl]amino]methyl]pyridinium iodide 1-Methyl-4-[[[[3-chloro-4-(decyloxy)phenyl]acetyl]amino]methyl]pyridinium iodide 1-Methyl-4-[[[[3-methoxy-4-(hexadecyloxy)phenyl]acetyl]amino]methyl]pyridinium iodide 1-Methyl-4-[[[[3-methoxy-4-(decyloxy)phenyl]acetyl]amino]methyl]pyridinium iodide 1-Methyl-4-[[[[3-(1,1-dimethylethyl)-4-(hexadecyloxy)phenyl]acetyl]amino]methyl]pyridinium iodide 1-Methyl-4-[[[[3-(1,1-dimethylethyl)-4-(decyloxy)phenyl]acetyl]amino]methyl]pyridinium iodide 1-Methyl-4-[[[[2-chloro-4-(hexadecyloxy)phenyl]acetyl]amino]methyl]pyridinium iodide 1-Methyl-4-[[[[2-chloro-4-(decyloxy)phenyl]acetyl]amino]methyl]pyridinium iodide 1-Methyl-4-[[[[2-methoxy-4-(tetradecyloxy)phenyl]acetyl]amino]methyl]pyridinium iodide 1-Methyl-4-[[[[2-methoxy-4-(dodecyloxy)phenyl]acetyl]amino]methyl]pyridinium iodide 1-Methyl-4-[[[[2-methoxy-3-(tetradecyloxy)phenyl]acetyl]amino]methyl]pyridinium iodide 1-Methyl-4-[2-[[[3-chloro-4-(hexadecyloxy)phenoxy]acetyl]amino]ethyl]pyridinium iodide 1-Methyl-4-[2-[[[3-chloro-4-(decyloxy)phenoxy]acetyl]amino]ethyl]pyridinium iodide 1-Methyl-4-[2-[[[3-methoxy-4-(hexadecyloxy)phenoxy]acetyl]amino]ethyl]pyridinium iodide 1-Methyl-4-[2-[[[3-methoxy-4-(decyloxy)phenoxy]acetyl]amino]ethyl]pyridinium iodide 1-Methyl-4-[2-[[[3-(1,1-dimethylethyl)-4-(hexadecyloxy)phenoxy]acetyl]amino]ethyl]pyridinium iodide 1-Methyl-4-[2-[[[3-(1,1-dimethylethyl)-4-(decyloxy)phenoxy]acetyl]amino]ethyl]pyridinium iodide 1-Methyl-4-[2-[[[2-chloro-4-(hexadecyloxy)phenoxy]acetyl]amino]ethyl]pyridinium iodide 1-Methyl-4-[2-[[[2-chloro-4-(decyloxy)phenoxy]acetyl]amino]ethyl]pyridinium iodide 1-Methyl-4-[2-[[[2-methoxy-4-(tetradecyloxy)phenoxy]acetyl]amino]ethyl]pyridinium iodide 1-Methyl-4-[2-[[[2-methoxy-4-(dodecyloxy)phenoxy]acetyl]amino]ethyl]pyridinium iodide 1-Methyl-4-[2-[[[2-methoxy-3-(tetradecyloxy)phenoxy]acetyl]amino]ethyl]pyridinium iodide 1-Ethyl-2-[[[3-chloro-4-(hexadecyloxy)benzoyl]amino]methyl]pyridinium iodide 1-Ethyl-2-[[[3-chloro-4-(decyloxy)benzoyl]amino]methyl]pyridinium iodide 1-Ethyl-2-[[[3-methoxy-4-(hexadecyloxy)benzoyl]amino]methyl]pyridinium iodide 1-Ethyl-2-[[[3-methoxy-4-(decyloxy)benzoyl]amino]methyl]pyridinium iodide 1-Ethyl-2-[[[3-(1,1-dimethylethyl)-4-(hexadecyloxy)benzoyl]amino]methyl]pyridinium iodide 1-Ethyl-2-[[[2-chloro-4-(tetradecyloxy)benzoyl]amino]methyl]pyridinium iodide 1-Ethyl-2-[[[2-chloro-4-(dodecyloxy)benzoyl]amino]methyl]pyridinium iodide 1-Ethyl-2-[[[2-chloro-3-(tetradecyloxy)benzoyl]amino]methyl]pyridinium iodide 1-Ethyl-2-[[[2-methoxy-4-(hexadecyloxy)benzoyl]amino]methyl]pyridinium iodide 1-Ethyl-2-[[[2-methoxy-4-(decyloxy)benzoyl]amino]methyl]pyridinium iodide 1-Ethyl-2-[[[[3-chloro-4-(tetradecyloxy)phenyl]acetyl]amino]methyl]pyridinium iodide 1-Ethyl-2-[[[[3-chloro-4-(dodecyloxy)phenyl]acetyl]amino]methyl]pyridinium iodide 1-Ethyl-2-[[[[3-chloro-4-(decyloxy)phenyl]acetyl]amino]methyl]pyridinium iodide 1-Ethyl-2-[[[[3-methoxy-4-(hexadecyloxy)phenyl]acetyl]amino]methyl]pyridinium iodide 1-Ethyl-2-[[[[3-methoxy-4-(decyloxy)phenyl]acetyl]amino]methyl]pyridinium iodide 1-Ethyl-2-[[[[3-(1,1-dimethylethyl)-4-(hexadecyloxy)phenyl]acetyl]amino]methyl]pyridinium iodide 1-Ethyl-2-[[[[3-(1,1-dimethylethyl)-4-(decyloxy)phenyl]acetyl]amino]methyl]pyridinium iodide 1-Ethyl-2-[[[[2-chloro-4-(hexadecyloxy)phenyl]acetyl]amino]methyl]pyridinium iodide 1-Ethyl-2-[[[[2-chloro-4-(decyloxy)phenyl]acetyl]amino]methyl]pyridinium iodide 1-Ethyl-2-[[[[2-methoxy-4-(tetradecyloxy)phenyl]acetyl]amino]methyl]pyridinium iodide 1-Ethyl-2-[[[[2-methoxy-3-(tetradecyloxy)phenyl]acetyl]amino]methyl]pyridinium iodide 1-Ethyl-2-[2-[[[3-chloro-4-(hexadecyloxy)phenoxy]acetyl]amino]ethyl]pyridinium iodide 1-Ethyl-2-[2-[[[3-methoxy-4-(hexadecyloxy)phenoxy]acetyl]amino]ethyl]pyridinium iodide 1-Ethyl-2-[2-[[[3-(1,1-dimethylethyl)-4-(hexadecyloxy)phenoxy]acetyl]amino]ethyl]pyridinium iodide 1-Ethyl-2-[2-[[[2-chloro-4-(hexadecyloxy)phenoxy]acetyl]amino]ethyl]pyridinium iodide 1-Ethyl-2-[2-[[[2-chloro-4-(decyloxy)phenoxy]acetyl]amino]ethyl]pyridinium iodide 1-Ethyl-2-[2-[[[2-methoxy-4-(tetradecyloxy)phenoxy]acetyl]amino]ethyl]pyridinium iodide 1-Ethyl-2-[2-[[[2-methoxy-4-(dodecyloxy)phenoxy]acetyl]amino]ethyl]pyridinium iodide 1-Ethyl-2-[2-[[[2-methoxy-3-(tetradecyloxy)phenoxy]acetyl]amino]ethyl]pyridinium iodide 1-Ethyl-3-[[[3-chloro-4-(hexadecyloxy)benzoyl]amino]methyl]pyridinium iodide 1-Ethyl-3-[[[3-chloro-4-(decyloxy)benzoyl]amino]methyl]pyridinium iodide 1-Ethyl-3-[[[3-methoxy-4-(hexadecyloxy)benzoyl]amino]methyl]pyridinium iodide 1-Ethyl-3-[[[3-methoxy-4-(decyloxy)benzoyl]amino]methyl]pyridinium iodide 1-Ethyl-3-[[[3-(1,1-dimethylethyl)-4-(hexadecyloxy)benzoyl]amino]methyl]pyridinium iodide 1-Ethyl-3-[[[3-(1,1-dimethylethyl)-4-(decyloxy)benzoyl]amino]methyl]pyridinium iodide 1-Ethyl-3-[[[2-chloro-4-(hexadecyloxy)benzoyl]amino]methyl]pyridinium iodide 1-Ethyl-3-[[[2-chloro-4-(decyloxy)benzoyl]amino]methyl]pyridinium iodide 1-Ethyl-3-[[[2-methoxy-4-(tetradecyloxy)benzoyl]amino]methyl]pyridinium iodide 1-Ethyl-3-[[[2-methoxy-4-(dodecyloxy)benzoyl]amino]methyl]pyridinium iodide 1-Ethyl-3-[[[2-methoxy-3-(tetradecyloxy)benzoyl]amino]methyl]pyridinium iodide 1-Ethyl-3-[[[[3-chloro-4-(hexadecyloxy)phenyl]acetyl]amino]methyl]pyridinium iodide 1-Ethyl-3-[[[[3-chloro-4-(decyloxy)phenyl]acetyl]amino]methyl]pyridinium iodide 1-Ethyl-3-[[[[3-methoxy-4-(hexadecyloxy)phenyl]acetyl]amino]methyl]pyridinium iodide 1-Ethyl-3-[[[[3-methoxy-4-(decyloxy)phenyl]acetyl]amino]methyl]pyridinium iodide 1-Ethyl-3-[[[[3-(1,1-dimethylethyl)-4-(hexadecyloxy)phenyl]acetyl]amino]methyl]pyridinium iodide 1-Ethyl-3-[[[[3-(1,1-dimethylethyl)-4-(decyloxy)phenyl]acetyl]amino]methyl]pyridinium iodide 1-Ethyl-3-[[[[2-chloro-4-(hexadecyloxy)phenyl]acetyl]amino]methyl]pyridinium iodide 1-Ethyl-3-[[[[2-chloro-4-(decyloxy)phenyl]acetyl]amino]methyl]pyridinium iodide 1-Ethyl-3-[[[[2-methoxy-4-(tetradecyloxy)phenyl]acetyl]amino]methyl]pyridinium iodide 1-Ethyl-3-[[[[2-methoxy-4-(dodecyloxy)phenyl]acetyl]amino]methyl]pyridinium iodide 1-Ethyl-3-[[[[2-methoxy-3-(tetradecyloxy)phenyl]acetyl]amino]methyl]pyridinium iodide 1-Ethyl-3-[2-[[[3-chloro-4-(hexadecyloxy)phenoxy]acetyl]amino]ethyl]pyridinium iodide 1-Ethyl-3-[2-[[[3-chloro-4-(decyloxy)phenoxy]acetyl]amino]ethyl]pyridinium iodide 1-Ethyl-3-[2-[[[3-methoxy-4-(hexadecyloxy)phenoxy]acetyl]amino]ethyl]pyridinium iodide 1-Ethyl-3-[2-[[[3-methoxy-4-(decyloxy)phenoxy]acetyl]amino]ethyl]pyridinium iodide 1-Ethyl-3-[2-[[[3-(1,1-dimethylethyl)-4-(hexadecyloxy)phenoxy]acetyl]amino]ethyl]pyridinium iodide 1-Ethyl-3-[2-[[[3-(1,1-dimethylethyl)-4-(decyloxy)phenoxy]acetyl]amino]ethyl]pyridinium iodide 1-Ethyl-3-[2-[[[2-chloro-4-(hexadecyloxy)phenoxy]acetyl]amino]ethyl]pyridinium iodide 1-Ethyl-3-[2-[[[2-chloro-4-(decyloxy)phenoxy]acetyl]amino]ethyl]pyridinium iodide 1-Ethyl-3-[2-[[[2-methoxy-4-(tetradecyloxy)phenoxy]acetyl]amino]ethyl]pyridinium iodide 1-Ethyl-3-[2-[[[2-methoxy-4-(dodecyloxy)phenoxy]acetyl]amino]ethyl]pyridinium iodide 1-Ethyl-4-[[[3-chloro-4-(tetradecyloxy)benzoyl]amino]methyl]pyridinium iodide 1-Ethyl-4-[[[3-chloro-4-(dodecyloxy)benzoyl]amino]methyl]pyridinium iodide 1-Ethyl-4-[[[3-methoxy-4-(tetradecyloxy)benzoyl]amino]methyl]pyridinium iodide 1-Ethyl-4-[[[3-methoxy-4-(dodecyloxy)benzoyl]amino]methyl]pyridinium iodide 1-Ethyl-4-[[[3-(1,1-dimethylethyl)-4-(tetradecyloxy)benzoyl]amino]methyl]pyridinium iodide 1-Ethyl-4-[[[3-(1,1-dimethylethyl)-4-(dodecyloxy)benzoyl]amino]methyl]pyridinium iodide 1-Ethyl-4-[[[2-chloro-4-(tetradecyloxy)benzoyl]amino]methyl]pyridinium iodide 1-Ethyl-4-[[[2-chloro-4-(dodecyloxy)benzoyl]amino]methyl]pyridinium iodide 1-Ethyl-4-[[[2-chloro-3-(tetradecyloxy)benzoyl]amino]methyl]pyridinium iodide 1-Ethyl-4-[[[2-methoxy-4-(hexadecyloxy)benzoyl]amino]methyl]pyridinium iodide 1-Ethyl-4-[[[2-methoxy-4-(decyloxy)benzoyl]amino]methyl]pyridinium iodide 1-Ethyl-4-[[[[3-chloro-4-(tetradecyloxy)phenyl]acetyl]amino]methyl]pyridinium iodide 1-Ethyl-4-[[[[3-chloro-4-(dodecyloxy)phenyl]acetyl]amino]methyl]pyridinium iodide 1-Ethyl-4-[[[[3-methoxy-4-(tetradecyloxy)phenyl]acetyl]amino]methyl]pyridinium iodide 1-Ethyl-4-[[[[3-methoxy-4-(dodecyloxy)phenyl]acetyl]amino]methyl]pyridinium iodide 1-Ethyl-4-[[[[3-(1,1-dimethylethyl)-4-(tetradecyloxy)phenyl]acetyl]amino]methyl]pyridinium iodide 1-Ethyl-4-[[[[3-(1,1-dimethylethyl)-4-(dodecyloxy)phenyl]acetyl]amino]methyl]pyridinium iodide 1-Ethyl-4-[[[[2-chloro-4-(tetradecyloxy)phenyl]acetyl]amino]methyl]pyridinium iodide 1-Ethyl-4-[[[[2-chloro-4-(dodecyloxy)phenyl]acetyl]amino]methyl]pyridinium iodide 1-Ethyl-4-[[[[2-chloro-3-(tetradecyloxy)phenyl]acetyl]amino]methyl]pyridinium iodide 1-Ethyl-4-[[[[2-methoxy-4-(hexadecyloxy)phenyl]acetyl]amino]methyl]pyridinium iodide 1-Ethyl-4-[[[[2-methoxy-4-(decyloxy)phenyl]acetyl]amino]methyl]pyridinium iodide 1-Ethyl-4-[2-[[[3-chloro-4-(tetradecyloxy)phenoxy]acetyl]amino]ethyl]pyridinium iodide 1-Ethyl-4-[2-[[[3-chloro-4-(dodecyloxy)phenoxy]acetyl]amino]ethyl]pyridinium iodide 1-Ethyl-4-[2-[[[3-methoxy-4-(tetradecyloxy)phenoxy]acetyl]amino]ethyl]pyridinium iodide 1-Ethyl-4-[2-[[[3-methoxy-4-(dodecyloxy)phenoxy]acetyl]amino]ethyl]pyridinium iodide 1-Ethyl-4-[2-[[[3-(1,1-dimethylethyl)-4-(tetradecyloxy)phenoxy]acetyl]amino]ethyl]pyridinium iodide 1-Ethyl-4-[2-[[[3-(1,1-dimethylethyl)-4-(dodecyloxy)phenoxy]acetyl]amino]ethyl]pyridinium iodide 1-Ethyl-4-[2-[[[2-chloro-4-(tetradecyloxy)phenoxy]acetyl]amino]ethyl]pyridinium iodide 1-Ethyl-4-[2-[[[2-chloro-4-(dodecyloxy)phenoxy]acetyl]amino]ethyl]pyridinium iodide 1-Ethyl-4-[2-[[[2-chloro-3-(tetradecyloxy)phenoxy]acetyl]amino]ethyl]pyridinium iodide 1-Ethyl-4-[2-[[[2-methoxy-4-(hexadecyloxy)phenoxy]acetyl]amino]ethyl]pyridinium iodide 1-Ethyl-4-[2-[[[2-methoxy-4-(decyloxy)phenoxy]acetyl]amino]ethyl]pyridinium iodide 1-Propyl-2-[[[3-chloro-4-(tetradecyloxy)benzoyl]amino]methyl]pyridinium iodide 1-Propyl-2-[[[3-chloro-4-(dodecyloxy)benzoyl]amino]methyl]pyridinium iodide 1-Propyl-2-[[[3-methoxy-4-(tetradecyloxy)benzoyl]amino]methyl]pyridinium iodide 1-Propyl-2-[[[3-methoxy-4-(dodecyloxy)benzoyl]amino]methyl]pyridinium iodide 1-Propyl-2-[[[3-(1,1-dimethylethyl)-4-(tetradecyloxy)benzoyl]amino]methyl]pyridinium iodide 1-Propyl-2-[[[3-(1,1-dimethylethyl)-4-(dodecyloxy)benzoyl]amino]methyl]pyridinium iodide 1-Propyl-2-[[[2-chloro-4-(tetradecyloxy)benzoyl]amino]methyl]pyridinium iodide 1-Propyl-2-[[[2-chloro-4-(dodecyloxy)benzoyl]amino]methyl]pyridinium iodide 1-Propyl-2-[[[2-chloro-3-(tetradecyloxy)benzoyl]amino]methyl]pyridinium iodide 1-Propyl-2-[[[2-methoxy-4-(hexadecyloxy)benzoyl]amino]methyl]pyridinium iodide 1-Propyl-2-[[[2-methoxy-4-(decyloxy)benzoyl]amino]methyl]pyridinium iodide 1-Propyl-2-[[[[3-chloro-4-(tetradecyloxy)phenyl]acetyl]amino]methyl]pyridinium iodide 1-Propyl-2-[[[[3-chloro-4-(dodecyloxy)phenyl]acetyl]amino]methyl]pyridinium iodide 1-Propyl-2-[[[[3-methoxy-4-(tetradecyloxy)phenyl]acetyl]amino]methyl]pyridinium iodide 1-Propyl-2-[[[[3-methoxy-4-(dodecyloxy)phenyl]acetyl]amino]methyl]pyridinium iodide 1-Propyl-2-[[[[3-(1,1-dimethylethyl)-4-(tetradecyloxy)phenyl]acetyl]amino]methyl]pyridinium iodide 1-Propyl-2-[[[[3-(1,1-dimethylethyl)-4-(dodecyloxy)phenyl]acetyl]amino]methyl]pyridinium iodide 1-Propyl-2-[[[[2-chloro-4-(tetradecyloxy)phenyl]acetyl]amino]methyl]pyridinium iodide 1-Propyl-2-[[[[2-chloro-4-(dodecyloxy)phenyl]acetyl]amino]methyl]pyridinium iodide 1-Propyl-2-[[[[2-chloro-3-(tetradecyloxy)phenyl]acetyl]amino]methyl]pyridinium iodide 1-Propyl-2-[[[[2-methoxy-4-(hexadecyloxy)phenyl]acetyl]amino]methyl]pyridinium iodide 1-Propyl-2-[[[[2-methoxy-4-(decyloxy)phenyl]acetyl]amino]methyl]pyridinium iodide 1-Propyl-2-[2-[[[3-chloro-4-(tetradecyloxy)phenoxy]acetyl]amino]ethyl]pyridinium iodide 1-Propyl-2-[2-[[[3-chloro-4-(dodecyloxy)phenoxy]acetyl]amino]ethyl]pyridinium iodide 1-Propyl-2-[2-[[[3-methoxy-4-(tetradecyloxy)phenoxy]acetyl]amino]ethyl]pyridinium iodide 1-Propyl-2-[2-[[[3-methoxy-4-(dodecyloxy)phenoxy]acetyl]amino]ethyl]pyridinium iodide 1-Propyl-2-[2-[[[3-(1,1-dimethylethyl)-4-(tetradecyloxy)phenoxy]acetyl]amino]ethyl]pyridinium iodide 1-Propyl-2-[2-[[[3-(1,1-dimethylethyl)-4-(dodecyloxy)phenoxy]acetyl]amino]ethyl]pyridinium iodide 1-Propyl-2-[2-[[[2-chloro-4-(tetradecyloxy)phenoxy]acetyl]amino]ethyl]pyridinium iodide 1-Propyl-2-[2-[[[2-chloro-4-(dodecyloxy)phenoxy]acetyl]amino]ethyl]pyridinium iodide 1-Propyl-2-[2-[[[2-chloro-3-(tetradecyloxy)phenoxy]acetyl]amino]ethyl]pyridinium iodide 1-Propyl-2-[2-[[[2-methoxy-4-(hexadecyloxy)phenoxy]acetyl]amino]ethyl]pyridinium iodide 1-Propyl-2-[2-[[[2-methoxy-4-(decyloxy)phenoxy]acetyl]amino]ethyl]pyridinium iodide 1-Propyl-3-[[[3-chloro-4-(tetradecyloxy)benzoyl]amino]methyl]pyridinium iodide 1-Propyl-3-[[[3-chloro-4-(dodecyloxy)benzoyl]amino]methyl]pyridinium iodide 1-Propyl-3-[[[3-methoxy-4-(tetradecyloxy)benzoyl]amino]methyl]pyridinium iodide 1-Propyl-3-[[[3-methoxy-4-(dodecyloxy)benzoyl]amino]methyl]pyridinium iodide 1-Propyl-3-[[[3-(1,1-dimethylethyl)-4-(tetradecyloxy)benzoyl]amino]methyl]pyridinium iodide 1-Propyl-3-[[[3-(1,1-dimethylethyl)-4-(dodecyloxy)benzoyl]amino]methyl]pyridinium iodide 1-Propyl-3-[[[2-chloro-4-(tetradecyloxy)benzoyl]amino]methyl]pyridinium iodide 1-Propyl-3-[[[2-chloro-4-(dodecyloxy)benzoyl]amino]methyl]pyridinium iodide 1-Propyl-3-[[[2-chloro-3-(tetradecyloxy)benzoyl]amino]methyl]pyridinium iodide 1-Propyl-3-[[[2-methoxy-4-(hexadecyloxy)benzoyl]amino]methyl]pyridinium iodide 1-Propyl-3-[[[2-methoxy-4-(decyloxy)benzoyl]amino]methyl]pyridinium iodide 1-Propyl-3-[[[[3-chloro-4-(tetradecyloxy)phenyl]acetyl]amino]methyl]pyridinium iodide 1-Propyl-3-[[[[3-chloro-4-(dodecyloxy)phenyl]acetyl]amino]methyl]pyridinium iodide 1-Propyl-3-[[[[3-methoxy-4-(dodecyloxy)phenyl]acetyl]amino]methyl]pyridinium iodide 1-Propyl-3-[[[[3-(1,1-dimethylethyl)-4-(tetradecyloxy)phenyl]acetyl]amino]methyl]pyridinium iodide 1-Propyl-3-[[[[3-(1,1-dimethylethyl)-4-(dodecyloxy)phenyl]acetyl]amino]methyl]pyridinium iodide 1-Propyl-3-[[[[2-chloro-4-(tetradecyloxy)phenyl]acetyl]amino]methyl]pyridinium iodide 1-Propyl-3-[[[[2-chloro-4-(dodecyloxy)phenyl]acetyl]amino]methyl]pyridinium iodide 1-Propyl-3-[[[[2-chloro-3-(tetradecyloxy)phenyl]acetyl]amino]methyl]pyridinium iodide 1-Propyl-3-[[[[2-methoxy-4-(hexadecyloxy)phenyl]acetyl]amino]methyl]pyridinium iodide 1-Propyl-3-[[[[2-methoxy-4-(decyloxy)phenyl]acetyl]amino]methyl]pyridinium iodide 1-Propyl-3-[2-[[[3-chloro-4-(tetradecyloxy)phenoxy]acetyl]amino]ethyl]pyridinium iodide 1-Propyl-3-[2-[[[3-chloro-4-(dodecyloxy)phenoxy]acetyl]amino]ethyl]pyridinium iodide 1-Propyl-3-[2-[[[3-methoxy-4-(tetradecyloxy)phenoxy]acetyl]amino]ethyl]pyridinium iodide 1-Propyl-3-[2-[[[3-methoxy-4-(dodecyloxy)phenoxy]acetyl]amino]ethyl]pyridinium iodide 1-Propyl-3-[2-[[[3-(1,1-dimethylethyl)-4-(tetradecyloxy)phenoxy]acetyl]amino]ethyl]pyridinium iodide 1-Propyl-3-[2-[[[3-(1,1-dimethylethyl)-4-(dodecyloxy)phenoxy]acetyl]amino]ethyl]pyridinium iodide 1-Propyl-3-[2-[[[2-chloro-4-(tetradecyloxy)phenoxy]acetyl]amino]ethyl]pyridinium iodide 1-Propyl-3-[2-[[[2-chloro-4-(dodecyloxy)phenoxy]acetyl]amino]ethyl]pyridinium iodide 1-Propyl-3-[2-[[[2-chloro-3-(tetradecyloxy)phenoxy]acetyl]amino]ethyl]pyridinium iodide 1-Propyl-3-[2-[[[2-methoxy-4-(hexadecyloxy)phenoxy]acetyl]amino]ethyl]pyridinium iodide 1-Propyl-3-[2-[[[2-methoxy-4-(decyloxy)phenoxy]acetyl]amino]ethyl]pyridinium iodide 1-Propyl-4-[[[3-chloro-4-(tetradecyloxy)benzoyl]amino]methyl]pyridinium iodide 1-Propyl-4-[[[3-chloro-4-(dodecyloxy)benzoyl]amino]methyl]pyridinium iodide 1-Propyl-4-[[[3-methoxy-4-(tetradecyloxy)benzoyl]amino]methyl]pyridinium iodide 1-Propyl-4-[[[3-methoxy-4-(dodecyloxy)benzoyl]amino]methyl]pyridinium iodide 1-Propyl-4-[[[3-(1,1-dimethylethyl)-4-(tetradecyloxy)benzoyl]amino]methyl]pyridinium iodide 1-Propyl-4-[[[3-(1,1-dimethylethyl)-4-(dodecyloxy)benzoyl]amino]methyl]pyridinium iodide 1-Propyl-4-[[[2-chloro-4-(tetradecyloxy)benzoyl]amino]methyl]pyridinium iodide 1-Propyl-4-[[[2-chloro-3-(tetradecyloxy)benzoyl]amino]methyl]pyridinium iodide 1-Propyl-4-[[[2-methoxy-4-(hexadecyloxy)benzoyl]amino]methyl]pyridinium iodide 1-Propyl-4-[[[2-methoxy-4-(decyloxy)benzoyl]amino]methyl]pyridinium iodide 1-Propyl-4-[[[[3-chloro-4-(tetradecyloxy)phenyl]acetyl]amino]methyl]pyridinium iodide 1-Propyl-4-[[[[3-chloro-4-(dodecyloxy)phenyl]acetyl]amino]methyl]pyridinium iodide 1-Propyl-4-[[[[3-methoxy-4-(tetradecyloxy)phenyl]acetyl]amino]methyl]pyridinium iodide 1-Propyl-4-[[[[3-methoxy-4-(dodecyloxy)phenyl]acetyl]amino]methyl]pyridinium iodide 1-Propyl-4-[[[[3-(1,1-dimethylethyl)-4-(tetradecyloxy)phenyl]acetyl]amino]methyl]pyridinium iodide 1-Propyl-4-[[[[3-(1,1-dimethylethyl)-4-(dodecyloxy)phenyl]acetyl]amino]methyl]pyridinium iodide 1-Propyl-4-[[[[2-chloro-4-(tetradecyloxy)phenyl]acetyl]amino]methyl]pyridinium iodide 1-Propyl-4-[[[[2-chloro-3-(tetradecyloxy)phenyl]acetyl]amino]methyl]pyridinium iodide 1-Propyl-4-[[[[2-methoxy-4-(hexadecyloxy)phenyl]acetyl]amino]methyl]pyridinium iodide 1-Propyl-4-[[[[2-methoxy-4-(decyloxy)phenyl]acetyl]amino]methyl]pyridinium iodide 1-Propyl-4-[2-[[[3-chloro-4-(tetradecyloxy)phenoxy]acetyl]amino]ethyl]pyridinium iodide 1-Propyl-4-[2-[[[3-chloro-4-(dodecyloxy)phenoxy]acetyl]amino]ethyl]pyridinium iodide 1-Propyl-4-[2-[[[3-methoxy-4-(tetradecyloxy)phenoxy]acetyl]amino]ethyl]pyridinium iodide 1-Propyl-4-[2-[[[3-methoxy-4-(dodecyloxy)phenoxy]acetyl]amino]ethyl]pyridinium iodide 1-Propyl-4-[2-[[[3-(1,1-dimethylethyl)-4-(tetradecyloxy)phenoxy]acetyl]amino]ethyl]pyridinium iodide 1-Propyl-4-[2-[[[3-(1,1-dimethylethyl)-4-(dodecyloxy)phenoxy]acetyl]amino]ethyl]pyridinium iodide 1-Propyl-4-[2-[[[2-chloro-4-(tetradecyloxy)phenoxy]acetyl]amino]ethyl]pyridinium iodide 1-Propyl-4-[2-[[[2-chloro-4-(dodecyloxy)phenoxy]acetyl]amino]ethyl]pyridinium iodide 1-Propyl-4-[2-[[[2-chloro-3-(tetradecyloxy)phenoxy]acetyl]amino]ethyl]pyridinium iodide 1-Propyl-4-[2-[[[2-methoxy-4-(hexadecyloxy)phenoxy]acetyl]amino]ethyl]pyridinium iodide 1-Propyl-4-[2-[[[2-methoxy-3-(tetradecyloxy)phenoxy]acetyl]amino]ethyl]pyridinium iodide According to the methods outlined hereinabove in Flowsheets A, B, C, D, and E, and described in detail in Examples 1-9, 12-19, 21, 23, 24, 26-54, 56, 58, 60-68, 84-88, 90, 91, 98, 102-107, 109-113, 130-140, and 144, the compounds of this invention listed hereinbelow in List 2 can be prepared. These methods are applicable to the preparation of compounds of this invention by one skilled in the art.

List 2

2-[[Acetyl[3-(1,1-dimethylethyl)-4-(tetradecyloxy)benzoyl]amino]methyl]-1-methylpyridinium iodide 2-[[Acetyl[3-(1,1-dimethylethyl)-4-(tetradecyloxy)benzoyl]amino]methyl]-1-propylpyridinium iodide 2-[[Acetyl[3-(1,1-dimethylethyl)-4-(hexadecyloxy)benzoyl]amino]methyl]-1-ethylpyridinium iodide 2-[[Acetyl[3-(1,1-dimethylethyl)-4-(dodecyloxy)benzoyl]amino]methyl]-1-methylpyridinium iodide 2-[[Acetyl[3-(1,1-dimethylethyl)-4-(dodecyloxy)benzoyl]amino]methyl]-1-propylpyridinium iodide 2-[[Acetyl[3-methoxy-4-(tetradecyloxy)benzoyl]amino]methyl]-1-ethylpyridinium iodide 2-[[Acetyl[3-methoxy-4-(hexadecyloxy)benzoyl]amino]methyl]-1-methylpyridinium iodide 2-[[Acetyl[3-methoxy-4-(hexadecyloxy)benzoyl]amino]methyl]-1-propylpyridinium iodide 2-[[Acetyl[3-methoxy-4-(dodecyloxy)benzoyl]amino]methyl]-1-ethylpyridinium iodide 2-[[Acetyl[2-methyl-4-(tetradecyloxy)benzoyl]amino]methyl]-1-methylpyridinium iodide 2-[[Acetyl[2-methyl-4-(tetradecyloxy)benzoyl]amino]methyl]-1-propylpyridinium iodide 2-[[Acetyl[2-methyl-4-(hexadecyloxy)benzoyl]amino]methyl]-1-ethylpyridinium iodide 2-[[Acetyl[2-methyl-3-(tetradecyloxy)benzoyl]amino]methyl]-1-methylpyridinium iodide 2-[[Acetyl[2-methyl-3-(tetradecyloxy)benzoyl]amino]methyl]-1-propylpyridinium iodide 2-[[Acetyl[2-methyl-4-(dodecyloxy)benzoyl]amino]methyl]-1-ethylpyridinium iodide 2-[[Acetyl[4-methoxy-3-(tetradecyloxy)benzoyl]amino]methyl]-1-methylpyridinium iodide 2-[[Acetyl[4-methoxy-3-(tetradecyloxy)benzoyl]amino]methyl]-1-propylpyridinium iodide 2-[[Acetyl[3-chloro-4-(tetradecyloxy)benzoyl]amino]methyl]-1-methylpyridinium iodide 2-[[Acetyl[3-chloro-4-(tetradecyloxy)benzoyl]amino]methyl]-1-propylpyridinium iodide 2-[[Acetyl[3-chloro-4-(hexadecyloxy)benzoyl]amino]methyl]-1-ethylpyridinium iodide 2-[[Acetyl[3-chloro-4-(dodecyloxy)benzoyl]amino]methyl]-1-methylpyridinium iodide 2-[[Acetyl[3-chloro-4-(dodecyloxy)benzoyl]amino]methyl]-1-propylpyridinium iodide 2-[[Acetyl[3,4-bis(heptyloxy)benzoyl]amino]methyl]-1-ethylpyridinium iodide 2-[[Acetyl[3,4-bis(tetradecyloxy)benzoyl]amino]methyl]-1-methylpyridinium iodide 2-[[Acetyl[3,4-bis(tetradecyloxy)benzoyl]amino]methyl]-1-propylpyridinium iodide 2-[[Acetyl[[3-(1,1-dimethylethyl)-4-(tetradecyloxy)phenoxy]acetyl]amino]methyl]-1-ethylpyridinium iodide 2-[[Acetyl[[3-(1,1-dimethylethyl)-4-(hexadecyloxy)phenoxy]acetyl]amino]methyl]-1-methylpyridinium iodide 2-[[Acetyl[[3-(1,1-dimethylethyl)-4-(hexadecyloxy)phenoxy]acetyl]amino]methyl]-1-propylpyridinium iodide 2-[[Acetyl[[3-(1,1-dimethylethyl)-4-(dodecyloxy)phenoxy]acetyl]amino]methyl]-1-ethylpyridinium iodide 2-[[Acetyl[[3-methoxy-4-(tetradecyloxy)phenoxy]acetyl]amino]methyl]-1-methylpyridinium iodide 2-[[Acetyl[[3-methoxy-4-(tetradecyloxy)phenoxy]acetyl]amino]methyl]-1-propylpyridinium iodide 2-[[Acetyl[[3-methoxy-4-(hexadecyloxy)phenoxy]acetyl]amino]methyl]-1-ethylpyridinium iodide 2-[[Acetyl[[3-methoxy-4-(dodecyloxy)phenoxy]acetyl]amino]methyl]-1-methylpyridinium iodide 2-[[Acetyl[[3-methoxy-4-(dodecyloxy)phenoxy]acetyl]amino]methyl]-1-propylpyridinium iodide 2-[[Acetyl[[2-methyl-4-(tetradecyloxy)phenoxy]acetyl]amino]methyl]-1-ethylpyridinium iodide 2-[[Acetyl[[2-methyl-4-(hexadecyloxy)phenoxy]acetyl]amino]methyl]-1-methylpyridinium iodide 2-[[Acetyl[[2-methyl-4-(hexadecyloxy)phenoxy]acetyl]amino]methyl]-1-propylpyridinium iodide 2-[[Acetyl[[2-methyl-3-(tetradecyloxy)phenoxy]acetyl]amino]methyl]-1-ethylpyridinium iodide 2-[[Acetyl[[2-methyl-4-(dodecyloxy)phenoxy]acetyl]amino]methyl]-1-methylpyridinium iodide 2-[[Acetyl[[2-methyl-4-(dodecyloxy)phenoxy]acetyl]amino]methyl]-1-propylpyridinium iodide 2-[[Acetyl[[4-methoxy-3-(tetradecyloxy)phenoxy]acetyl]amino]methyl]-1-ethylpyridinium iodide 2-[[Acetyl[[3-chloro-4-(tetradecyloxy)phenoxy]acetyl]amino]methyl]-1-ethylpyridinium iodide 2-[[Acetyl[[3-chloro-4-(hexadecyloxy)phenoxy]acetyl]amino]methyl]-1-methylpyridinium iodide 2-[[Acetyl[[3-chloro-4-(hexadecyloxy)phenoxy]acetyl]amino]methyl]-1-propylpyridinium iodide 2-[[Acetyl[[3-chloro-4-(dodecyloxy)phenoxy]acetyl]amino]methyl]-1-ethylpyridinium iodide 2-[[Acetyl[[3,4-bis(heptyloxy)phenoxy]acetyl]amino]methyl]-1-methylpyridinium iodide 2-[[Acetyl[[3,4-bis(heptyloxy)phenoxy]acetyl]amino]methyl]-1-propylpyridinium iodide 2-[[Acetyl[[3,4-bis(tetradecyloxy)phenoxy]acetyl]amino]methyl]-1-ethylpyridinium iodide 2-[[(2-Methoxybenzoyl)[3-(1,1-dimethylethyl)-4-(tetradecyloxy)benzoyl]amino]methyl]-1-methylpyridinium iodide 2-[[(2-Methoxybenzoyl)[3-(1,1-dimethylethyl)-4-(tetradecyloxy)benzoyl]amino]methyl]-1-propylpyridinium iodide 2-[[(2-Methoxybenzoyl)[3-(1,1-dimethylethyl)-4-(hexadecyloxy)benzoyl]amino]methyl]-1-ethylpyridinium iodide 2-[[(2-Methoxybenzoyl)[3-(1,1-dimethylethyl)-4-(dodecyloxy)benzoyl]amino]methyl]-1-methylpyridinium iodide 2-[[(2-Methoxybenzoyl)[3-(1,1-dimethylethyl)-4-(dodecyloxy)benzoyl]amino]methyl]-1-propylpyridinium iodide 2-[[(2-Methoxybenzoyl)[3-methoxy-4-(tetradecyloxy)benzoyl]amino]methyl]-1-ethylpyridinium iodide 2-[[(2-Methoxybenzoyl)[3-methoxy-4-(hexadecyloxy)benzoyl]amino]methyl]-1-methylpyridinium iodide 2-[[(2-Methoxybenzoyl)[3-methoxy-4-(hexadecyloxy)benzoyl]amino]methyl]-1-propylpyridinium iodide 2-[[(2-Methoxybenzoyl)[3-methoxy-4-(dodecyloxy)benzoyl]amino]methyl]-1-ethylpyridinium iodide 2-[[(2-Methoxybenzoyl)[2-methyl-4-(tetradecyloxy)benzoyl]amino]methyl]-1-methylpyridinium iodide 2-[[(2-Methoxybenzoyl)[2-methyl-4-(tetradecyloxy)benzoyl]amino]methyl]-1-propylpyridinium iodide 2-[[(2-Methoxybenzoyl)[2-methyl-4-(hexadecyloxy)benzoyl]amino]methyl]-1-ethylpyridinium iodide 2-[[(2-Methoxybenzoyl)[2-methyl-3-(tetradecyloxy)benzoyl]amino]methyl]-1-methylpyridinium iodide 2-[[(2-Methoxybenzoyl)[2-methyl-3-(tetradecyloxy)benzoyl]amino]methyl]-1-propylpyridinium iodide 2-[[(2-Methoxybenzoyl)[2-methyl-4-(dodecyloxy)benzoyl]amino]methyl]-1-ethylpyridinium iodide 2-[[(2-Methoxybenzoyl)[4-methoxy-3-(tetradecyloxy)benzoyl]amino]methyl]-1-methylpyridinium iodide 2-[[(2-Methoxybenzoyl)[4-methoxy-3-(tetradecyloxy)benzoyl]amino]methyl]-1-propylpyridinium iodide 2-[[(2-Methoxybenzoyl)[3-chloro-4-(tetradecyloxy)benzoyl]amino]methyl]-1-methylpyridinium iodide 2-[[(2-Methoxybenzoyl)[3-chloro-4-(tetradecyloxy)benzoyl]amino]methyl]-1-propylpyridinium iodide 2-[[(2-Methoxybenzoyl)[3-chloro-4-(hexadecyloxy)benzoyl]amino]methyl]-1-ethylpyridinium iodide 2-[[(2-Methoxybenzoyl)[3-chloro-4-(dodecyloxy)benzoyl]amino]methyl]-1-methylpyridinium iodide 2-[[(2-Methoxybenzoyl)[3-chloro-4-(dodecyloxy)benzoyl]amino]methyl]-1-propylpyridinium iodide 2-[[(2-Methoxybenzoyl)[3,4-bis(heptyloxy)benzoyl]amino]methyl]-1-ethylpyridinium iodide 2-[[(2-Methoxybenzoyl)[3,4-bis(tetradecyloxy)benzoyl]amino]methyl]-1-methylpyridinium iodide 2-[[(2-Methoxybenzoyl)[3,4-bis(tetradecyloxy)benzoyl]amino]methyl]-1-propylpyridinium iodide 2-[2-[Acetyl[3-(1,1-dimethylethyl)-4-(tetradecyloxy)benzoyl]amino]ethyl]-1-ethylpyridinium iodide 2-[2-[Acetyl[3-(1,1-dimethylethyl)-4-(hexadecyloxy)benzoyl]amino]ethyl]-1-methylpyridinium iodide 2-[2-[Acetyl[3-(1,1-dimethylethyl)-4-(hexadecyloxy)benzoyl]amino]ethyl]-1-propylpyridinium iodide 2-[2-[Acetyl[3-(1,1-dimethylethyl)-4-(dodecyloxy)benzoyl]amino]ethyl]-1-ethylpyridinium iodide 2-[2-[Acetyl[3-methoxy-4-(tetradecyloxy)benzoyl]amino]ethyl]-1-methylpyridinium iodide 2-[2-[Acetyl[3-methoxy-4-(tetradecyloxy)benzoyl]amino]ethyl]-1-propylpyridinium iodide 2-[2-[Acetyl[3-methoxy-4-(hexadecyloxy)benzoyl]amino]ethyl]-1-ethylpyridinium iodide 2-[2-[Acetyl[3-methoxy-4-(dodecyloxy)benzoyl]amino]ethyl]-1-methylpyridinium iodide 2-[2-[Acetyl[3-methoxy-4-(dodecyloxy)benzoyl]amino]ethyl]-1-propylpyridinium iodide 2-[2-[Acetyl[2-methyl-4-(tetradecyloxy)benzoyl]amino]ethyl]-1-ethylpyridinium iodide 2-[2-[Acetyl[2-methyl-4-(hexadecyloxy)benzoyl]amino]ethyl]-1-methylpyridinium iodide 2-[2-[Acetyl[2-methyl-4-(hexadecyloxy)benzoyl]amino]ethyl]-1-propylpyridinium iodide 2-[2-[Acetyl[2-methyl-3-(tetradecyloxy)benzoyl]amino]ethyl]-1-ethylpyridinium iodide 2-[2-[Acetyl[2-methyl-4-(dodecyloxy)benzoyl]amino]ethyl]-1-methylpyridinium iodide 2-[2-[Acetyl[2-methyl-4-(dodecyloxy)benzoyl]amino]ethyl]-1-propylpyridinium iodide 2-[2-[Acetyl[4-methoxy-3-(tetradecyloxy)benzoyl]amino]ethyl]-1-ethylpyridinium iodide 2-[2-[Acetyl[3-chloro-4-(tetradecyloxy)benzoyl]amino]ethyl]-1-ethylpyridinium iodide 2-[2-[Acetyl[3-chloro-4-(hexadecyloxy)benzoyl]amino]ethyl]-1-methylpyridinium iodide 2-[2-[Acetyl[3-chloro-4-(hexadecyloxy)benzoyl]amino]ethyl]-1-propylpyridinium iodide 2-[2-[Acetyl[3-chloro-4-(dodecyloxy)benzoyl]amino]ethyl]-1-ethylpyridinium iodide 2-[2-[Acetyl[3,4-bis(heptyloxy)benzoyl]amino]ethyl]-1-methylpyridinium iodide 2-[2-[Acetyl[3,4-bis(heptyloxy)benzoyl]amino]ethyl]-1-propylpyridinium iodide -{2-[Acetyl[3,4-bis(tetradecyloxy)benzoyl]amino]ethyl]-1-ethylpyridinium iodide 2-[3-[Acetyl[3-(1,1-dimethylethyl)-4-(tetradecyloxy)benzoyl]amino]propyl]-1-methylpyridinium iodide 2-[3-[Acetyl[3-(1,1-dimethylethyl)-4-(tetradecyloxy)benzoyl]amino]propyl]-1-propylpyridinium iodide 2-[3-[Acetyl[3-(1,1-dimethylethyl)-4-(hexadecyloxy)benzoyl]amino]propyl]-1-ethylpyridinium iodide 2-[3-[Acetyl[3-(1,1-dimethylethyl)-4-(dodecyloxy)benzoyl]amino]propyl]-1-methylpyridinium iodide 2-[3-[Acetyl[3-(1,1-dimethylethyl)-4-(dodecyloxy)benzoyl]amino]propyl]-1-propylpyridinium iodide 2-[3-[Acetyl[3-methoxy-4-(tetradecyloxy)benzoyl]amino]propyl]-1-ethylpyridinium iodide 2-[3-[Acetyl[3-methoxy-4-(hexadecyloxy)benzoyl]amino]propyl]-1-methylpyridinium iodide 2-[3-[Acetyl[3-methoxy-4-(hexadecyloxy)benzoyl]amino]propyl]-1-propylpyridinium iodide 2-[3-[Acetyl[3-methoxy-4-(dodecyloxy)benzoyl]amino]propyl]-1-ethylpyridinium iodide 2-[3-[Acetyl[2-methyl-4-(tetradecyloxy)benzoyl]amino]propyl]-1-methylpyridinium iodide 2-[3-[Acetyl[2-methyl-4-(tetradecyloxy)benzoyl]amino]propyl]-1-propylpyridinium iodide 2-[3-[Acetyl[2-methyl-4-(hexadecyloxy)benzoyl]amino]propyl]-1-ethylpyridinium iodide 2-[3-[Acetyl[2-methyl-3-(tetradecyloxy)benzoyl]amino]propyl]-1-methylpyridinium iodide 2-[3-[Acetyl[2-methyl-3-(tetradecyloxy)benzoyl]amino]propyl]-1-propylpyridinium iodide 2-[3-[Acetyl[2-methyl-4-(dodecyloxy)benzoyl]amino]propyl]-1-ethylpyridinium iodide 2-[3-[Acetyl[4-methoxy-3-(tetradecyloxy)benzoyl]amino]propyl]-1-methylpyridinium iodide 2-[3-[Acetyl[4-methoxy-3-(tetradecyloxy)benzoyl]amino]propyl]-1-propylpyridinium iodide 2-[3-[Acetyl[3-chloro-4-(tetradecyloxy)benzoyl]amino]propyl]-1-methylpyridinium iodide 2-[3-[Acetyl[3-chloro-4-(tetradecyloxy)benzoyl]amino]propyl]-1-propylpyridinium iodide 2-[3-[Acetyl[3-chloro-4-(hexadecyloxy)benzoyl]amino]propyl]-1-ethylpyridinium iodide 2-[3-[Acetyl[3-chloro-4-(dodecyloxy)benzoyl]amino]propyl]-1-methylpyridinium iodide 2-[3-[Acetyl[3-chloro-4-(dodecyloxy)benzoyl]amino]propyl]-1-propylpyridinium iodide 2-[3-[Acetyl[3,4-bis(heptyloxy)benzoyl]amino]propyl]-1-ethylpyridinium iodide 2-[3-[Acetyl[3,4-bis(tetradecyloxy)benzoyl]amino]propyl]-1-methylpyridinium iodide 2-[3-[Acetyl[3,4-bis(tetradecyloxy)benzoyl]amino]propyl]-1-propylpyridinium iodide 2-[[Benzoyl[3-(1,1-dimethylethyl)-4-(tetradecyloxy)benzoyl]amino]methyl]-1-ethylpyridinium iodide 2-[[Benzoyl[3-(1,1-dimethylethyl)-4-(hexadecyloxy)benzoyl]amino]methyl]-1-methylpyridinium iodide 2-[[Benzoyl[3-(1,1-dimethylethyl)-4-(hexadecyloxy)benzoyl]amino]methyl]-1-propylpyridinium iodide 2-[[Benzoyl[3-(1,1-dimethylethyl)-4-(dodecyloxy)benzoyl]amino]methyl]-1-ethylpyridinium iodide 2-[[Benzoyl[3-methoxy-4-(tetradecyloxy)benzoyl]amino]methyl]-1-methylpyridinium iodide 2-[[Benzoyl[3-methoxy-4-(tetradecyloxy)benzoyl]amino]methyl]-1-propylpyridinium iodide 2-[[Benzoyl[3-methoxy-4-(hexadecyloxy)benzoyl]amino]methyl]-1-ethylpyridinium iodide 2-[[Benzoyl[3-methoxy-4-(dodecyloxy)benzoyl]amino]methyl]-1-methylpyridinium iodide 2-[[Benzoyl[3-methoxy-4-(dodecyloxy)benzoyl]amino]methyl]-1-ethylpyridinium iodide 2-[[Benzoyl[3-methoxy-4-(dodecyloxy)benzoyl]amino]methyl]-1-propylpyridinium iodide 2-[[Benzoyl[2-methyl-4-(tetradecyloxy)benzoyl]amino]methyl]-1-methylpyridinium iodide 2-[[Benzoyl[2-methyl-4-(tetradecyloxy)benzoyl]amino]methyl]-1-ethylpyridinium iodide 2-[[Benzoyl[2-methyl-4-(tetradecyloxy)benzoyl]amino]methyl]-1-propylpyridinium iodide 2-[[Benzoyl[2-methyl-4-(hexadecyloxy)benzoyl]amino]methyl]-1-methylpyridinium iodide 2-[[Benzoyl[2-methyl-4-(hexadecyloxy)benzoyl]amino]methyl]-1-ethylpyridinium iodide 2-[[Benzoyl[2-methyl-4-(hexadecyloxy)benzoyl]amino]methyl]-1-propylpyridinium iodide 2-[[Benzoyl[2-methyl-3-(tetradecyloxy)benzoyl]amino]methyl]-1-methylpyridinium iodide 2-[[Benzoyl[2-methyl-3-(tetradecyloxy)benzoyl]amino]methyl]-1-ethylpyridinium iodide 2-[[Benzoyl[2-methyl-3-(tetradecyloxy)benzoyl]amino]methyl]-1-propylpyridinium iodide 2-[[Benzoyl[2-methyl-4-(dodecyloxy)benzoyl]amino]methyl]-1-methylpyridinium iodide 2-[[Benzoyl[2-methyl-4-(dodecyloxy)benzoyl]amino]methyl]-1-ethylpyridinium iodide 2-[[Benzoyl[2-methyl-4-(dodecyloxy)benzoyl]amino]methyl]-1-propylpyridinium iodide 2-[[Benzoyl[4-methoxy-3-(tetradecyloxy)benzoyl]amino]methyl]-1-methylpyridinium iodide 2-[[Benzoyl[4-methoxy-3-(tetradecyloxy)benzoyl]amino]methyl]-1-ethylpyridinium iodide 2-[[Benzoyl[4-methoxy-3-(tetradecyloxy)benzoyl]amino]methyl]-1-propylpyridinium iodide 2-[[Benzoyl[3-chloro-4-(tetradecyloxy)benzoyl]amino]methyl]-1-methylpyridinium iodide 2-[[Benzoyl[3-chloro-4-(tetradecyloxy)benzoyl]amino]methyl]-1-ethylpyridinium iodide 2-[[Benzoyl[3-chloro-4-(tetradecyloxy)benzoyl]amino]methyl]-1-propylpyridinium iodide 2-[[Benzoyl[3-chloro-4-(hexadecyloxy)benzoyl]amino]methyl]-1-methylpyridinium iodide 2-[[Benzoyl[3-chloro-4-(hexadecyloxy)benzoyl]amino]methyl]-1-ethylpyridinium iodide 2-[[Benzoyl[3-chloro-4-(hexadecyloxy)benzoyl]amino]methyl]-1-propylpyridinium iodide 2-[[Benzoyl[3-chloro-4-(dodecyloxy)benzoyl]amino]methyl]-1-methylpyridinium iodide 2-[[Benzoyl[3-chloro-4-(dodecyloxy)benzoyl]amino]methyl]-1-ethylpyridinium iodide 2-[[Benzoyl[3-chloro-4-(dodecyloxy)benzoyl]amino]methyl]-1-propylpyridinium iodide 2-[[Benzoyl[3,4-bis(heptyloxy)benzoyl]amino]methyl]-1-methylpyridinium iodide 2-[[Benzoyl[3,4-bis(heptyloxy)benzoyl]amino]methyl]-1-ethylpyridinium iodide 2-[[Benzoyl[3,4-bis(heptyloxy)benzoyl]amino]methyl]-1-propylpyridinium iodide 2-[[Benzoyl[3,4-bis(tetradecyloxy)benzoyl]amino]methyl]-1-methylpyridinium iodide 2-[[Benzoyl[3,4-bis(tetradecyloxy)benzoyl]amino]methyl]-1-ethylpyridinium iodide 2-[[Benzoyl[3,4-bis(tetradecyloxy)benzoyl]amino]methyl]-1-propylpyridinium iodide According to the methods outlined hereinabove in Flowsheets A, F, and G, and described in detail in Examples 1, 2, 17-19, 21, 23, 24, 31, 32, 36, 37, 40-42, 46, 47, 51, 52, 60-64, 66, 67, 84-86, 94-97, 102-104, 109-110, and 130-131, the compounds of this invention listed hereinbelow in List 3 can be prepared. These methods are applicable to the preparation of the compounds of this invention by one skilled in the art.

List 3

2-[[Acetyl[[[3-(1,1-dimethylethyl)-4-(tetradecyloxy)phenyl]methoxy]carbonyl]amino]methyl]-1-methylpyridinium iodide 2-[[Acetyl[[[3-(1,1-dimethylethyl)-4-(tetradecyloxy)phenyl]methoxy]carbonyl]amino]methyl]-1-ethylpyridinium iodide 2-[[Acetyl[[[3-(1,1-dimethylethyl)-4-(tetradecyloxy)phenyl]methoxy]carbonyl]amino]methyl]-1-propylpyridinium iodide 2-[[Acetyl[[[3-methoxy-4-(tetradecyloxy)phenyl]methoxy]carbonyl]amino]methyl]-1-methylpyridinium iodide 2-[[Acetyl[[[3-methoxy-4-(tetradecyloxy)phenyl]methoxy]carbonyl]amino]methyl]-1-ethylpyridinium iodide 2-[[Acetyl[[[3-methoxy-4-(tetradecyloxy)phenyl]methoxy]carbonyl]amino]methyl]-1-propylpyridinium iodide 2-[[Acetyl[[[3-chloro-4-(tetradecyloxy)phenyl]methoxy]carbonyl]amino]methyl]-1-methylpyridinium iodide 2-[[Acetyl[[[3-chloro-4-(tetradecyloxy)phenyl]methoxy]carbonyl]amino]methyl]-1-ethylpyridinium iodide 2-[[Acetyl[[[3-chloro-4-(tetradecyloxy)phenyl]methoxy]carbonyl]amino]methyl]-1-propylpyridinium iodide 2-[[Acetyl[[[3,5-bis(methoxy)-4-(tetradecyloxy)phenyl]methoxy]carbonyl]amino]methyl]-1-methylpyridinium iodide 2-[[Acetyl[[[3,5-bis(methoxy)-4-(tetradecyloxy)phenyl]methoxy]carbonyl]amino]methyl]-1-ethylpyridinium iodide 2-[[Acetyl[[[3,5-bis(methoxy)-4-(tetradecyloxy)phenyl]methoxy]carbonyl]amino]methyl]-1-propylpyridinium iodide 2-[[Benzoyl[[[3-(1,1-dimethylethyl)-4-(tetradecyloxy)phenyl]methoxy]carbonyl]amino]methyl]-1-methylpyridinium iodide 2-[[Benzoyl[[[3-(1,1-dimethylethyl)-4-(tetradecyloxy)phenyl]methoxy]carbonyl]amino]methyl]-1-ethylpyridinium iodide 2-[[Benzoyl[[[3-(1,1-dimethylethyl)-4-(tetradecyloxy)phenyl]methoxy]carbonyl]amino]methyl]-1-propylpyridinium iodide 2-[[Benzoyl[[[3-methoxy-4-(tetradecyloxy)phenyl]methoxy]carbonyl]amino]methyl]-1-methylpyridinium iodide 2-[[Benzoyl[[[3-methoxy-4-(tetradecyloxy)phenyl]methoxy]carbonyl]amino]methyl]-1-ethylpyridinium iodide 2-[[Benzoyl[[[3-methoxy-4-(tetradecyloxy)phenyl]methoxy]carbonyl]amino]methyl]-1-propylpyridinium iodide 2-[[Benzoyl[[[3-chloro-4-(tetradecyloxy)phenyl]methoxy]carbonyl]amino]methyl]-1-methylpyridinium iodide 2-[[Benzoyl[[[3-chloro-4-(tetradecyloxy)phenyl]methoxy]carbonyl]amino]methyl]-1-ethylpyridinium iodide 2-[[Benzoyl[[[3-chloro-4-(tetradecyloxy)phenyl]methoxy]carbonyl]amino]methyl]-1-propylpyridinium iodide 2-[[Benzoyl[[[3,5-bis(methoxy)-4-(tetradecyloxy)phenyl]methoxy]carbonyl]amino]methyl]-1-methylpyridinium iodide 2-[[Benzoyl[[[3,5-bis(methoxy)-4-(tetradecyloxy)phenyl]methoxy]carbonyl]amino]methyl]-1-ethylpyridinium iodide 2-[[Benzoyl[[[3,5-bis(methoxy)-4-(tetradecyloxy)phenyl]methoxy]carbonyl]amino]methyl]-1-propylpyridinium iodide 2-[[(2-Methoxybenzoyl)[[[3-(1,1-dimethylethyl)-4-(tetradecyloxy)phenyl]methoxy]carbonyl]amino]methyl]-1-methylpyridinium iodide 2-[[(2-Methoxybenzoyl)[[[3-(1,1-dimethylethyl)-4-(tetradecyloxy)phenyl]methoxy]carbonyl]amino]methyl]-1-ethylpyridinium iodide 2-[[(2-Methoxybenzoyl)[[[3-(1,1-dimethylethyl)-4-(tetradecyloxy)phenyl]methoxy]carbonyl]amino]methyl]-1-propylpyridinium iodide 2-[[(2-Methoxybenzoyl)[[[3-methoxy-4-(tetradecyloxy)phenyl]methoxy]carbonyl]amino]methyl]-1-methylpyridinium iodide 2-[[(2-Methoxybenzoyl)[[[3-methoxy-4-(tetradecyloxy)phenyl]methoxy]carbonyl]amino]methyl]-1-ethylpyridinium iodide 2-[[(2-Methoxybenzoyl)[[[3-methoxy-4-(tetradecyloxy)phenyl]methoxy]carbonyl]amino]methyl]-1-propylpyridinium iodide 2-[[(2-Methoxybenzoyl)[[[3-chloro-4-(tetradecyloxy)phenyl]methoxy]carbonyl]amino]methyl]-1-methylpyridinium iodide 2-[[(2-Methoxybenzoyl)[[[3-chloro-4-(tetradecyloxy)phenyl]methoxy]carbonyl]amino]methyl]-1-ethylpyridinium iodide 2-[[(2-Methoxybenzoyl)[[[3-chloro-4-(tetradecyloxy)phenyl]methoxy]carbonyl]amino]methyl]-1-propylpyridinium iodide 2-[[(2-Methoxybenzoyl)[[[3,5-bis(methoxy)-4-(tetradecyloxy)phenyl]methoxy]carbonyl]amino]methyl]-1-methylpyridinium iodide 2-[[(2-Methoxybenzoyl)[[[3,5-bis(methoxy)-4-(tetradecyloxy)phenyl]methoxy]carbonyl]amino]methyl]-1-ethylpyridinium iodide 2-[[(2-Methoxybenzoyl)[[[3,5-bis(methoxy)-4-(tetradecyloxy)phenyl]methoxy]carbonyl]amino]methyl]-1-propylpyridinium iodide 2-[2-[Acetyl[[[3-(1,1-dimethylethyl)-4-(tetradecyloxy)phenyl]methoxy]carbonyl]amino]ethyl]-1-methylpyridinium iodide 2-[2-[Acetyl[[[3-(1,1-dimethylethyl)-4-(tetradecyloxy)phenyl]methoxy]carbonyl]amino]ethyl]-1-ethylpyridinium iodide 2-[2-[Acetyl[[[3-(1,1-dimethylethyl)-4-(tetradecyloxy)phenyl]methoxy]carbonyl]amino]ethyl]-1-propylpyridinium iodide 2-[2-[Acetyl[[[3-methoxy-4-(tetradecyloxy)phenyl]methoxy]carbonyl]amino]ethyl]-1-methylpyridinium iodide 2-[2-[Acetyl[[[3-methoxy-4-(tetradecyloxy)phenyl]methoxy]carbonyl]amino]ethyl]-1-ethylpyridinium iodide 2-[2-[Acetyl[[[3-methoxy-4-(tetradecyloxy)phenyl]methoxy]carbonyl]amino]ethyl]-1-propylpyridinium iodide 2-[2-[Acetyl[[[3-chloro-4-(tetradecyloxy)phenyl]methoxy]carbonyl]amino]ethyl]-1-methylpyridinium iodide 2-[2-[Acetyl[[[3-chloro-4-(tetradecyloxy)phenyl]methoxy]carbonyl]amino]ethyl]-1-ethylpyridinium iodide 2-[2-[Acetyl[[[3-chloro-4-(tetradecyloxy)phenyl]methoxy]carbonyl]amino]ethyl]-1-propylpyridinium iodide 2-[2-[Acetyl[[[3,5-bis(methoxy)-4-(tetradecyloxy)phenyl]methoxy]carbonyl]amino]ethyl]-1-methylpyridinium iodide 2-[2-[Acetyl[[[3,5-bis(methoxy)-4-(tetradecyloxy)phenyl]methoxy]carbonyl]amino]ethyl]-1-ethylpyridinium iodide 2-[2-[Acetyl[[[3,5-bis(methoxy)-4-(tetradecyloxy)phenyl]methoxy]carbonyl]amino]ethyl]-1-propylpyridinium iodide 2-[3-[Acetyl[[[3-(1,1-dimethylethyl)-4-(tetradecyloxy)phenyl]methoxy]carbonyl]amino]propyl]-1-methylpyridinium iodide 2-[3-[Acetyl[[[3-(1,1-dimethylethyl)-4-(tetradecyloxy)phenyl]methoxy]carbonyl]amino]propyl]-1-ethylpyridinium iodide 2-[3-[Acetyl[[[3-(1,1-dimethylethyl)-4-(tetradecyloxy)phenyl]methoxy]carbonyl]amino]propyl]-1-propylpyridinium iodide 2-[3-[Acetyl[[[3-methoxy-4-(tetradecyloxy)phenyl]methoxy]carbonyl]amino]propyl]-1-methylpyridinium iodide 2-[3-[Acetyl[[[3-methoxy-4-(tetradecyloxy)phenyl]methoxy]carbonyl]amino]propyl]-1-ethylpyridinium iodide 2-[3-[Acetyl[[[3-methoxy-4-(tetradecyloxy)phenyl]methoxy]carbonyl]amino]propyl]-1-propylpyridinium iodide 2-[3-[Acetyl[[[3-chloro-4-(tetradecyloxy)phenyl]methoxy]carbonyl]amino]propyl]-1-methylpyridinium iodide 2-[3-[Acetyl[[[3-chloro-4-(tetradecyloxy)phenyl]methoxy]carbonyl]amino]propyl]-1-ethylpyridinium iodide 2-[3-[Acetyl[[[3-chloro-4-(tetradecyloxy)phenyl]methoxy]carbonyl]amino]propyl]-1-propylpyridinium iodide 2-[3-[Acetyl[[[3,5-bis(methoxy)-4-(tetradecyloxy)phenyl]methoxy]carbonyl]amino]propyl]-1-methylpyridinium iodide 2-[3-[Acetyl[[[3,5-bis(methoxy)-4-(tetradecyloxy)phenyl]methoxy]carbonyl]amino]propyl]-1-ethylpyridinium iodide 2-[3-[Acetyl[[[3,5-bis(methoxy)-4-(tetradecyloxy)phenyl]methoxy]carbonyl]amino]propyl]-1-propylpyridinium iodide 3-[[Acetyl[[[3-(1,1-dimethylethyl)-4-(tetradecyloxy)phenyl]methoxy]carbonyl]amino]methyl]-1-methylpyridinium iodide 3-[[Acetyl[[[3-(1,1-dimethylethyl)-4-(tetradecyloxy)phenyl]methoxy]carbonyl]amino]methyl]-1-ethylpyridinium iodide 3-[[Acetyl[[[3-(1,1-dimethylethyl)-4-(tetradecyloxy)phenyl]methoxy]carbonyl]amino]methyl]-1-propylpyridinium iodide 3-[[Acetyl[[[3-methoxy-4-(tetradecyloxy)phenyl]methoxy]carbonyl]amino]methyl]-1-methylpyridinium iodide 3-[[Acetyl[[[3-methoxy-4-(tetradecyloxy)phenyl]methoxy]carbonyl]amino]methyl]-1-ethylpyridinium iodide 3-[[Acetyl[[[3-methoxy-4-(tetradecyloxy)phenyl]methoxy]carbonyl]amino]methyl]-1-propylpyridinium iodide 3-[[Acetyl[[[3-chloro-4-(tetradecyloxy)phenyl]methoxy]carbonyl]amino]methyl]-1-methylpyridinium iodide 3-[[Acetyl[[[3-chloro-4-(tetradecyloxy)phenyl]methoxy]carbonyl]amino]methyl]-1-ethylpyridinium iodide 3-[[Acetyl[[[3-chloro-4-(tetradecyloxy)phenyl]methoxy]carbonyl]amino]methyl]-1-propylpyridinium iodide 3-[[Acetyl[[[3,5-bis(methoxy)-4-(tetradecyloxy)phenyl]methoxy]carbonyl]amino]methyl]-1-methylpyridinium iodide 3-[[Acetyl[[[3,5-bis(methoxy)-4-(tetradecyloxy)phenyl]methoxy]carbonyl]amino]methyl]-1-ethylpyridinium iodide 3-[[Acetyl[[[3,5-bis(methoxy)-4-(tetradecyloxy)phenyl]methoxy]carbonyl]amino]methyl]-1-propylpyridinium iodide 3-[[Benzoyl[[[3-(1,1-dimethylethyl)-4-(tetradecyloxy)phenyl]methoxy]carbonyl]amino]methyl]-1-methylpyridinium iodide 3-[[Benzoyl[[[3-(1,1-dimethylethyl)-4-(tetradecyloxy)phenyl]methoxy]carbonyl]amino]methyl]-1-ethylpyridinium iodide 3-[[Benzoyl[[[3-(1,1-dimethylethyl)-4-(tetradecyloxy)phenyl]methoxy]carbonyl]amino]methyl]-1-propylpyridinium iodide 3-[[Benzoyl[[[3-methoxy-4-(tetradecyloxy)phenyl]methoxy]carbonyl]amino]methyl]-1-methylpyridinium iodide 3-[[Benzoyl[[[3-methoxy-4-(tetradecyloxy)phenyl]methoxy]carbonyl]amino]methyl]-1-ethylpyridinium iodide 3-[[Benzoyl[[[3-methoxy-4-(tetradecyloxy)phenyl]methoxy]carbonyl]amino]methyl]-1-propylpyridinium iodide 3-[[Benzoyl[[[3-chloro-4-(tetradecyloxy)phenyl]methoxy]carbonyl]amino]methyl]-1-methylpyridinium iodide 3-[[Benzoyl[[[3-chloro-4-(tetradecyloxy)phenyl]methoxy]carbonyl]amino]methyl]-1-ethylpyridinium iodide 3-[[Benzoyl[[[3-chloro-4-(tetradecyloxy)phenyl]methoxy]carbonyl]amino]methyl]-1-propylpyridinium iodide 3-[[Benzoyl[[[3,5-bis(methoxy)-4-(tetradecyloxy)phenyl]methoxy]carbonyl]amino]methyl]-1-methylpyridinium iodide 3-[[Benzoyl[[[3,5-bis(methoxy)-4-(tetradecyloxy)phenyl]methoxy]carbonyl]amino]methyl]-1-ethylpyridinium iodide 3-[[Benzoyl[[[3,5-bis(methoxy)-4-(tetradecyloxy)phenyl]methoxy]carbonyl]amino]methyl]-1-propylpyridinium iodide 3-[[(2-Methoxybenzoyl)[[[3-(1,1-dimethylethyl)-4-(tetradecyloxy)phenyl]methoxy]carbonyl]amino]methyl]-1-methylpyridinium iodide 3-[[(2-Methoxybenzoyl)[[[3-(1,1-dimethylethyl)-4-(tetradecyloxy)phenyl]methoxy]carbonyl]amino]methyl]-1-ethylpyridinium iodide 3-[[(2-Methoxybenzoyl)[[[3-(1,1-dimethylethyl)-4-(tetradecyloxy)phenyl]methoxy]carbonyl]amino]methyl]-1-propylpyridinium iodide 3-[[(2-Methoxybenzoyl)[[[3-methoxy-4-(tetradecyloxy)phenyl]methoxy]carbonyl]amino]methyl]-1-methylpyridinium iodide 3-[[(2-Methoxybenzoyl)[[[3-methoxy-4-(tetradecyloxy)phenyl]methoxy]carbonyl]amino]methyl]-1-ethylpyridinium iodide 3-[[(2-Methoxybenzoyl)[[[3-methoxy-4-(tetradecyloxy)phenyl]methoxy]carbonyl]amino]methyl]-1-propylpyridinium iodide 3-[[(2-Methoxybenzoyl)[[[3-chloro-4-(tetradecyloxy)phenyl]methoxy]carbonyl]amino]methyl]-1-methylpyridinium iodide 3-[[(2-Methoxybenzoyl)[[[3-chloro-4-(tetradecyloxy)phenyl]methoxy]carbonyl]amino]methyl]-1-ethylpyridinium iodide 3-[[(2-Methoxybenzoyl)[[[3-chloro-4-(tetradecyloxy)phenyl]methoxy]carbonyl]amino]methyl]-1-propylpyridinium iodide 3-[[(2-Methoxybenzoyl)[[[3,5-bis(methoxy)-4-(tetradecyloxy)phenyl]methoxy]carbonyl]amino]methyl]-1-methylpyridinium iodide 3-[[(2-Methoxybenzoyl)[[[3,5-bis(methoxy)-4-(tetradecyloxy)phenyl]methoxy]carbonyl]amino]methyl]-1-ethylpyridinium iodide 3-[[(2-Methoxybenzoyl)[[[3,5-bis(methoxy)-4-(tetradecyloxy)phenyl]methoxy]carbonyl]amino]methyl]-1-propylpyridinium iodide 3-[2-[Acetyl[[[3-(1,1-dimethylethyl)-4-(tetradecyloxy)phenyl]methoxy]carbonyl]amino]ethyl]-1-methylpyridinium iodide 3-[2-[Acetyl[[[3-(1,1-dimethylethyl)-4-(tetradecyloxy)phenyl]methoxy]carbonyl]amino]ethyl]-1-ethylpyridinium iodide 3-[2-[Acetyl[[[3-(1,1-dimethylethyl)-4-(tetradecyloxy)phenyl]methoxy]carbonyl]amino]ethyl]-1-propylpyridinium iodide 3-[2-[Acetyl[[[3-methoxy-4-(tetradecyloxy)phenyl]methoxy]carbonyl]amino]ethyl]-1-methylpyridinium iodide 3-[2-[Acetyl[[[3-methoxy-4-(tetradecyloxy)phenyl]methoxy]carbonyl]amino]ethyl]-1-ethylpyridinium iodide 3-[2-[Acetyl[[[3-methoxy-4-(tetradecyloxy)phenyl]methoxy]carbonyl]amino]ethyl]-1-propylpyridinium iodide 3-[2-[Acetyl[[[3-chloro-4-(tetradecyloxy)phenyl]methoxy]carbonyl]amino]ethyl]-1-methylpyridinium iodide 3-[2-[Acetyl[[[3-chloro-4-(tetradecyloxy)phenyl]methoxy]carbonyl]amino]ethyl]-1-ethylpyridinium iodide 3-[2-[Acetyl[[[3-chloro-4-(tetradecyloxy)phenyl]methoxy]carbonyl]amino]ethyl]-1-propylpyridinium iodide 3-[2-[Acetyl[[[3,5-bis(methoxy)-4-(tetradecyloxy)phenyl]methoxy]carbonyl]amino]ethyl]-1-methylpyridinium iodide 3-[2-[Acetyl[[[3,5-bis(methoxy)-4-(tetradecyloxy)phenyl]methoxy]carbonyl]amino]ethyl]-1-ethylpyridinium iodide 3-[2-[Acetyl[[[3,5-bis(methoxy)-4-(tetradecyloxy)phenyl]methoxy]carbonyl]amino]ethyl]-1-propylpyridinium iodide 3-[3-[Acetyl[[[3-(1,1-dimethylethyl)-4-(tetradecyloxy)phenyl]methoxy]carbonyl]amino]propyl]-1-methylpyridinium iodide 3-[3-[Acetyl[[[3-(1,1-dimethylethyl)-4-(tetradecyloxy)phenyl]methoxy]carbonyl]amino]propyl]-1-ethylpyridinium iodide 3-[3-[Acetyl[[[3-(1,1-dimethylethyl)-4-(tetradecyloxy)phenyl]methoxy]carbonyl]amino]propyl]-1-propylpyridinium iodide 3-[3-[Acetyl[[[3-methoxy-4-(tetradecyloxy)phenyl]methoxy]carbonyl]amino]propyl]-1-methylpyridinium iodide 3-[3-[Acetyl[[[3-methoxy-4-(tetradecyloxy)phenyl]methoxy]carbonyl]amino]propyl]-1-ethylpyridinium iodide 3-[3-[Acetyl[[[3-methoxy-4-(tetradecyloxy)phenyl]methoxy]carbonyl]amino]propyl]-1-propylpyridinium iodide 3-[3-[Acetyl[[[3-chloro-4-(tetradecyloxy)phenyl]methoxy]carbonyl]amino]propyl]-1-methylpyridinium iodide 3-[3-[Acetyl[[[3-chloro-4-(tetradecyloxy)phenyl]methoxy]carbonyl]amino]propyl]-1-ethylpyridinium iodide 3-[3-[Acetyl[[[3-chloro-4-(tetradecyloxy)phenyl]methoxy]carbonyl]amino]propyl]-1-propylpyridinium iodide 3-[3-[Acetyl[[[3,5-bis(methoxy)-4-(tetradecyloxy)phenyl]methoxy]carbonyl]amino]propyl]-1-methylpyridinium iodide 3-[3-[Acetyl[[[3,5-bis(methoxy)-4-(tetradecyloxy)phenyl]methoxy]carbonyl]amino]propyl]-1-ethylpyridinium iodide 3-[3-[Acetyl[[[3,5-bis(methoxy)-4-(tetradecyloxy)phenyl]methoxy]carbonyl]amino]propyl]-1-propylpyridinium iodide 4-[[Acetyl[[[3-(1,1-dimethylethyl)-4-(tetradecyloxy)phenyl]methoxy]carbonyl]amino]methyl]-1-methylpyridinium iodide 4-[[Acetyl[[[3-(1,1-dimethylethyl)-4-(tetradecyloxy)phenyl]methoxy]carbonyl]amino]methyl]-1-ethylpyridinium iodide 4-[[Acetyl[[[3-(1,1-dimethylethyl)-4-(tetradecyloxy)phenyl]methoxy]carbonyl]amino]methyl]-1-propylpyridinium iodide 4-[[Acetyl[[[3-methoxy-4-(tetradecyloxy)phenyl]methoxy]carbonyl]amino]methyl]-1-methylpyridinium iodide 4-[[Acetyl[[[3-methoxy-4-(tetradecyloxy)phenyl]methoxy]carbonyl]amino]methyl]-1-ethylpyridinium iodide 4-[[Acetyl[[[3-methoxy-4-(tetradecyloxy)phenyl]methoxy]carbonyl]amino]methyl]-1-propylpyridinium iodide 4-[[Acetyl[[[3-chloro-4-(tetradecyloxy)phenyl]methoxy]carbonyl]amino]methyl]-1-methylpyridinium iodide 4-[[Acetyl[[[3-chloro-4-(tetradecyloxy)phenyl]methoxy]carbonyl]amino]methyl]-1-ethylpyridinium iodide 4-[[Acetyl[[[3-chloro-4-(tetradecyloxy)phenyl]methoxy]carbonyl]amino]methyl]-1-propylpyridinium iodide 4-[[Acetyl[[[3,5-bis(methoxy)-4-(tetradecyloxy)phenyl]methoxy]carbonyl]amino]methyl]-1-methylpyridinium iodide 4-[[Acetyl[[[3,5-bis(methoxy)-4-(tetradecyloxy)phenyl]methoxy]carbonyl]amino]methyl]-1-ethylpyridinium iodide 4-[[Acetyl[[[3,5-bis(methoxy)-4-(tetradecyloxy)phenyl]methoxy]carbonyl]amino]methyl]-1-propylpyridinium iodide 4-[[Benzoyl[[[3-(1,1-dimethylethyl)-4-(tetradecyloxy)phenyl]methoxy]carbonyl]amino]methyl]-1-methylpyridinium iodide 4-[[Benzoyl[[[3-(1,1-dimethylethyl)-4-(tetradecyloxy)phenyl]methoxy]carbonyl]amino]methyl]-1-ethylpyridinium iodide 4-[[Benzoyl[[[3-(1,1-dimethylethyl)-4-(tetradecyloxy)phenyl]methoxy]carbonyl]amino]methyl]-1-propylpyridinium iodide 4-[[Benzoyl[[[3-methoxy-4-(tetradecyloxy)phenyl]methoxy]carbonyl]amino]methyl]-1-methylpyridinium iodide 4-[[Benzoyl[[[3-methoxy-4-(tetradecyloxy)phenyl]methoxy]carbonyl]amino]methyl]-1-ethylpyridinium iodide 4-[[Benzoyl[[[3-methoxy-4-(tetradecyloxy)phenyl]methoxy]carbonyl]amino]methyl]-1-propylpyridinium iodide 4-[[Benzoyl[[[3-chloro-4-(tetradecyloxy)phenyl]methoxy]carbonyl]amino]methyl]-1-methylpyridinium iodide 4-[[Benzoyl[[[3-chloro-4-(tetradecyloxy)phenyl]methoxy]carbonyl]amino]methyl]-1-ethylpyridinium iodide 4-[[Benzoyl[[[3-chloro-4-(tetradecyloxy)phenyl]methoxy]carbonyl]amino]methyl]-1-propylpyridinium iodide 4-[[Benzoyl[[[3,5-bis(methoxy)-4-(tetradecyloxy)phenyl]methoxy]carbonyl]amino]methyl]-1-methylpyridinium iodide 4-[[Benzoyl[[[3,5-bis(methoxy)-4-(tetradecyloxy)phenyl]methoxy]carbonyl]amino]methyl]-1-ethylpyridinium iodide 4-[[Benzoyl[[[3,5-bis(methoxy)-4-(tetradecyloxy)phenyl]methoxy]carbonyl]amino]methyl]-1-propylpyridinium iodide 4-[[(2-Methoxybenzoyl)[[[3-(1,1-dimethylethyl)-4-(tetradecyloxy)phenyl]methoxy]carbonyl]amino]methyl]-1-methylpyridinium iodide 4-[[(2-Methoxybenzoyl)[[[3-(1,1-dimethylethyl)-4-(tetradecyloxy)phenyl]methoxy]carbonyl]amino]methyl]-1-ethylpyridinium iodide 4-[[(2-Methoxybenzoyl)[[[3-(1,1-dimethylethyl)-4-(tetradecyloxy)phenyl]methoxy]carbonyl]amino]methyl]-1-propylpyridinium iodide 4-[[(2-Methoxybenzoyl)[[[3-methoxy-4-(tetradecyloxy)phenyl]methoxy]carbonyl]amino]methyl]-1-methylpyridinium iodide 4-[[(2-Methoxybenzoyl)[[[3-methoxy-4-(tetradecyloxy)phenyl]methoxy]carbonyl]amino]methyl]-1-ethylpyridinium iodide 4-[[(2-Methoxybenzoyl)[[[3-methoxy-4-(tetradecyloxy)phenyl]methoxy]carbonyl]amino]methyl]-1-propylpyridinium iodide 4-[[(2-Methoxybenzoyl)[[[3-chloro-4-(tetradecyloxy)phenyl]methoxy]carbonyl]amino]methyl]-1-methylpyridinium iodide 4-[[(2-Methoxybenzoyl)[[[3-chloro-4-(tetradecyloxy)phenyl]methoxy]carbonyl]amino]methyl]-1-ethylpyridinium iodide 4-[[(2-Methoxybenzoyl)[[[3-chloro-4-(tetradecyloxy)phenyl]methoxy]carbonyl]amino]methyl]-1-propylpyridinium iodide 4-[[(2-Methoxybenzoyl)[[[3,5-bis(methoxy)-4-(tetradecyloxy)phenyl]methoxy]carbonyl]amino]methyl]-1-methylpyridinium iodide 4-[[(2-Methoxybenzoyl)[[[3,5-bis(methoxy)-4-(tetradecyloxy)phenyl]methoxy]carbonyl]amino]methyl]-1-ethylpyridinium iodide 4-[[(2-Methoxybenzoyl)[[[3,5-bis(methoxy)-4-(tetradecyloxy)phenyl]methoxy]carbonyl]amino]methyl]-1-propylpyridinium iodide 4-[2-[Acetyl[[[3-(1,1-dimethylethyl)-4-(tetradecyloxy)phenyl]methoxy]carbonyl]amino]ethyl]-1-methylpyridinium iodide 4-[2-[Acetyl[[[3-(1,1-dimethylethyl)-4-(tetradecyloxy)phenyl]methoxy]carbonyl]amino]ethyl]-1-ethylpyridinium iodide 4-[2-[Acetyl[[[3-(1,1-dimethylethyl)-4-(tetradecyloxy)phenyl]methoxy]carbonyl]amino]ethyl]-1-propylpyridinium iodide 4-[2-[Acetyl[[[3-methoxy-4-(tetradecyloxy)phenyl]methoxy]carbonyl]amino]ethyl]-1-methylpyridinium iodide 4-[2-[Acetyl[[[3-methoxy-4-(tetradecyloxy)phenyl]methoxy]carbonyl]amino]ethyl]-1-ethylpyridinium iodide 4-[2-[Acetyl[[[3-methoxy-4-(tetradecyloxy)phenyl]methoxy]carbonyl]amino]ethyl]-1-propylpyridinium iodide 4-[2-[Acetyl[[[3-chloro-4-(tetradecyloxy)phenyl]methoxy]carbonyl]amino]ethyl]-1-methylpyridinium iodide 4-[2-[Acetyl[[[3-chloro-4-(tetradecyloxy)phenyl]methoxy]carbonyl]amino]ethyl]-1-ethylpyridinium iodide 4-[2-[Acetyl[[[3-chloro-4-(tetradecyloxy)phenyl]methoxy]carbonyl]amino]ethyl]-1-propylpyridinium iodide 4-[2-[Acetyl[[[3,5-bis(methoxy)-4-(tetradecyloxy)phenyl]methoxy]carbonyl]amino]ethyl]-1-methylpyridinium iodide 4-[2-[Acetyl[[[3,5-bis(methoxy)-4-(tetradecyloxy)phenyl]methoxy]carbonyl]amino]ethyl]-1-ethylpyridinium iodide 4-[2-[Acetyl[[[3,5-bis(methoxy)-4-(tetradecyloxy)phenyl]methoxy]carbonyl]amino]ethyl]-1-propylpyridinium iodide 4-[3-[Acetyl[[[3-(1,1-dimethylethyl)-4-(tetradecyloxy)phenyl]methoxy]carbonyl]amino]propyl]-1-methylpyridinium iodide 4-[3-[Acetyl[[[3-(1,1-dimethylethyl)-4-(tetradecyloxy)phenyl]methoxy]carbonyl]amino]propyl]-1-ethylpyridinium iodide 4-[3-[Acetyl[[[3-(1,1-dimethylethyl)-4-(tetradecyloxy)phenyl]methoxy]carbonyl]amino]propyl]-1-propylpyridinium iodide 4-[3-[Acetyl[[[3-methoxy-4-(tetradecyloxy)phenyl]methoxy]carbonyl]amino]propyl]-1-methylpyridinium iodide 4-[3-[Acetyl[[[3-methoxy-4-(tetradecyloxy)phenyl]methoxy]carbonyl]amino]propyl]-1-ethylpyridinium iodide 4-[3-[Acetyl[[[3-methoxy-4-(tetradecyloxy)phenyl]methoxy]carbonyl]amino]propyl]-1-propylpyridinium iodide 4-[3-[Acetyl[[[3-chloro-4-(tetradecyloxy)phenyl]methoxy]carbonyl]amino]propyl]-1-methylpyridinium iodide 4-[3-[Acetyl[[[3-chloro-4-(tetradecyloxy)phenyl]methoxy]carbonyl]amino]propyl]-1-ethylpyridinium iodide 4-[3-[Acetyl[[[3-chloro-4-(tetradecyloxy)phenyl]methoxy]carbonyl]amino]propyl]-1-propylpyridinium iodide 4-[3-[Acetyl[[[3,5-bis(methoxy)-4-(tetradecyloxy)phenyl]methoxy]carbonyl]amino]propyl]-1-ethylpyridinium iodide 4-[3-[Acetyl[[[3,5-bis(methoxy)-4-(tetradecyloxy)phenyl]methoxy]carbonyl]amino]propyl]-1-propylpyridinium iodide According to the methods outlined hereinabove in Flowsheets F, H, I, and M, and described in detail in Examples 1, 2, 12-15, 17, 18, 23, 31, 32, 36, 37, 40-42, 46, 47, 51, 52, 60-64, 66, 67, 81, 82, 98, 99, 102-104, 109, 110, 114-119, 130, 131, and 144-148, the compounds of this invention listed hereinbelow in List 4 can be prepared. These methods are applicable to the preparation of the compounds of this invention by one skilled in the art.

List 4

1-Methyl-2-[[[[3-(1,1-dimethylethyl)-4-(tetradecyloxy)phenyl]methyl]amino]carbonyl]pyridinium iodide 1-Methyl-2-[[[[3-(1,1-dimethylethyl)-4-(dodecyloxy)phenyl]methyl]amino]carbonyl]pyridinium iodide 1-Methyl-2-[[[[3-methoxy-4-(hexadecyloxy)phenyl]methyl]amino]carbonyl]pyridinium iodide 1-Methyl-2-[[[[2-methyl-4-(tetradecyloxy)phenyl]methyl]amino]carbonyl]pyridinium iodide 1-Methyl-2-[[[[2-methyl-4-(dodecyloxy)phenyl]methyl]amino]carbonyl]pyridinium iodide 1-Methyl-2-[[[[3-chloro-4-(tetradecyloxy)phenyl]methyl]amino]carbonyl]pyridinium iodide 1-Methyl-2-[[[[3-chloro-4-(dodecyloxy)phenyl]methyl]amino]carbonyl]pyridinium iodide 1-Methyl-3-[[[[3-(1,1-dimethylethyl)-4-(hexadecyloxy)phenyl]methyl]amino]carbonyl]pyridinium iodide 1-Methyl-3-[[[[3-methoxy-4-(tetradecyloxy)phenyl]methyl]amino]carbonyl]pyridinium iodide 1-Methyl-3-[[[[3-methoxy-4-(dodecyloxy)phenyl]methyl]amino]carbonyl]pyridinium iodide 1-Methyl-3-[[[[2-methyl-4-(hexadecyloxy)phenyl]methyl]amino]carbonyl]pyridinium iodide 1-Methyl-3-[[[[2-methyl-3-(tetradecyloxy)phenyl]methyl]amino]carbonyl]pyridinium iodide 1-Methyl-3-[[[[3-chloro-4-(hexadecyloxy)phenyl]methyl]amino]carbonyl]pyridinium iodide 1-Methyl-4-[[[[3-(1,1-dimethylethyl)-4-(tetradecyloxy)phenyl]methyl]amino]carbonyl]pyridinium iodide 1-Methyl-4-[[[[3-(1,1-dimethylethyl)-4-(dodecyloxy)phenyl]methyl]amino]carbonyl]pyridinium iodide 1-Methyl-4-[[[[3-methoxy-4-(hexadecyloxy)phenyl]methyl]amino]carbonyl]pyridinium iodide 1-Methyl-4-[[[[2-methyl-4-(tetradecyloxy)phenyl]methyl]amino]carbonyl]pyridinium iodide 1-Methyl-4-[[[[2-methyl-4-(dodecyloxy)phenyl]methyl]amino]carbonyl]pyridinium iodide 1-Methyl-4-[[[[3-chloro-4-(tetradecyloxy)phenyl]methyl]amino]carbonyl]pyridinium iodide 1-Methyl-4-[[[[3-chloro-4-(dodecyloxy)phenyl]methyl]amino]carbonyl]pyridinium iodide 1-Methyl-3-[[phenyl[[3-(1,1-dimethylethyl)-4-(hexadecyloxy)phenyl]methyl]amino]carbonyl]pyridinium iodide 1-Methyl-3-[[phenyl[[3-methoxy-4-(tetradecyloxy)phenyl]methyl]amino]carbonyl]pyridinium iodide 1-Methyl-3-[[phenyl[[3-methoxy-4-(dodecyloxy)phenyl]methyl]amino]carbonyl]pyridinium iodide 1-Methyl-3-[[phenyl[[2-methyl-4-(tetradecyloxy)phenyl]methyl]amino]carbonyl]pyridinium iodide 1-Methyl-3-[[phenyl[[2-methyl-4-(dodecyloxy)phenyl]methyl]amino]carbonyl]pyridinium iodide 1-Methyl-3-[[phenyl[[3-chloro-4-(tetradecyloxy)phenyl]methyl]amino]carbonyl]pyridinium iodide 1-Methyl-3-[[phenyl[[3-chloro-4-(dodecyloxy)phenyl]methyl]amino]carbonyl]pyridinium iodide 1-Methyl-4-[[phenyl[[3-(1,1-dimethylethyl)-4-(hexadecyloxy)phenyl]methyl]amino]carbonyl]pyridinium iodide 1-Methyl-4-[[phenyl[[3-methoxy-4-(tetradecyloxy)phenyl]methyl]amino]carbonyl]pyridinium iodide 1-Methyl-4-[[phenyl[[3-methoxy-4-(dodecyloxy)phenyl]methyl]amino]carbonyl]pyridinium iodide 1-Methyl-4-[[phenyl[[2-methyl-4-(hexadecyloxy)phenyl]methyl]amino]carbonyl]pyridinium iodide 1-Methyl-4-[[phenyl[[2-methyl-3-(tetradecyloxy)phenyl]methyl]amino]carbonyl]pyridinium iodide 1-Methyl-4-[[phenyl[[3-chloro-4-(hexadecyloxy)phenyl]methyl]amino]carbonyl]pyridinium iodide 1-Methyl-2-[[phenyl[[3-(1,1-dimethylethyl)-4-(tetradecyloxy)phenyl]methyl]amino]carbonyl]pyridinium iodide 1-Methyl-2-[[phenyl[[3-(1,1-dimethylethyl)-4-(dodecyloxy)phenyl]methyl]amino]carbonyl]pyridinium iodide 1-Methyl-2-[[phenyl[[3-methoxy-4-(hexadecyloxy)phenyl]methyl]amino]carbonyl]pyridinium iodide 1-Methyl-2-[[phenyl[[2-methyl-4-(tetradecyloxy)phenyl]methyl]amino]carbonyl]pyridinium iodide 1-Methyl-2-[[phenyl[[2-methyl-4-(dodecyloxy)phenyl]methyl]amino]carbonyl]pyridinium iodide 1-Methyl-2-[[phenyl[[3-chloro-4-(tetradecyloxy)phenyl]methyl]amino]carbonyl]pyridinium iodide 1-Methyl-2-[[phenyl[[3-chloro-4-(dodecyloxy)phenyl]methyl]amino]carbonyl]pyridinium iodide 1-Methyl-2-[2-[[[3-(1,1-dimethylethyl)-4-(hexadecyloxy)phenyl]ethyl]amino]carbonyl]pyridinium iodide 1-Methyl-2-[2-[[[3-methoxy-4-(tetradecyloxy)phenyl]ethyl]amino]carbonyl]pyridinium iodide 1-Methyl-2-[2-[[[3-methoxy-4-(dodecyloxy)phenyl]ethyl]amino]carbonyl]pyridinium iodide 1-Methyl-2-[2-[[[2-methyl-4-(hexadecyloxy)phenyl]ethyl]amino]carbonyl]pyridinium iodide 1-Methyl-2-[2-[[[2-methyl-3-(tetradecyloxy)phenyl]ethyl]amino]carbonyl]pyridinium iodide 1-Methyl-2-[2-[[[3-chloro-4-(hexadecyloxy)phenyl]ethyl]amino]carbonyl]pyridinium iodide 1-Methyl-4-[3-[[[3-(1,1-dimethylethyl)-4-(tetradecyloxy)phenyl]propyl]amino]carbonyl]pyridinium iodide 1-Methyl-4-[3-[[[3-(1,1-dimethylethyl)-4-(dodecyloxy)phenyl]propyl]amino]carbonyl]pyridinium iodide 1-Methyl-4-[3-[[[3-methoxy-4-(hexadecyloxy)phenyl]propyl]amino]carbonyl]pyridinium iodide 1-Methyl-4-[3-[[[2-methyl-4-(tetradecyloxy)phenyl]propyl]amino]carbonyl]pyridinium iodide 1-Methyl-4-[3-[[[2-methyl-4-(dodecyloxy)phenyl]propyl]amino]carbonyl]pyridinium iodide 1-Methyl-4-[3-[[[3-chloro-4-(tetradecyloxy)phenyl]propyl]amino]carbonyl]pyridinium iodide 1-Methyl-4-[3-[[[3-chloro-4-(dodecyloxy)phenyl]propyl]amino]carbonyl]pyridinium iodide 1-Ethyl-2-[[[[3-(1,1-dimethylethyl)-4-(hexadecyloxy)phenyl]methyl]amino]carbonyl]pyridinium iodide 1-Ethyl-2-[[[[3-methoxy-4-(tetradecyloxy)phenyl]methyl]amino]carbonyl]pyridinium iodide 1-Ethyl-2-[[[[3-methoxy-4-(dodecyloxy)phenyl]methyl]amino]carbonyl]pyridinium iodide 1-Ethyl-2-[[[[2-methyl-4-(hexadecyloxy)phenyl]methyl]amino]carbonyl]pyridinium iodide 1-Ethyl-2-[[[[2-methyl-3-(tetradecyloxy)phenyl]methyl]amino]carbonyl]pyridinium iodide 1-Ethyl-2-[[[[3-chloro-4-(hexadecyloxy)phenyl]methyl]amino]carbonyl]pyridinium iodide 1-Ethyl-3-[[[[3-(1,1-dimethylethyl)-4-(tetradecyloxy)phenyl]methyl]amino]carbonyl]pyridinium iodide 1-Ethyl-3-[[[[3-(1,1-dimethylethyl)-4-(dodecyloxy)phenyl]methyl]amino]carbonyl]pyridinium iodide 1-Ethyl-3-[[[[3-methoxy-4-(hexadecyloxy)phenyl]methyl]amino]carbonyl]pyridinium iodide 1-Ethyl-3-[[[[2-methyl-4-(tetradecyloxy)phenyl]methyl]amino]carbonyl]pyridinium iodide 1-Ethyl-3-[[[[2-methyl-4-(dodecyloxy)phenyl]methyl]amino]carbonyl]pyridinium iodide 1-Ethyl-3-[[[[3-chloro-4-(tetradecyloxy)phenyl]methyl]amino]carbonyl]pyridinium iodide 1-Ethyl-3-[[[[3-chloro-4-(dodecyloxy)phenyl]methyl]amino]carbonyl]pyridinium iodide 1-Ethyl-4-[[[[3-(1,1-dimethylethyl)-4-(hexadecyloxy)phenyl]methyl]amino]carbonyl]pyridinium iodide 1-Ethyl-4-[[[[3-methoxy-4-(tetradecyloxy)phenyl]methyl]amino]carbonyl]pyridinium iodide 1-Ethyl-4-[[[[3-methoxy-4-(dodecyloxy)phenyl]methyl]amino]carbonyl]pyridinium iodide 1-Ethyl-4-[[[[2-methyl-4-(hexadecyloxy)phenyl]methyl]amino]carbonyl]pyridinium iodide 1-Ethyl-4-[[[[2-methyl-3-(tetradecyloxy)phenyl]methyl]amino]carbonyl]pyridinium iodide 1-Ethyl-4-[[[[3-chloro-4-(hexadecyloxy)phenyl]methyl]amino]carbonyl]pyridinium iodide 1-Ethyl-3-[[phenyl[[3-(1,1-dimethylethyl)-4-(tetradecyloxy)phenyl]methyl]amino]carbonyl]pyridinium iodide 1-Ethyl-3-[[phenyl[[3-(1,1-dimethylethyl)-4-(dodecyloxy)phenyl]methyl]amino]carbonyl]pyridinium iodide 1-Ethyl-3-[[phenyl[[3-methoxy-4-(hexadecyloxy)phenyl]methyl]amino]carbonyl]pyridinium iodide 1-Ethyl-3-[[phenyl[[2-methyl-4-(tetradecyloxy)phenyl]methyl]amino]carbonyl]pyridinium iodide 1-Ethyl-3-[[phenyl[[2-methyl-4-(dodecyloxy)phenyl]methyl]amino]carbonyl]pyridinium iodide 1-Ethyl-3-[[phenyl[[3-chloro-4-(tetradecyloxy)phenyl]methyl]amino]carbonyl]pyridinium iodide 1-Ethyl-3-[[phenyl[[3-chloro-4-(dodecyloxy)phenyl]methyl]amino]carbonyl]pyridinium iodide 1-Ethyl-4-[[phenyl[[3-(1,1-dimethylethyl)-4-(hexadecyloxy)phenyl]methyl]amino]carbonyl]pyridinium iodide 1-Ethyl-4-[[phenyl[[3-methoxy-4-(tetradecyloxy)phenyl]methyl]amino]carbonyl]pyridinium iodide 1-Ethyl-4-[[phenyl[[3-methoxy-4-(dodecyloxy)phenyl]methyl]amino]carbonyl]pyridinium iodide 1-Ethyl-4-[[phenyl[[2-methyl-4-(hexadecyloxy)phenyl]methyl]amino]carbonyl]pyridinium iodide 1-Ethyl-4-[[phenyl[[2-methyl-3-(tetradecyloxy)phenyl]methyl]amino]carbonyl]pyridinium iodide 1-Ethyl-4-[[phenyl[[3-chloro-4-(hexadecyloxy)phenyl]methyl]amino]carbonyl]pyridinium iodide 1-Ethyl-2-[[phenyl[[3-(1,1-dimethylethyl)-4-(tetradecyloxy)phenyl]methyl]amino]carbonyl]pyridinium iodide 1-Ethyl-2-[[phenyl[[3-(1,1-dimethylethyl)-4-(dodecyloxy)phenyl]methyl]amino]carbonyl]pyridinium iodide 1-Ethyl-2-[[phenyl[[3-methoxy-4-(hexadecyloxy)phenyl]methyl]amino]carbonyl]pyridinium iodide 1-Ethyl-2-[[phenyl[[2-methyl-4-(tetradecyloxy)phenyl]methyl]amino]carbonyl]pyridinium iodide 1-Ethyl-2-[[phenyl[[2-methyl-4-(dodecyloxy)phenyl]methyl]amino]carbonyl]pyridinium iodide 1-Ethyl-2-[[phenyl[[3-chloro-4-(tetradecyloxy)phenyl]methyl]amino]carbonyl]pyridinium iodide 1-Ethyl-2-[[phenyl[[3-chloro-4-(dodecyloxy)phenyl]methyl]amino]carbonyl]pyridinium iodide 1-Ethyl-2-[2-[[[3-(1,1-dimethylethyl)-4-(hexadecyloxy)phenyl]ethyl]amino]carbonyl]pyridinium iodide 1-Ethyl-2-[2-[[[3-methoxy-4-(tetradecyloxy)phenyl]ethyl]amino]carbonyl]pyridinium iodide 1-Ethyl-2-[2-[[[3-methoxy-4-(dodecyloxy)phenyl]ethyl]amino]carbonyl]pyridinium iodide 1-Ethyl-2-[2-[[[2-methyl-4-(hexadecyloxy)phenyl]ethyl]amino]carbonyl]pyridinium iodide 1-Ethyl-2-[2-[[[2-methyl-3-(tetradecyloxy)phenyl]ethyl]amino]carbonyl]pyridinium iodide 1-Ethyl-2-[2-[[[3-chloro-4-(hexadecyloxy)phenyl]ethyl]amino]carbonyl]pyridinium iodide 1-Ethyl-4-[3-[[[3-(1,1-dimethylethyl)-4-(tetradecyloxy)phenyl]propyl]amino]carbonyl]pyridinium iodide 1-Ethyl-4-[3-[[[3-(1,1-dimethylethyl)-4-(dodecyloxy)phenyl]propyl]amino]carbonyl]pyridinium iodide 1-Ethyl-4-[3-[[[3-methoxy-4-(hexadecyloxy)phenyl]propyl]amino]carbonyl]pyridinium iodide 1-Ethyl-4-[3-[[[2-methyl-4-(tetradecyloxy)phenyl]propyl]amino]carbonyl]pyridinium iodide 1-Ethyl-4-[3-[[[2-methyl-4-(dodecyloxy)phenyl]propyl]amino]carbonyl]pyridinium iodide 1-Ethyl-4-[3-[[[3-chloro-4-(tetradecyloxy)phenyl]propyl]amino]carbonyl]pyridinium iodide 1-Ethyl-4-[3-[[[3-chloro-4-(dodecyloxy)phenyl]propyl]amino]carbonyl]pyridinium iodide 1-Propyl-2-[[[[3-(1,1-dimethylethyl)-4-(hexadecyloxy)phenyl]methyl]amino]carbonyl]pyridinium iodide 1-Propyl-2-[[[[3-methoxy-4-(tetradecyloxy)phenyl]methyl]amino]carbonyl]pyridinium iodide 1-Propyl-2-[[[[3-methoxy-4-(dodecyloxy)phenyl]methyl]amino]carbonyl]pyridinium iodide 1-Propyl-2-[[[[2-methyl-4-(hexadecyloxy)phenyl]methyl]amino]carbonyl]pyridinium iodide 1-Propyl-2-[[[[2-methyl-3-(tetradecyloxy)phenyl]methyl]amino]carbonyl]pyridinium iodide 1-Propyl-2-[[[[3-chloro-4-(hexadecyloxy)phenyl]methyl]amino]carbonyl]pyridinium iodide 1-Propyl-2-[[[[3-chloro-4-(dodecyloxy)phenyl]methyl]amino]carbonyl]pyridinium iodide 1-Propyl-3-[[[[3-(1,1-dimethylethyl)-4-(tetradecyloxy)phenyl]methyl]amino]carbonyl]pyridinium iodide 1-Propyl-3-[[[[3-(1,1-dimethylethyl)-4-(dodecyloxy)phenyl]methyl]amino]carbonyl]pyridinium iodide 1-Propyl-3-[[[[3-methoxy-4-(hexadecyloxy)phenyl]methyl]amino]carbonyl]pyridinium iodide 1-Propyl-3-[[[[2-methyl-4-(tetradecyloxy)phenyl]methyl]amino]carbonyl]pyridinium iodide 1-Propyl-3-[[[[2-methyl-4-(hexadecyloxy)phenyl]methyl]amino]carbonyl]pyridinium iodide 1-Propyl-3-[[[[2-methyl-4-(dodecyloxy)phenyl]methyl]amino]carbonyl]pyridinium iodide 1-Propyl-3-[[[[2-methyl-3-(tetradecyloxy)phenyl]methyl]amino]carbonyl]pyridinium iodide 1-Propyl-3-[[[[3-chloro-4-(tetradecyloxy)phenyl]methyl]amino]carbonyl]pyridinium iodide 1-Propyl-3-[[[[3-chloro-4-(hexadecyloxy)phenyl]methyl]amino]carbonyl]pyridinium iodide 1-Propyl-4-[[[[3-(1,1-dimethylethyl)-4-(tetradecyloxy)phenyl]methyl]amino]carbonyl]pyridinium iodide 1-Propyl-4-[[[[3-(1,1-dimethylethyl)-4-(dodecyloxy)phenyl]methyl]amino]carbonyl]pyridinium iodide 1-Propyl-4-[[[[3-methoxy-4-(tetradecyloxy)phenyl]methyl]amino]carbonyl]pyridinium iodide 1-Propyl-4-[[[[3-methoxy-4-(dodecyloxy)phenyl]methyl]amino]carbonyl]pyridinium iodide 1-Propyl-4-[[[[2-methyl-4-(tetradecyloxy)phenyl]methyl]amino]carbonyl]pyridinium iodide 1-Propyl-4-[[[[2-methyl-4-(hexadecyloxy)phenyl]methyl]amino]carbonyl]pyridinium iodide 1-Propyl-4-[[[[2-methyl-4-(dodecyloxy)phenyl]methyl]amino]carbonyl]pyridinium iodide 1-Propyl-4-[[[[2-methyl-3-(tetradecyloxy)phenyl]methyl]amino]carbonyl]pyridinium iodide 1-Propyl-4-[[[[3-chloro-4-(tetradecyloxy)phenyl]methyl]amino]carbonyl]pyridinium iodide 1-Propyl-4-[[[[3-chloro-4-(hexadecyloxy)phenyl]methyl]amino]carbonyl]pyridinium iodide 1-Propyl-4-[[[[3-chloro-4-(dodecyloxy)phenyl]methyl]amino]carbonyl]pyridinium iodide 1-Propyl-3-[[phenyl[[3-(1,1-dimethylethyl)-4-(tetradecyloxy)phenyl]methyl]amino]carbonyl]pyridinium iodide 1-Propyl-3-[[phenyl[[3-(1,1-dimethylethyl)-4-(hexadecyloxy)phenyl]methyl]amino]carbonyl]pyridinium iodide 1-Propyl-3-[[phenyl[[3-(1,1-dimethylethyl)-4-(dodecyloxy)phenyl]methyl]amino]carbonyl]pyridinium iodide 1-Propyl-3-[[phenyl[[3-methoxy-4-(tetradecyloxy)phenyl]methyl]amino]carbonyl]pyridinium iodide 1-Propyl-3-[[phenyl[[3-methoxy-4-(hexadecyloxy)phenyl]methyl]amino]carbonyl]pyridinium iodide 1-Propyl-3-[[phenyl[[3-methoxy-4-(dodecyloxy)phenyl]methyl]amino]carbonyl]pyridinium iodide 1-Propyl-3-[[phenyl[[2-methyl-4-(tetradecyloxy)phenyl]methyl]amino]carbonyl]pyridinium iodide 1-Propyl-3-[[phenyl[[2-methyl-4-(hexadecyloxy)phenyl]methyl]amino]carbonyl]pyridinium iodide 1-Propyl-3-[[phenyl[[2-methyl-4-(dodecyloxy)phenyl]methyl]amino]carbonyl]pyridinium iodide 1-Propyl-3-[[phenyl[[2-methyl-3-(tetradecyloxy)phenyl]methyl]amino]carbonyl]pyridinium iodide 1-Propyl-3-[[phenyl[[3-chloro-4-(tetradecyloxy)phenyl]methyl]amino]carbonyl]pyridinium iodide 1-Propyl-3-[[phenyl[[3-chloro-4-(hexadecyloxy)phenyl]methyl]amino]carbonyl]pyridinium iodide 1-Propyl-3-[[phenyl[[3-chloro-4-(dodecyloxy)phenyl]methyl]amino]carbonyl]pyridinium iodide 1-Propyl-4-[[phenyl[[3-(1,1-dimethylethyl)-4-(tetradecyloxy)phenyl]methyl]amino]carbonyl]pyridinium iodide 1-Propyl-4-[[phenyl[[3-(1,1-dimethylethyl)-4-(hexadecyloxy)phenyl]methyl]amino]carbonyl]pyridinium iodide 1-Propyl-4-[[phenyl[[3-(1,1-dimethylethyl)-4-(dodecyloxy)phenyl]methyl]amino]carbonyl]pyridinium iodide 1-Propyl-4-[[phenyl[[3-methoxy-4-(tetradecyloxy)phenyl]methyl]amino]carbonyl]pyridinium iodide 1-Propyl-4-[[phenyl[[3-methoxy-4-(hexadecyloxy)phenyl]methyl]amino]carbonyl]pyridinium iodide 1-Propyl-4-[[phenyl[[3-methoxy-4-(dodecyloxy)phenyl]methyl]amino]carbonyl]pyridinium iodide 1-Propyl-4-[[phenyl[[2-methyl-4-(tetradecyloxy)phenyl]methyl]amino]carbonyl]pyridinium iodide 1-Propyl-4-[[phenyl[[2-methyl-4-(hexadecyloxy)phenyl]methyl]amino]carbonyl]pyridinium iodide 1-Propyl-4-[[phenyl[[2-methyl-4-(dodecyloxy)phenyl]methyl]amino]carbonyl]pyridinium iodide 1-Propyl-4-[[phenyl[[2-methyl-3-(tetradecyloxy)phenyl]methyl]amino]carbonyl]pyridinium iodide 1-Propyl-4-[[phenyl[[3-chloro-4-(tetradecyloxy)phenyl]methyl]amino]carbonyl]pyridinium iodide
1-Propyl-4-[[phenyl[[3-chloro-4-(hexadecyloxy)phenyl]methyl]amino]carbonyl]pyridinium iodide 1-Propyl-4-[[phenyl[[3-chloro-4-(dodecyloxy)phenyl]methyl]amino]carbonyl]pyridinium iodide 1-Propyl-2-[[phenyl[[3-(1,1-dimethylethyl)-4-(tetradecyloxy)phenyl]methyl]amino]carbonyl]pyridinium iodide 1-Propyl-2-[[phenyl[[3-(1,1-dimethylethyl)-4-(hexadecyloxy)phenyl]methyl]amino]carbonyl]pyridinium iodide 1-Propyl-2-[[phenyl[[3-(1,1-dimethylethyl)-4-(dodecyloxy)phenyl]methyl]amino]carbonyl]pyridinium iodide 1-Propyl-2-[[phenyl[[3-methoxy-4-(tetradecyloxy)phenyl]methyl]amino]carbonyl]pyridinium iodide 1-Propyl-2-[[phenyl[[3-methoxy-4-(hexadecyloxy)phenyl]methyl]amino]carbonyl]pyridinium iodide 1-Propyl-2-[[phenyl[[3-methoxy-4-(dodecyloxy)phenyl]methyl]amino]carbonyl]pyridinium iodide 1-Propyl-2-[[phenyl[[2-methyl-4-(hexadecyloxy)phenyl]methyl]amino]carbonyl]pyridinium iodide 1-Propyl-2-[[phenyl[[2-methyl-3-(tetradecyloxy)phenyl]methyl]amino]carbonyl]pyridinium iodide 1-Propyl-2-[[phenyl[[3-chloro-4-(hexadecyloxy)phenyl]methyl]amino]carbonyl]pyridinium iodide 1-Propyl-2-[[phenyl[[3-chloro-4-(dodecyloxy)phenyl]methyl]amino]carbonyl]pyridinium iodide 1-Propyl-2-[2-[[[3-(1,1-dimethylethyl)-4-(tetradecyloxy)phenyl]ethyl]amino]carbonyl]pyridinium iodide 1-Propyl-2-[2-[[[3-(1,1-dimethylethyl)-4-(hexadecyloxy)phenyl]ethyl]amino]carbonyl]pyridinium iodide 1-Propyl-2-[2-[[[3-(1,1-dimethylethyl)-4-(dodecyloxy)phenyl]ethyl]amino]carbonyl]pyridinium iodide 1-Propyl-2-[2-[[[3-methoxy-4-(hexadecyloxy)phenyl]ethyl]amino]carbonyl]pyridinium iodide 1-Propyl-2-[2-[[[2-methyl-4-(tetradecyloxy)phenyl]ethyl]amino]carbonyl]pyridinium iodide 1-Propyl-2-[2-[[[2-methyl-4-(hexadecyloxy)phenyl]ethyl]amino]carbonyl]pyridinium iodide 1-Propyl-2-[2-[[[2-methyl-4-(dodecyloxy)phenyl]ethyl]amino]carbonyl]pyridinium iodide 1-Propyl-2-[2-[[[2-methyl-3-(tetradecyloxy)phenyl]ethyl]amino]carbonyl]pyridinium iodide 1-Propyl-2-[2-[[[3-chloro-4-(tetradecyloxy)phenyl]ethyl]amino]carbonyl]pyridinium iodide 1-Propyl-2-[2-[[[3-chloro-4-(hexadecyloxy)phenyl]ethyl]amino]carbonyl]pyridinium iodide 1-Propyl-2-[2-[[[3-chloro-4-(dodecyloxy)phenyl]ethyl]amino]carbonyl]pyridinium iodide 1-Propyl-4-[3-[[[3-(1,1-dimethylethyl)-4-(tetradecyloxy)phenyl]propyl]amino]carbonyl]pyridinium iodide 1-Propyl-4-[3-[[[3-(1,1-dimethylethyl)-4-(hexadecyloxy)phenyl]propyl]amino]carbonyl]pyridinium iodide 1-Propyl-4-[3-[[[3-(1,1-dimethylethyl)-4-(dodecyloxy)phenyl]propyl]amino]carbonyl]pyridinium iodide 1-Propyl-4-[3-[[[3-methoxy-4-(tetradecyloxy)phenyl]propyl]amino]carbonyl]pyridinium iodide 1-Propyl-4-[3-[[[3-methoxy-4-(hexadecyloxy)phenyl]propyl]amino]carbonyl]pyridinium iodide 1-Propyl-4-[3-[[[2-methyl-4-(tetradecyloxy)phenyl]propyl]amino]carbonyl]pyridinium iodide 1-Propyl-4-[3-[[[2-methyl-4-(hexadecyloxy)phenyl]propyl]amino]carbonyl]pyridinium iodide 1-Propyl-4-[3-[[[2-methyl-3-(tetradecyloxy)phenyl]propyl]amino]carbonyl]pyridinium iodide 1-Propyl-4-[3-[[[3-chloro-4-(hexadecyloxy)phenyl]propyl]amino]carbonyl]pyridinium iodide 1-Propyl-4-[3-[[[3-chloro-4-(dodecyloxy)phenyl]propyl]amino]carbonyl]pyridinium iodide According to the methods outlined hereinabove in Flowsheets F, H, and L, and described in detail in Examples 1, 2, 17-25, 31, 32, 36, 37, 40-42, 46, 47, 51, 52, 60-64, 66, 67, 69-83, 98, 99, 102-104, 109, 110, 121-123, 130, 131, and 141-143, the compounds of this invention listed hereinbelow in List 5 can be prepared. These methods are applicable to the preparation of the compounds of this invention by one skilled in the art.

2-[[Acetyl[[3-(1,1-dimethylethyl)-2-(tetradecyloxy)phenyl]methyl]amino]methyl]-1-methylpyridinium iodide 2-[[Acetyl[[3-(1,1-dimethylethyl)-4-(tetradecyloxy)phenyl]methyl]amino]methyl]-1-ethylpyridinium iodide 2-[[Acetyl[[3-(1,1-dimethylethyl)-4-(dodecyloxy)phenyl]methyl]amino]methyl]-1-ethylpyridinium iodide 2-[[Acetyl[[3-methoxy-2-(tetradecyloxy)phenyl]methyl]amino]methyl]-1-propylpyridinium iodide 2-[[Acetyl[[3-methoxy-4-(hexadecyloxy)phenyl]methyl]amino]methyl]-1-methylpyridinium iodide 2-[[Acetyl[[3-methoxy-4-(dodecyloxy)phenyl]methyl]amino]methyl]-1-ethylpyridinium iodide 2-[[Acetyl[[2-methyl-3-(tetradecyloxy)phenyl]methyl]amino]methyl]-1-propylpyridinium iodide 2-[[Acetyl[[2-methyl-4-(hexadecyloxy)phenyl]methyl]amino]methyl]-1-ethylpyridinium iodide 2-[[Acetyl[[2-methyl-4-(dodecyloxy)phenyl]methyl]amino]methyl]-1-methylpyridinium iodide 2-[[Acetyl[[3-chloro-2-(tetradecyloxy)phenyl]methyl]amino]methyl]-1-ethylpyridinium iodide 2-[[Acetyl[[3-chloro-4-(tetradecyloxy)phenyl]methyl]amino]methyl]-1-propylpyridinium iodide 2-[[Acetyl[[3-chloro-4-(dodecyloxy)phenyl]methyl]amino]methyl]-1-methylpyridinium iodide 2-[[Benzoyl[[3-(1,1-dimethylethyl)-2-(tetradecyloxy)phenyl]methyl]amino]methyl]-1-ethylpyridinium iodide 2-[[Benzoyl[[3-(1,1-dimethylethyl)-4-(tetradecyloxy)phenyl]methyl]amino]methyl]-1-propylpyridinium iodide 2-[[Benzoyl[[3-(1,1-dimethylethyl)-4-(hexadecyloxy)phenyl]methyl]amino]methyl]-1-ethylpyridinium iodide 2-[[Benzoyl[[3-(1,1-dimethylethyl)-4-(dodecyloxy)phenyl]methyl]amino]methyl]-1-propylpyridinium iodide 2-[[Benzoyl[[3-methoxy-4-(tetradecyloxy)phenyl]methyl]amino]methyl]-1-methylpyridinium iodide 2-[[Benzoyl[[3-methoxy-4-(hexadecyloxy)phenyl]methyl]amino]methyl]-1-ethylpyridinium iodide 2-[[Benzoyl[[3-methoxy-4-(dodecyloxy)phenyl]methyl]amino]methyl]-1-propylpyridinium iodide 2-[[Benzoyl[[2-methyl-4-(tetradecyloxy)phenyl]methyl]amino]methyl]-1-methylpyridinium iodide 2-[[Benzoyl[[2-methyl-4-(hexadecyloxy)phenyl]methyl]amino]methyl]-1-ethylpyridinium iodide 2-[[Benzoyl[[2-methyl-4-(dodecyloxy)phenyl]methyl]amino]methyl]-1-propylpyridinium iodide 2-[[Benzoyl[[3-chloro-4-(tetradecyloxy)phenyl]methyl]amino]methyl]-1-methylpyridinium iodide 2-[[Benzoyl[[3-chloro-4-(hexadecyloxy)phenyl]methyl]amino]methyl]-1-ethylpyridinium iodide 2-[[Benzoyl[[3-chloro-4-(dodecyloxy)phenyl]methyl]amino]methyl]-1-propylpyridinium iodide 2-[[(2-Methoxybenzoyl)][[3-(1,1-dimethylethyl)-2-(tetradecyloxy)phenyl]methyl]amino]methyl]-1-ethylpyridinium iodide 2-[[(2-Methoxybenzoyl)][[3-(1,1-dimethylethyl)-4-(tetradecyloxy)phenyl]methyl]amino]methyl]-1-propylpyridinium iodide 2-[[(2-Methoxybenzoyl)][3-(1,1-dimethylethyl)-4-(dodecyloxy)phenyl]methyl]amino]methyl]-1-methylpyridinium iodide 2-[[(2-Methoxybenzoyl)][3-methoxy-2-(tetradecyloxy)phenyl]methyl]amino]methyl]-1-ethylpyridinium iodide 2-[[(2-Methoxybenzoyl)][3-methoxy-4-(tetradecyloxy)phenyl]methyl]amino]methyl]-1-propylpyridinium iodide 2-[[(2-Methoxybenzoyl)][3-methoxy-4-(dodecyloxy)phenyl]methyl]amino]methyl]-1-methylpyridinium iodide 2-[[(2-Methoxybenzoyl)][2-methyl-3-(tetradecyloxy)phenyl]methyl]amino]methyl]-1-ethylpyridinium iodide 2-[[(2-Methoxybenzoyl)][2-methyl-4-(tetradecyloxy)phenyl]methyl]amino]methyl]-1-propylpyridinium iodide 2-[[(2-Methoxybenzoyl)][2-methyl-4-(dodecyloxy)phenyl]methyl]amino]methyl]-1-methylpyridinium iodide 2-[[(2-Methoxybenzoyl)][3-chloro-2-(tetradecyloxy)phenyl]methyl]amino]methyl]-1-ethylpyridinium iodide 2-[[(2-Methoxybenzoyl)][3-chloro-4-(tetradecyloxy)phenyl]methyl]amino]methyl]-1-propylpyridinium iodide 2-[[(2-Methoxybenzoyl)][3-chloro-4-(dodecyloxy)phenyl]methyl]amino]methyl]-1-methylpyridinium iodide 2-[[(2-Chlorobenzoyl)][3-(1,1-dimethylethyl)-2-(tetradecyloxy)phenyl]methyl]amino]methyl]-1-ethylpyridinium iodide 2-[[(2-Chlorobenzoyl)][3-(1,1-dimethylethyl)-4-(tetradecyloxy)phenyl]methyl]amino]methyl]-1-methylpyridinium iodide 2-[[(2-Chlorobenzoyl)][3-(1,1-dimethylethyl)-4-(hexadecyloxy)phenyl]methyl]amino]methyl]-1-ethylpyridinium iodide 2-[[(2-Chlorobenzoyl)][3-(1,1-dimethylethyl)-4-(dodecyloxy)phenyl]methyl]amino]methyl]-1-methylpyridinium iodide 2-[[(2-Chlorobenzoyl)][3-methoxy-2-(tetradecyloxy)phenyl]methyl]amino]methyl]-1-ethylpyridinium iodide 2-[[(2-Chlorobenzoyl)][3-methoxy-4-(tetradecyloxy)phenyl]methyl]amino]methyl]-1-propylpyridinium iodide 2-[[(2-Chlorobenzoyl)][3-methoxy-4-(dodecyloxy)phenyl]methyl]amino]methyl]-1-ethylpyridinium iodide 2-[[(2-Chlorobenzoyl)][2-methyl-4-(tetradecyloxy)phenyl]methyl]amino]methyl]-1-methylpyridinium iodide 2-[[(2-Chlorobenzoyl)][2-methyl-4-(hexadecyloxy)phenyl]methyl]amino]methyl]-1-ethylpyridinium iodide 2-[[(2-Chlorobenzoyl)][2-methyl-4-(dodecyloxy)phenyl]methyl]amino]methyl]-1-propylpyridinium iodide 2-[[(2-Chlorobenzoyl)][3-chloro-4-(tetradecyloxy)phenyl]methyl]amino]methyl]-1-methylpyridinium iodide 2-[[(2-Chlorobenzoyl)][3-chloro-4-(tetradecyloxy)phenyl]methyl]amino]methyl]-1-propylpyridinium iodide 2-[[(2-Chlorobenzoyl)][3-chloro-4-(dodecyloxy)phenyl]methyl]amino]methyl]-1-methylpyridinium iodide 2-[[Acetyl[3-(1,1-dimethylethyl)-2-(tetradecyloxy)phenyl]amino]methyl]-1-ethylpyridinium iodide 2-[[Acetyl[3-(1,1-dimethylethyl)-4-(tetradecyloxy)phenyl]amino]methyl]-1-propylpyridinium iodide 2-[[Acetyl[3-(1,1-dimethylethyl)-4-(dodecyloxy)phenyl]amino]methyl]-1-methylpyridinium iodide 2-[[Acetyl[3-(1,1-dimethylethyl)-4-(dodecyloxy)phenyl]amino]methyl]-1-propylpyridinium iodide 2-[[Acetyl[3-methoxy-4-(tetradecyloxy)phenyl]amino]methyl]-1-methylpyridinium iodide 2-[[Acetyl[3-methoxy-4-(hexadecyloxy)phenyl]amino]methyl]-1-ethylpyridinium iodide 2-[[Acetyl[3-methoxy-4-(dodecyloxy)phenyl]amino]methyl]-1-propylpyridinium iodide 2-[[Acetyl[2-methyl-4-(tetradecyloxy)phenyl]amino]methyl]-1-methylpyridinium iodide 2-[[Acetyl[2-methyl-4-(hexadecyloxy)phenyl]amino]methyl]-1-ethylpyridinium iodide 2-[[Acetyl[2-methyl-4-(dodecyloxy)phenyl]amino]methyl]-1-propylpyridinium iodide 2-[[Acetyl[3-chloro-4-(tetradecyloxy)phenyl]amino]methyl]-1-methylpyridinium iodide 2-[[Acetyl[3-chloro-4-(hexadecyloxy)phenyl]amino]methyl]-1-ethylpyridinium iodide 2-[[Acetyl[3-chloro-4-(dodecyloxy)phenyl]amino]methyl]-1-propylpyridinium iodide 2-[[[(4-Methylphenyl)sulfonyl][[3-(1,1-dimethylethyl)-4-(tetradecyloxy)phenyl]methyl]amino]methyl]-1-methylpyridinium iodide 2-[[[(4-Methylphenyl)sulfonyl][[3-(1,1-dimethylethyl)-4-(hexadecyloxy)phenyl]methyl]amino]methyl]-1-ethylpyridinium iodide 2-[[[(4-Methylphenyl)sulfonyl][[3-(1,1-dimethylethyl)-4-(dodecyloxy)phenyl]methyl]amino]methyl]-1-propylpyridinium iodide 2-[[[(4-Methylphenyl)sulfonyl][[3-methoxy-4-(tetradecyloxy)phenyl]methyl]amino]methyl]-1-methylpyridinium iodide 2-[[[(4-Methylphenyl)sulfonyl][[3-methoxy-4-(hexadecyloxy)phenyl]methyl]amino]methyl]-1-ethylpyridinium iodide 2-[[[(4-Methylphenyl)sulfonyl][[3-methoxy-4-(dodecyloxy)phenyl]methyl]amino]methyl]-1-propylpyridinium iodide 2-[[[(4-Methylphenyl)sulfonyl][[2-methyl-4-(tetradecyloxy)phenyl]methyl]amino]methyl]-1-ethylpyridinium iodide 2-[[[(4-Methylphenyl)sulfonyl][[2-methyl-4-(hexadecyloxy)phenyl]methyl]amino]methyl]-1-methylpyridinium iodide 2-[[[(4-Methylphenyl)sulfonyl][[2-methyl-4-(dodecyloxy)phenyl]methyl]amino]methyl]-1-ethylpyridinium iodide 2-[[[(4-Methylphenyl)sulfonyl][[3-chloro-2-(tetradecyloxy)phenyl]methyl]amino]methyl]-1-propylpyridinium iodide 2-[[[(4-Methylphenyl)sulfonyl][[3-chloro-4-(hexadecyloxy)phenyl]methyl]amino]methyl]-1-methylpyridinium iodide 2-[[[(4-Methylphenyl)sulfonyl][[3-chloro-4-(dodecyloxy)phenyl]methyl]amino]methyl]-1-ethylpyridinium iodide 2-[[(Methylsulfonyl)[[3-(1,1-dimethylethyl)-2-(tetradecyloxy)phenyl]methyl]amino]methyl]-1-propylpyridinium iodide 2-[[(Methylsulfonyl)[[3-(1,1-dimethylethyl)-4-(hexadecyloxy)phenyl]methyl]amino]methyl]-1-methylpyridinium iodide 2-[[(Methylsulfonyl)[[3-(1,1-dimethylethyl)-4-(hexadecyloxy)phenyl]methyl]amino]methyl]-1-propylpyridinium iodide 2-[[(Methylsulfonyl)[[3-methoxy-2-(tetradecyloxy)phenyl]methyl]amino]methyl]-1-methylpyridinium iodide 2-[[(Methylsulfonyl)[[3-methoxy-4-(tetradecyloxy)phenyl]methyl]amino]methyl]-1-ethylpyridinium iodide 2-[[(Methylsulfonyl)[[3-methoxy-4-(hexadecyloxy)phenyl]methyl]amino]methyl]-1-propylpyridinium iodide 2-[[(Methylsulfonyl)[[2-methyl-3-(tetradecyloxy)phenyl]methyl]amino]methyl]-1-methylpyridinium iodide 2-[[(Methylsulfonyl)[[2-methyl-3-(tetradecyloxy)phenyl]methyl]amino]methyl]-1-propylpyridinium iodide 2-[[(Methylsulfonyl)[[2-methyl-4-(hexadecyloxy)phenyl]methyl]amino]methyl]-1-methylpyridinium iodide 2-[[(Methylsulfonyl)[[2-methyl-4-(dodecyloxy)phenyl]methyl]amino]methyl]-1-ethylpyridinium iodide 2-[[(Methylsulfonyl)[[3-chloro-2-(tetradecyloxy)phenyl]methyl]amino]methyl]-1-propylpyridinium iodide 2-[[(Methylsulfonyl)[[3-chloro-4-(tetradecyloxy)phenyl]methyl]amino]methyl]-1-ethylpyridinium iodide 2-[[(Methylsulfonyl)[[3-chloro-4-(hexadecyloxy)phenyl]methyl]amino]methyl]-1-propylpyridinium iodide 3-[[Acetyl[[3-(1,1-dimethylethyl)-2-(tetradecyloxy)phenyl]methyl]amino]methyl]-1-methylpyridinium iodide 3-[[Acetyl[[3-(1,1-dimethylethyl)-2-(tetradecyloxy)phenyl]methyl]amino]methyl]-1-propylpyridinium iodide 3-[[Acetyl[[3-(1,1-dimethylethyl)-4-(hexadecyloxy)phenyl]methyl]amino]methyl]-1-methylpyridinium iodide 3-[[Acetyl[[3-(1,1-dimethylethyl)-4-(dodecyloxy)phenyl]methyl]amino]methyl]-1-ethylpyridinium iodide 3-[[Acetyl[[3-methoxy-2-(tetradecyloxy)phenyl]methyl]amino]methyl]-1-propylpyridinium iodide 3-[[Acetyl[[3-methoxy-4-(tetradecyloxy)phenyl]methyl]amino]methyl]-1-ethylpyridinium iodide 3-[[Acetyl[[3-methoxy-4-(hexadecyloxy)phenyl]methyl]amino]methyl]-1-propylpyridinium iodide 3-[[Acetyl[[3-methoxy-4-(dodecyloxy)phenyl]methyl]amino]methyl]-1-ethylpyridinium iodide 3-[[Acetyl[[2-methyl-3-(tetradecyloxy)phenyl]methyl]amino]methyl]-1-propylpyridinium iodide 3-[[Acetyl[[2-methyl-4-(hexadecyloxy)phenyl]methyl]amino]methyl]-1-methylpyridinium iodide 3-[[Acetyl[[2-methyl-4-(dodecyloxy)phenyl]methyl]amino]methyl]-1-ethylpyridinium iodide 3-[[Acetyl[[3-chloro-2-(tetradecyloxy)phenyl]methyl]amino]methyl]-1-propylpyridinium iodide 3-[[Acetyl[[3-chloro-4-(hexadecyloxy)phenyl]methyl]amino]methyl]-1-ethylpyridinium iodide 3-[[Benzoyl[[3-(1,1-dimethylethyl)-2-(tetradecyloxy)phenyl]methyl]amino]methyl]-1-methylpyridinium iodide 3-[[Benzoyl[[3-(1,1-dimethylethyl)-4-(tetradecyloxy)phenyl]methyl]amino]methyl]-1-ethylpyridinium iodide 3-[[Benzoyl[[3-(1,1-dimethylethyl)-4-(hexadecyloxy)phenyl]methyl]amino]methyl]-1-methylpyridinium iodide 3-[[Benzoyl[[3-(1,1-dimethylethyl)-4-(dodecyloxy)phenyl]methyl]amino]methyl]-1-ethylpyridinium iodide 3-[[Benzoyl[[3-methoxy-2-(tetradecyloxy)phenyl]methyl]amino]methyl]-1-propylpyridinium iodide 3-[[Benzoyl[[3-methoxy-4-(hexadecyloxy)phenyl]methyl]amino]methyl]-1-methylpyridinium iodide 3-[[Benzoyl[[3-methoxy-4-(dodecyloxy)phenyl]methyl]amino]methyl]-1-ethylpyridinium iodide 3-[[Benzoyl[[2-methyl-3-(tetradecyloxy)phenyl]methyl]amino]methyl]-1-propylpyridinium iodide 3-[[Benzoyl[[2-methyl-4-(hexadecyloxy)phenyl]methyl]amino]methyl]-1-methylpyridinium iodide 3-[[Benzoyl[[2-methyl-4-(dodecyloxy)phenyl]methyl]amino]methyl]-1-ethylpyridinium iodide 3-[[Benzoyl[[3-chloro-2-(tetradecyloxy)phenyl]methyl]amino]methyl]-1-propylpyridinium iodide 3-[[Benzoyl[[3-chloro-4-(tetradecyloxy)phenyl]methyl]amino]methyl]-1-ethylpyridinium iodide 3-[[Benzoyl[[3-chloro-4-(hexadecyloxy)phenyl]methyl]amino]methyl]-1-propylpyridinium iodide 3-[[(2-Methoxybenzoyl)[[3-(1,1-dimethylethyl)-2-(tetradecyloxy)phenyl]methyl]amino]methyl]-1-methylpyridinium iodide 3-[[(2-Methoxybenzoyl)[[3-(1,1-dimethylethyl)-4-(tetradecyloxy)phenyl]methyl]amino]methyl]-1-ethylpyridinium iodide 3-[[(2-Methoxybenzoyl)[[3-(1,1-dimethylethyl)-4-(hexadecyloxy)phenyl]methyl]amino]methyl]-1-propylpyridinium iodide 3-[[(2-Methoxybenzoyl)[[3-methoxy-2-(tetradecyloxy)phenyl]methyl]amino]methyl]-1-methylpyridinium iodide 3-[[(2-Methoxybenzoyl)[[3-methoxy-4-(tetradecyloxy)phenyl]methyl]amino]methyl]-1-ethylpyridinium iodide 3-[[(2-Methoxybenzoyl)[[3-methoxy-4-(hexadecyloxy)phenyl]methyl]amino]methyl]-1-propylpyridinium iodide 3-[[(2-Methoxybenzoyl)[[2-methyl-3-(tetradecyloxy)phenyl]methyl]amino]methyl]-1-ethylpyridinium iodide 3-[[(2-Methoxybenzoyl)[[2-methyl-4-(tetradecyloxy)phenyl]methyl]amino]methyl]-1-propylpyridinium iodide 3-[[(2-Methoxybenzoyl)[[2-methyl-4-(dodecyloxy)phenyl]methyl]amino]methyl]-1-methylpyridinium iodide 3-[[(2-Methoxybenzoyl)[[3-chloro-2-(tetradecyloxy)phenyl]methyl]amino]methyl]-1-ethylpyridinium iodide 3-[[(2-Methoxybenzoyl)[[3-chloro-4-(tetradecyloxy)phenyl]methyl]amino]methyl]-1-propylpyridinium iodide 3-[[(2-Methoxybenzoyl)[[3-chloro-4-(dodecyloxy)phenyl]methyl]amino]methyl]-1-methylpyridinium iodide 3-[[(2-Methoxybenzoyl)[[3-chloro-4-(dodecyloxy)phenyl]methyl]amino]methyl]-1-propylpyridinium iodide 3-[[(2-Chlorobenzoyl)[[3-(1,1-dimethylethyl)-4-(tetradecyloxy)phenyl]methyl]amino]methyl]-1-methylpyridinium iodide 3-[[(2-Chlorobenzoyl)[[3-(1,1-dimethylethyl)-4-(hexadecyloxy)phenyl]methyl]amino]methyl]-1-ethylpyridinium iodide 3-[[(2-Chlorobenzoyl)[[3-methoxy-2-(tetradecyloxy)phenyl]methyl]amino]methyl]-1-methylpyridinium iodide 3-[[(2-Chlorobenzoyl)[[3-methoxy-4-(tetradecyloxy)phenyl]methyl]amino]methyl]-1-propylpyridinium iodide 3-[[(2-Chlorobenzoyl)[[3-methoxy-4-(dodecyloxy)phenyl]methyl]amino]methyl]-1-ethylpyridinium iodide 3-[[(2-Chlorobenzoyl)[[2-methyl-4-(tetradecyloxy)phenyl]methyl]amino]methyl]-1-methylpyridinium iodide 3-[[(2-Chlorobenzoyl)[[2-methyl-4-(tetradecyloxy)phenyl]methyl]amino]methyl]-1-propylpyridinium iodide 3-[[(2-Chlorobenzoyl)[[2-methyl-4-(dodecyloxy)phenyl]methyl]amino]methyl]-1-ethylpyridinium iodide 3-[[(2-Chlorobenzoyl)[[3-chloro-4-(tetradecyloxy)phenyl]methyl]amino]methyl]-1-methylpyridinium iodide 3-[[(2-Chlorobenzoyl)[[3-chloro-4-(hexadecyloxy)phenyl]methyl]amino]methyl]-1-ethylpyridinium iodide 3-[[Acetyl[3-(1,1-dimethylethyl)-2-(tetradecyloxy)phenyl]amino]methyl]-1-methylpyridinium iodide 3-[[Acetyl[3-(1,1-dimethylethyl)-2-(tetradecyloxy)phenyl]amino]methyl]-1-propylpyridinium iodide 3-[[Acetyl[3-(1,1-dimethylethyl)-4-(hexadecyloxy)phenyl]amino]methyl]-1-methylpyridinium iodide 3-[[Acetyl[3-(1,1-dimethylethyl)-4-(dodecyloxy)phenyl]amino]methyl]-1-ethylpyridinium iodide 3-[[Acetyl[3-methoxy-4-(tetradecyloxy)phenyl]amino]methyl]-1-ethylpyridinium iodide 3-[[Acetyl[3-methoxy-4-(hexadecyloxy)phenyl]amino]methyl]-1-methylpyridinium iodide 3-[[Acetyl[3-methoxy-4-(dodecyloxy)phenyl]amino]methyl]-1-ethylpyridinium iodide 3-[[Acetyl[2-methyl-3-(tetradecyloxy)phenyl]amino]methyl]-1-propylpyridinium iodide 3-[[Acetyl[2-methyl-4-(hexadecyloxy)phenyl]amino]methyl]-1-methylpyridinium iodide 3-[[Acetyl[2-methyl-4-(dodecyloxy)phenyl]amino]methyl]-1-ethylpyridinium iodide 3-[[Acetyl[3-chloro-2-(tetradecyloxy)phenyl]amino]methyl]-1-propylpyridinium iodide 3-[[Acetyl[3-chloro-4-(hexadecyloxy)phenyl]amino]methyl]-1-methylpyridinium iodide 3-[[Acetyl[3-chloro-4-(dodecyloxy)phenyl]amino]methyl]-1-ethylpyridinium iodide 3-[[[(4-Methylphenyl)sulfonyl][[3-(1,1-dimethylethyl)-4-(tetradecyloxy)phenyl]methyl]amino]methyl]-1-methylpyridinium iodide 3-[[[(4-Methylphenyl)sulfonyl][[3-(1,1-dimethylethyl)-4-(hexadecyloxy)phenyl]methyl]amino]methyl]-1-ethylpyridinium iodide 3-[[[(4-Methylphenyl)sulfonyl][[3-(1,1-dimethylethyl)-4-(dodecyloxy)phenyl]methyl]amino]methyl]-1-propylpyridinium iodide 3-[[[(4-Methylphenyl)sulfonyl][[3-methoxy-4-(tetradecyloxy)phenyl]methyl]amino]methyl]-1-methylpyridinium iodide 3-[[[(4-Methylphenyl)sulfonyl][[3-methoxy-4-(hexadecyloxy)phenyl]methyl]amino]methyl]-1-ethylpyridinium iodide 3-[[[(4-Methylphenyl)sulfonyl][[2-methyl-3-(tetradecyloxy)phenyl]methyl]amino]methyl]-1-methylpyridinium iodide 3-[[[(4-Methylphenyl)sulfonyl][[2-methyl-4-(tetradecyloxy)phenyl]methyl]amino]methyl]-1-ethylpyridinium iodide 3-[[[(4-Methylphenyl)sulfonyl][[2-methyl-4-(hexadecyloxy)phenyl]methyl]amino]methyl]-1-propylpyridinium iodide 3-[[[(4-Methylphenyl)sulfonyl][[3-chloro-2-(tetradecyloxy)phenyl]methyl]amino]methyl]-1-methylpyridinium iodide 3-[[[(4-Methylphenyl)sulfonyl][[3-chloro-4-(tetradecyloxy)phenyl]methyl]amino]methyl]-1-propylpyridinium iodide 3-[[[(4-Methylphenyl)sulfonyl][[3-chloro-4-(dodecyloxy)phenyl]methyl]amino]methyl]-1-methylpyridinium iodide 3-[[(Methylsulfonyl)[[3-(1,1-dimethylethyl)-2-(tetradecyloxy)phenyl]methyl]amino]methyl]-1-ethylpyridinium iodide 3-[[(Methylsulfonyl)[[3-(1,1-dimethylethyl)-4-(tetradecyloxy)phenyl]methyl]amino]methyl]-1-propylpyridinium iodide 3-[[(Methylsulfonyl)[[3-(1,1-dimethylethyl)-4-(dodecyloxy)phenyl]methyl]amino]methyl]-1-methylpyridinium iodide 3-[[(Methylsulfonyl)[[3-methoxy-2-(tetradecyloxy)phenyl]methyl]amino]methyl]-1-ethylpyridinium iodide 3-[[(Methylsulfonyl)[[3-methoxy-4-(tetradecyloxy)phenyl]methyl]amino]methyl]-1-propylpyridinium iodide 3-[[(Methylsulfonyl)[[3-methoxy-4-(dodecyloxy)phenyl]methyl]amino]methyl]-1-methylpyridinium iodide 3-[[(Methylsulfonyl)[[2-methyl-3-(tetradecyloxy)phenyl]methyl]amino]methyl]-1-propylpyridinium iodide 3-[[(Methylsulfonyl)[[2-methyl-4-(hexadecyloxy)phenyl]methyl]amino]methyl]-1-methylpyridinium iodide 3-[[(Methylsulfonyl)[[2-methyl-4-(dodecyloxy)phenyl]methyl]amino]methyl]-1-propylpyridinium iodide 3-[[(Methylsulfonyl)[[3-chloro-4-(tetradecyloxy)phenyl]methyl]amino]methyl]-1-methylpyridinium iodide 3-[[(Methylsulfonyl)[[3-chloro-4-(tetradecyloxy)phenyl]methyl]amino]methyl]-1-propylpyridinium iodide 3-[[(Methylsulfonyl)[[3-chloro-4-(dodecyloxy)phenyl]methyl]amino]methyl]-1-ethylpyridinium iodide 4-[[Acetyl[[3-(1,1-dimethylethyl)-2-(tetradecyloxy)phenyl]methyl]amino]methyl]-1-propylpyridinium iodide 4-[[Acetyl[[3-(1,1-dimethylethyl)-4-(hexadecyloxy)phenyl]methyl]amino]methyl]-1-methylpyridinium iodide 4-[[Acetyl[[3-(1,1-dimethylethyl)-4-(dodecyloxy)phenyl]methyl]amino]methyl]-1-ethylpyridinium iodide 4-[[Acetyl[[3-methoxy-2-(tetradecyloxy)phenyl]methyl]amino]methyl]-1-propylpyridinium iodide 4-[[Acetyl[[3-methoxy-4-(hexadecyloxy)phenyl]methyl]amino]methyl]-1-methylpyridinium iodide 4-[[Acetyl[[3-methoxy-4-(dodecyloxy)phenyl]methyl]amino]methyl]-1-ethylpyridinium iodide 4-[[Acetyl[[2-methyl-3-(tetradecyloxy)phenyl]methyl]amino]methyl]-1-propylpyridinium iodide 4-[[Acetyl[[2-methyl-4-(hexadecyloxy)phenyl]methyl]amino]methyl]-1-methylpyridinium iodide 4-[[Acetyl[[2-methyl-4-(dodecyloxy)phenyl]methyl]amino]methyl]-1-ethylpyridinium iodide 4-[[Acetyl[[3-chloro-2-(tetradecyloxy)phenyl]methyl]amino]methyl]-1-propylpyridinium iodide 4-[[Acetyl[[3-chloro-4-(hexadecyloxy)phenyl]methyl]amino]methyl]-1-methylpyridinium iodide 4-[[Acetyl[[3-chloro-4-(dodecyloxy)phenyl]methyl]amino]methyl]-1-ethylpyridinium iodide 4-[[Benzoyl[[3-(1,1-dimethylethyl)-2-(tetradecyloxy)phenyl]methyl]amino]methyl]-1-propylpyridinium iodide 4-[[Benzoyl[[3-(1,1-dimethylethyl)-4-(hexadecyloxy)phenyl]methyl]amino]methyl]-1-methylpyridinium iodide 4-[[Benzoyl[[3-(1,1-dimethylethyl)-4-(dodecyloxy)phenyl]methyl]amino]methyl]-1-ethylpyridinium iodide 4-[[Benzoyl[[3-methoxy-2-(tetradecyloxy)phenyl]methyl]amino]methyl]-1-propylpyridinium iodide 4-[[Benzoyl[[3-methoxy-4-(hexadecyloxy)phenyl]methyl]amino]methyl]-1-methylpyridinium iodide 4-[[Benzoyl[[3-methoxy-4-(dodecyloxy)phenyl]methyl]amino]methyl]-1-ethylpyridinium iodide 4-[[Benzoyl[[2-methyl-3-(tetradecyloxy)phenyl]methyl]amino]methyl]-1-propylpyridinium iodide 4-[[Benzoyl[[2-methyl-4-(hexadecyloxy)phenyl]methyl]amino]methyl]-1-methylpyridinium iodide 4-[[Benzoyl[[2-methyl-4-(dodecyloxy)phenyl]methyl]amino]methyl]-1-propylpyridinium iodide 4-[[Benzoyl[[3-chloro-4-(tetradecyloxy)phenyl]methyl]amino]methyl]-1-methylpyridinium iodide 4-[[Benzoyl[[3-chloro-4-(hexadecyloxy)phenyl]methyl]amino]methyl]-1-ethylpyridinium iodide 4-[[(2-Methoxybenzoyl)[[3-(1,1-dimethylethyl)-2-(tetradecyloxy)phenyl]methyl]amino]methyl]-1-methylpyridinium iodide 4-[[(2-Methoxybenzoyl)[[3-(1,1-dimethylethyl)-4-(hexadecyloxy)phenyl]methyl]amino]methyl]-1-methylpyridinium iodide 4-[[(2-Methoxybenzoyl)[[3-(1,1-dimethylethyl)-4-(dodecyloxy)phenyl]methyl]amino]methyl]-1-ethylpyridinium iodide 4-[[(2-Methoxybenzoyl)[[3-methoxy-4-(tetradecyloxy)phenyl]methyl]amino]methyl]-1-methylpyridinium iodide 4-[[(2-Methoxybenzoyl)[[3-methoxy-4-(hexadecyloxy)phenyl]methyl]amino]methyl]-1-propylpyridinium iodide 4-[[(2-Methoxybenzoyl)[[2-methyl-3-(tetradecyloxy)phenyl]methyl]amino]methyl]-1-ethylpyridinium iodide 4-[[(2-Methoxybenzoyl)[[2-methyl-4-(hexadecyloxy)phenyl]methyl]amino]methyl]-1-methylpyridinium iodide 4-[[(2-Methoxybenzoyl)[[2-methyl-4-(dodecyloxy)phenyl]methyl]amino]methyl]-1-ethylpyridinium iodide 4-[[(2-Methoxybenzoyl)[[3-chloro-2-(tetradecyloxy)phenyl]methyl]amino]methyl]-1-propylpyridinium iodide 4-[[(2-Methoxybenzoyl)[[3-chloro-4-(hexadecyloxy)phenyl]methyl]amino]methyl]-1-methylpyridinium iodide 4-[[(2-Chlorobenzoyl)[[3-(1,1-dimethylethyl)-2-(tetradecyloxy)phenyl]methyl]amino]methyl]-1-methylpyridinium iodide 4-[[(2-Chlorobenzoyl)[[3-(1,1-dimethylethyl)-4-(tetradecyloxy)phenyl]methyl]amino]methyl]-1-ethylpyridinium iodide 4-[[(2-Chlorobenzoyl)[[3-(1,1-dimethylethyl)-4-(dodecyloxy)phenyl]methyl]amino]methyl]-1-methylpyridinium iodide 4-[[(2-Chlorobenzoyl)[[3-methoxy-2-(tetradecyloxy)phenyl]methyl]amino]methyl]-1-ethylpyridinium iodide 4-[[(2-Chlorobenzoyl)[[3-methoxy-4-(hexadecyloxy)phenyl]methyl]amino]methyl]-1-methylpyridinium iodide 4-[[(2-Chlorobenzoyl)[[3-methoxy-4-(dodecyloxy)phenyl]methyl]amino]methyl]-1-ethylpyridinium iodide 4-[[(2-Chlorobenzoyl)[[2-methyl-3-(tetradecyloxy)phenyl]methyl]amino]methyl]-1-propylpyridinium iodide 4-[[(2-Chlorobenzoyl)[[2-methyl-4-(hexadecyloxy)phenyl]methyl]amino]methyl]-1-methylpyridinium iodide 4-[[(2-Chlorobenzoyl)[[3-chloro-2-(tetradecyloxy)phenyl]methyl]amino]methyl]-1-methylpyridinium iodide 4-[[(2-Chlorobenzoyl)[[3-chloro-4-(tetradecyloxy)phenyl]methyl]amino]methyl]-1-ethylpyridinium iodide 4-[[(2-Chlorobenzoyl)[[3-chloro-4-(hexadecyloxy)phenyl]methyl]amino]methyl]-1-propylpyridinium iodide 4-[[Acetyl[3-(1,1-dimethylethyl)-2-(tetradecyloxy)phenyl]amino]methyl]-1-methylpyridinium iodide 4-[[Acetyl[3-(1,1-dimethylethyl)-4-(tetradecyloxy)phenyl]amino]methyl]-1-ethylpyridinium iodide 4-[[Acetyl[3-(1,1-dimethylethyl)-4-(hexadecyloxy)phenyl]amino]methyl]-1-propylpyridinium iodide 4-[[Acetyl[3-methoxy-2-(tetradecyloxy)phenyl]amino]methyl]-1-methylpyridinium iodide 4-[[Acetyl[3-methoxy-4-(hexadecyloxy)phenyl]amino]methyl]-1-methylpyridinium iodide 4-[[Acetyl[3-methoxy-4-(dodecyloxy)phenyl]amino]methyl]-1-ethylpyridinium iodide 4-[[Acetyl[2-methyl-4-(tetradecyloxy)phenyl]amino]methyl]-1-methylpyridinium iodide 4-[[Acetyl[2-methyl-4-(hexadecyloxy)phenyl]amino]methyl]-1-ethylpyridinium iodide 4-[[Acetyl[3-chloro-2-(tetradecyloxy)phenyl]amino]methyl]-1-ethylpyridinium iodide 4-[[Acetyl[3-chloro-4-(hexadecyloxy)phenyl]amino]methyl]-1-ethylpyridinium iodide 4-[[Acetyl[3-chloro-4-(dodecyloxy)phenyl]amino]methyl]-1-propylpyridinium iodide 4-[[[(4-Methylphenyl)sulfonyl][[3-(1,1-dimethylethyl)-4-(tetradecyloxy)phenyl]methyl]amino]methyl]-1-methylpyridinium iodide 4-[[[(4-Methylphenyl)sulfonyl][[3-(1,1-dimethylethyl)-4-(dodecyloxy)phenyl]methyl]amino]methyl]-1-ethylpyridinium iodide 4-[[[(4-Methylphenyl)sulfonyl][[3-methoxy-2-(tetradecyloxy)phenyl]methyl]amino]methyl]-1-propylpyridinium iodide 4-[[[(4-Methylphenyl)sulfonyl][[3-methoxy-4-(hexadecyloxy)phenyl]methyl]amino]methyl]-1-methylpyridinium iodide 4-[[[(4-Methylphenyl)sulfonyl][[3-methoxy-4-(dodecyloxy)phenyl]methyl]amino]methyl]-1-ethylpyridinium iodide 4-[[[(4-Methylphenyl)sulfonyl][[2-methyl-4-(hexadecyloxy)phenyl]methyl]amino]methyl]-1-methylpyridinium iodide 4-[[[(4-Methylphenyl)sulfonyl][[2-methyl-4-(dodecyloxy)phenyl]methyl]amino]methyl]-1-propylpyridinium iodide 4-[[[(4-Methylphenyl)sulfonyl][[3-chloro-4-(tetradecyloxy)phenyl]methyl]amino]methyl]-1-methylpyridinium iodide 4-[[[(4-Methylphenyl)sulfonyl][[3-chloro-4-(hexadecyloxy)phenyl]methyl]amino]methyl]-1-ethylpyridinium iodide 4-[[[(4-Methylphenyl)sulfonyl][[3-chloro-4-(dodecyloxy)phenyl]methyl]amino]methyl]-1-propylpyridinium iodide 4-[[(Methylsulfonyl)[[3-(1,1-dimethylethyl)-4-(tetradecyloxy)phenyl]methyl]amino]methyl]-1-propylpyridinium iodide 4-[[(Methylsulfonyl)[[3-(1,1-dimethylethyl)-4-(dodecyloxy)phenyl]methyl]amino]methyl]-1-propylpyridinium iodide 4-[[(Methylsulfonyl)[[3-methoxy-4-(tetradecyloxy)phenyl]methyl]amino]methyl]-1-methylpyridinium iodide 4-[[(Methylsulfonyl)[[3-methoxy-4-(hexadecyloxy)phenyl]methyl]amino]methyl]-1-ethylpyridinium iodide 4-[[(Methylsulfonyl)[[3-methoxy-4-(dodecyloxy)phenyl]methyl]amino]methyl]-1-propylpyridinium iodide 4-[[(Methylsulfonyl)[[2-methyl-4-(tetradecyloxy)phenyl]methyl]amino]methyl]-1-propylpyridinium iodide 4-[[(Methylsulfonyl)[[2-methyl-4-(dodecyloxy)phenyl]methyl]amino]methyl]-1-methylpyridinium iodide 4-[[(Methylsulfonyl)[[3-chloro-2-(tetradecyloxy)phenyl]methyl]amino]methyl]-1-ethylpyridinium iodide 4-[[(Methylsulfonyl)[[3-chloro-4-(tetradecyloxy)phenyl]methyl]amino]methyl]-1-propylpyridinium iodide 4-[[(Methylsulfonyl)[[3-chloro-4-(hexadecyloxy)phenyl]methyl]amino]methyl]-1-propylpyridinium iodide

We claim:

1. A compound of the formula:

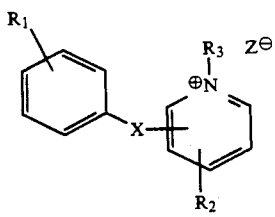

wherein:

(A) X is a divalent radical of:

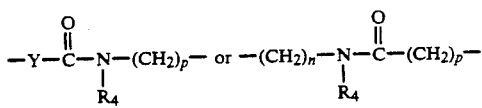

wherein Y is a divalent radical $(CH_2)_n$, or p is the integer 1, 2, or 3; n is the integer 0, 1, or 2; $R_4$ is hydrogen, phenyl, —$COR_6$ or —$SO_2R_7$; wherein $R_6$ is $C_1$-$C_6$ alkyl, $C_2$-$C_6$ alkenyl, $C_1$-$C_6$ alkylamino, $C_1$-$C_6$ alkoxy, phenyl, aminophenyl, substituted phenyl or substituted aminophenyl and the substituents are of one or more of the following $C_1$-$C_4$ alkyl, $C_1$-$C_4$ alkoxy, halogen or trifluoromethyl; $R_7$ is $C_1$-$C_{25}$ alkyl, $C_2$-$C_{25}$ alkenyl, phenyl or substituted phenyl and the substituents are $C_1$-$C_{20}$ alkyl, $C_1$-$C_{20}$ alkoxy, halogen or trifluoromethyl;

(B) $R_1$ is one or more substituents of the aromatic ring which may be the same or different and is (i) $C_1$-$C_{25}$ alkyl, $C_2$-$C_{25}$ alkenyl, $C_1$-$C_{25}$ alkoxy, $C_2$-$C_{25}$ alkenyloxy, $C_1$-$C_{25}$ thioalkyl, phenyl, phenoxy, substituted phenyl or substituted phenoxy wherein the substituents are $C_1$-$C_{20}$ alkyl, $C_1$-$C_{20}$ alkoxy, halogen, or trifluoromethyl;

(ii) halogen, trifluoromethyl, cyano, or nitro;

(iii) —$CO_2R_7$, —$CONHR_7$, —$OCONHR_7$, or —$NHCOR_7$ wherein $R_7$ is as previously described above;

(C) the moiety $R_2$ is one or more substituents of the pyridine ring which may be in any position and are hydrogen, $C_1$-$C_5$ alkyl, $C_1$-$C_5$ alkoxy, or halogen;

(D) the heterocycle is bonded to the X-group at optionally the 2, 3, or 4 position.

(E) the group $R_3$ is $C_1$-$C_8$ alkyl, $C_1$-$C_8$ halogen (bromine, chlorine or fluorine) substituted alkyl, hydrogen, or N-oxide; and (F) $Z^\ominus$ represents a pharmacologically acceptable anion.

2. A compound according to claim 1 wherein:

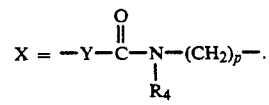

3. A compound according to claim 1 wherein:

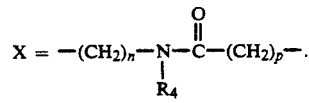

4. A compound according to claim 2 wherein: $Y=$—$(CH_2)_n$—.

5. The compound according to claim 4, 1-ethyl-2-[[[4-(tetradecyloxy)benzoyl]amino]methyl]pyridinium iodide.

6. The compound according to claim 4, 1-methyl-2-[[[4-(tetradecyloxy)benzoyl]amino]methyl]pyridinium iodide.

7. The compound according to claim 4, 1-methyl-2-[2-[[4-(tetradecyloxy)benzoyl]amino]ethyl]pyridinium iodide.

8. The compound according to claim 4, 1-methyl-2-[2-[[[4-(tetradecyloxy)phenyl]acetyl]amino]ethyl]-pyridinium iodide.

9. The compound according to claim 4, 2-[acetyl[4-(tetradecyloxy)benzoyl]amino]methyl]-1-methylpyridinium iodide.

10. The compound according to claim 4, 2-[[(2-methoxybenzoyl) [4-(tetradecyloxy)benzoyl]amino]methyl]-1-methylpyridinium iodide.

11. The compound according to claim 4, 3-[[acetyl[4-(tetradecyloxy)benzoyl]amino]methyl]-1-methylpyridinium iodide.

12. The compound according to claim 4, 2-[[acetyl[3-(1,1-dimethylethyl)-4-(tetradecyloxy)benzoyl]amino]methyl]-1-methylpyridinium iodide.

13. The compound according to claim 4, 2-[[acetyl[3-methoxy-4-(tetradecyloxy)benzoyl]amino]methyl]-1-methylpyridinium iodide.

14. The compound according to claim 4, 2-[[acetyl[4-methoxy-3-(tetradecyloxy)benzoyl]amino]methyl]-1-methylpyridinium iodide.

15. The compound according to claim 4, 2-[[acetyl[3-methoxy-4-(tetradecyloxy)benzoyl]amino]methyl]-1-ethylpyridinium iodide.

16. The compound according to claim 4, 3-[[acetyl[3-(1,1-dimethylethyl)-4-(tetradecyloxy)benzoyl]amino]methyl]-1-methylpyridinium iodide.

17. The compound according to claim 4, 4-[[acetyl[3-(1,1-dimethylethyl)-4-(tetradecyloxy)benzoyl]amino]methyl]-1-methylpyridinium iodide.

18. The compound according to claim 4, 2-[[acetyl[4-(decyloxy)-3-(1,1-dimethylethyl)benzoyl]amino]methyl]-1-methylpyridinium iodide.

19. The compound according to claim 4, 1-methyl-2-[[[3,4-bis(tetradecyloxy)benzoyl]amino]methyl]-pyridinium iodide.

20. The compound according to claim 4, 2-[[acetyl[3,4-bis(tetradecyloxy)benzoyl]amino]methyl]-1-methylpyridinium iodide.

21. The compound according to claim 4, 2-[[acetyl[3,4-bis(heptyloxy)benzoyl]amino]methyl]-1-methylpyridinium iodide.

22. The compound according to claim 4, 1-methyl-2-[[(methylsulfonyl)[4-(tetradecyloxy)benzoyl]amino]methyl]pyridinium salt with trifluoromethanesulfonic acid.

23. A composition of matter in dosage unit form which comprises a compound of claim 1 in association with a pharmaceutically acceptable carrier.

24. A method for inhibiting the biological effects of PAF in a mammal which comprises administering to the mammal a compound of claim 1 in an amount to inhibit PAF effects.

25. A method for treating anaphylactic and septic shock in a mammal which comprises administering to said mammal an effective amount of a compound of claim 1.

* * * * *